(12) United States Patent
Lumeras Amador et al.

(10) Patent No.: US 8,334,294 B2
(45) Date of Patent: Dec. 18, 2012

(54) 4,8-DIPHENYL-POLYAZANAPHTHALENE DERIVATIVES

(75) Inventors: Wenceslao Lumeras Amador, San Just Desvern (ES); Paul Robert Eastwood, Rubi (ES)

(73) Assignee: Almirall, S.A., Barcelona (ES)

( * ) Notice: Subject to any disclaimer, the term of this patent is extended or adjusted under 35 U.S.C. 154(b) by 332 days.

(21) Appl. No.: 12/597,187

(22) PCT Filed: Apr. 25, 2008

(86) PCT No.: PCT/EP2008/003357
§ 371 (c)(1), (2), (4) Date: Jan. 7, 2010

(87) PCT Pub. No.: WO2008/131922
PCT Pub. Date: Nov. 6, 2008

(65) Prior Publication Data
US 2010/0130517 A1     May 27, 2010

(30) Foreign Application Priority Data

Apr. 26, 2007   (ES) .................................. 200701132

(51) Int. Cl.
*A01N 43/42* (2006.01)
*A01N 43/90* (2006.01)
*A61K 31/44* (2006.01)
*A61K 31/519* (2006.01)

(52) U.S. Cl. ...................... 514/264.1; 514/300; 544/279; 546/122

(58) Field of Classification Search ................ 514/264.1, 514/300; 544/279; 546/122
See application file for complete search history.

(56) References Cited

U.S. PATENT DOCUMENTS

| | | | |
|---|---|---|---|
| 4,959,368 A | 9/1990 | Awaya et al. | |
| 5,414,088 A | 5/1995 | Von Der Saal et al. | |
| 6,586,447 B1 | 7/2003 | Lyssikatos et al. | |
| 8,106,190 B2 | 1/2012 | Kuramochi et al. | |
| 2003/0166724 A1 | 9/2003 | Hangeland | |
| 2005/0131014 A1* | 6/2005 | Collini et al. ................ | 514/311 |
| 2006/0106048 A1 | 5/2006 | Inoue et al. | |
| 2007/0213341 A1 | 9/2007 | Chen et al. | |
| 2008/0009486 A1 | 1/2008 | Chen et al. | |
| 2010/0120731 A1 | 5/2010 | Juan et al. | |
| 2010/0227881 A1 | 9/2010 | Javaloyes et al. | |
| 2011/0046097 A1 | 2/2011 | Eastwood et al. | |
| 2011/0053936 A1 | 3/2011 | Eastwood et al. | |

FOREIGN PATENT DOCUMENTS

| | | |
|---|---|---|
| CN | 1502608 A | 6/2004 |
| EP | 0 549 892 A1 | 7/1993 |
| EP | 0 743 066 A2 | 11/1996 |
| JP | 57-203068 | 12/1982 |
| JP | 10-79183 | 3/1989 |
| JP | 1996-005887 | 1/1996 |
| JP | 9-104638 | 4/1997 |
| WO | WO 87/04928 | 8/1987 |
| WO | WO 91/04974 | 4/1991 |
| WO | WO 91/06545 | 5/1991 |
| WO | WO 99/01449 | 1/1999 |
| WO | WO 99/64400 A1 | 12/1999 |
| WO | WO 00/63204 | 10/2000 |
| WO | WO 00/66583 | 11/2000 |
| WO | WO 01/01986 A1 | 1/2001 |
| WO | WO 01/29042 A1 | 4/2001 |
| WO | WO 02/02549 A1 | 1/2002 |
| WO | WO 02/46184 A1 | 6/2002 |
| WO | WO 02/058695 A1 | 8/2002 |
| WO | WO 02/072576 A1 | 9/2002 |
| WO | WO 02/072579 A1 | 9/2002 |
| WO | WO 03/008413 A1 | 1/2003 |
| WO | WO 03/033502 A1 | 4/2003 |
| WO | WO 03/043998 A1 | 5/2003 |
| WO | WO 03/087087 A2 | 10/2003 |
| WO | WO 03/097062 A1 | 11/2003 |
| WO | WO 03/103590 A2 | 12/2003 |
| WO | WO 2004/010995 A1 | 2/2004 |

(Continued)

OTHER PUBLICATIONS

Zhou, et al., TNFR-induced the NF-κB, but not the ERK, p38MAPK or JNK activation, mediates TNF-induced ICAM-1 and VCAM-1 expression on endothelial cells, Cellular Signalling 19, 1238-1248 (2007).*
International Search Report for PCT/EP2008/003357 dated Aug. 12, 2008 (2 pages).
U.S. Appl. No. 12/376,499, filed Apr. 1, 2009, Javaloyes et al.
U.S. Appl. No. 12/529,490, filed Sep. 14, 2009, Juan et al.
U.S. Appl. No. 12/936,784, filed Oct. 26, 2010, Eastwood et al.
U.S. Appl. No. 12/989,696, filed Oc. 26, 2010, Eastwood et al.
Adams, R. H., et al., "Essential role of p38α MAP kinase in placental but not embryonic cardiovascular development," Molecular Cell, 6:109-116 (2000).
Allen, M., et al., "Deficiency of the stress kinase p38a results in embryonic lethality: characterization of the kinase dependance of stress responses of enzyme-deficient embryonic stem cells," J. Exp. Med. 191(5): 859-869 (2000).

(Continued)

*Primary Examiner* — Erich A Leeser
(74) *Attorney, Agent, or Firm* — Finnegan, Henderson, Farabow, Garrett & Dunner, LLP

(57) ABSTRACT

New inhibitors of the p38 mitogen-activated protein kinase having the general formula (I) are disclosed herein, as well as processes for their preparation, pharmaceutical compositions comprising them, and their use in therapy.

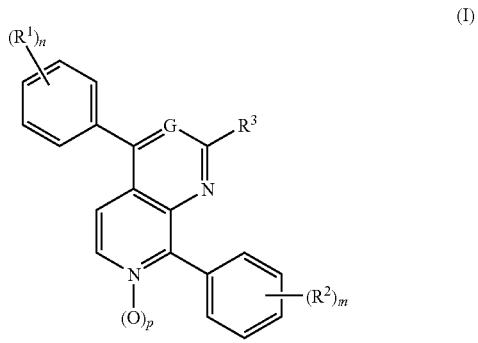

(I)

18 Claims, No Drawings

FOREIGN PATENT DOCUMENTS

| | | |
|---|---|---|
| WO | WO 2004/011470 A1 | 2/2004 |
| WO | WO 2004/014900 A1 | 2/2004 |
| WO | WO 2004/020438 A2 | 3/2004 |
| WO | WO 2004/020440 A1 | 3/2004 |
| WO | WO 2005/000232 A2 | 1/2005 |
| WO | WO 2005/018624 A2 | 3/2005 |
| WO | WO 2005/032551 A1 | 4/2005 |
| WO | WO 2005/070929 A1 | 8/2005 |
| WO | WO 2005/073219 A1 | 8/2005 |
| WO | WO 2005/121142 A1 | 12/2005 |
| WO | WO 2007/063925 A1 | 6/2007 |
| WO | WO 2007/098214 A1 | 8/2007 |
| WO | WO 2007/104664 A1 | 9/2007 |
| WO | WO 2008/017461 A1 | 2/2008 |
| WO | WO 2008/045393 A2 | 4/2008 |
| WO | WO 2008/107125 A1 | 9/2008 |
| WO | WO 2009/124692 A1 | 10/2009 |
| WO | WO 2009/132774 A1 | 11/2009 |
| WO | WO 2011/057757 A1 | 5/2011 |

OTHER PUBLICATIONS

Amato, J. S., et al., "Synthesis of 1-tert-Butyl-4-chlorpiperidine: generation of an N-tert-Butyl group by the reaction of a dimethyliminium salt with methylmagnesium chloride," The Journal of Organic Chemistry, 70(5):1930-1933 (2005).

Balaban, A. T., "Aminyloxides (nitroxides) from 1-hydroxy-2-indolinones," Tetrahedron, 30:739-744 (1974).

Bao, J. et al., "p38 MAP kinase inhibitors: metabolically stabilized piperidine-substituted quinolinones and naphthyridinones," Bioorganic & Medicinal Chemistry Letters, 16: 64-68 (2006).

Baxter, I. et al., "The oxidation of 5-arylsulphonamido-3,3-dimethyloxindoles and related compounds," Journal of the Chemical Society (C), pp. 952-955 (1971).

Beardmore, V. A., et al., "Generation and characterization of p38β (MAPK11) gene targeted mice," Molecular and Cellular Biology, 25(23):10454-10464 (2005).

Brancho, D., et al., "Mechanism of p38 MAP kinase activation in vivo," Genes & Development, 17:1969-1978 (2003).

Cheng, C., et al., "The friedlander synthesis of quinolines," Org. React., Chapter 2:37-201 (1982).

Dopp, D., "Substituenteneinflüsse auf die photocyclisierung von 1-tert-Butyl-2-nitrobenzolen," Liebigs Annalen der Chemie, pp. 554-563 (1979).

English Language Abstract for JP-203068 from esp@cenet, dated Dec. 13, 1982.

English Language Abstract for JP 1996-005887.

English Language Abstract for JP 10-79183.

English Language Abstract for JP 09-104638.

English Language Abstract for WO 1987/04928.

English Language Abstract for WO 1991/04974.

English Language Abstract for WO 1991/06545.

English Language Abstract for WO 2004/011470.

English Language Abstract for WO 2007/063925.

Fang, Cheng-Lin, et al., "Dimerization of a 3-substituted oxidindole at C-3 and Its application to the synthesis of (±)-folicanthine," Journal of the American Chemical Society, 116: 9480-9486 (1994).

Gavrin, L. K., et al., "Inhibition of Tpl2 kinase and TNF-α production with 1,7-naphthyridine-3-carbonitriles: synthesis and structure-activity relationships," Bioorganic & Medicinal Chemistry Letters, 15: 5288-5292 (2005).

Gilman, H., et al., "Some substituted Isoquinolines," Journal of American Chemical Society, 69(8):1946-1948 (1947).

Hale, K. K., et al., "Differential expression and activation of p38 mitogen-activated protein kinase α, β, γ, and δ in inflammatory cell lineages," The Journal of Immunology, 162: 4246-4252 (1999).

Hideshima, T., et al., "Targeting p38 MAPK inhibits multiple myeloma cell growth in the bone marrow milieu," Blood, 101(2):703-705 (2003).

Hildesheim, J., et al., "p38 Mitogen-activated protein kinase inhibitor protects the epidermis against the acute damaging effects of ultraviolet Irradiation by blocking apoptosis and inflammatory responses," The Journal of Investigative Dermatology, 122:497-502 (2004).

Hollenbach, E., et al., "Inhibition of RICK/Nuclear factor-κb and p38 signaling attenuates the inflammatory response in a murine model of crohn disease," The Journal of Biological Chemistry, 280(15):14981-14988 (2005).

International Search Report, PCT/EP2007/006981, mailed Oct. 18, 2007.

International Search Report, PCT/EP2009/0002783, mailed May 28, 2009.

International Search Report, PCT/EP2009/002458, mailed Jun. 3, 2009.

International Search Report, PCT/EP2010/006817, mailed May 2, 2011.

Jin, Shan-Xue, et al., "p38 Mitogen-activated protein kinase is activated after a spinal nerve ligation in spinal cord microglia and dorsal root ganglion neurons and contributes to the generation of neuropathic pain," The Journal of Neuroscience, 23(10):4017-4022 (2003).

Karp, G., et al., "Preparation and alkylation of regioisomeric tetrahydrophthalimide-substituted Indolin-2(3H)-ones," Journal of Heterocyclic Chemistry, 31:1513-1520 (1994).

Katsoulidis, E., et al., "Role of the p38 mitogen-activated protein kinase pathway in cytokine-mediated hematopoietic suppression in myelodysplastic syndromes," Cancer Research, 65(19):9029-9037 (2005).

Kotlyarov, A., et al., "MAPKAP Kinase 2 is essential for LPS-induced TNF-α biosynthesis," Nature Cell Biology, 1:94-97 (1999).

Kumar, S., et al., "p38 Map kinases: key signaling molecules as therapeutic targets for inflammatory diseases," Nature Reviews Drug Discovery, 2:717-726 (2003).

Kyriakis, J. M., et al., "Mammalian mitogen-activated protein kinase signal transduction pathways activated by stress and inflammation," Physiological Reviews, 81(2):807-869 (2001).

Lee, H. J., et al., "Biochemical and physiological effects of benzheterocycles and related compounds," Journal of Agricultural and Food Chemistry, 43: 2722-2727 (1995).

Lee, J. C., et al., "A protein kinase involved in the regulation of inflammatory cytokine biosynthesis," Nature, 372(22/29):739-746 (1994).

Lyga, J., et al., "Structural replacements for the benzoxazinone protox Inhibitors," Pesticide Science, 55: 281-287 (1999).

Miyaura, N., et al., "Palladium-catalyzed cross-coupling reactions of organoboron compounds," Chem. Rev., 95(7): 2457-2483 (1995).

Moran, D. B., et al., "Synthesis of (pyridinyl)-1,2,4-triazolo[4,3-a]pyridines," J. Heterocyclic Chem., 23:1071-1077 (1986).

Müller, C., et al., "Chiral Pyrrolo[2,3-d]pyrimidine and Pyrimido[4,5-b]indole derivatives: structure-activity relationships of potent, highly stereoselective $A_1$-adenosine receptor antagonists," Journal of Medicinal Chemistry, 39:2482-2491 (1996).

Negishi, E., et al., "Novel stereoselective alkenyl-aryl coupling via nickel-catalysed reaction of alkenylalanes with aryl halides," J.C.S. Chem. Comm.,pp. 596-597 (1976).

Nick, J. A., et al., "Selective suppression of neutrophil accumulation in ongoing pulmonary inflammation by systemic Inhibition of p38 mitogen-activated protein kinase," The Journal of Immunology, 169:5260-5269 (2002).

Notice of Allowance dated Nov. 8, 2010 for U.S. Appl. No. 12/376,499.

Office Action dated Aug. 2, 2010 for U.S. Appl. No. 12/376,499.

Office Action dated Oct. 28, 2011 for U.S. Appl. No. 12/529,490.

Pargellis, C., et al., "Inhibitors of p38 mitogen-activated protein kinase for the treatment of rheumatoid arthritis," Current Opinion in Investigational Drugs, 4(5): 566-571 (2003).

Patani, G. A., et al., "Bioisosterism: a rational approach in drug design," Chemical Reviews, ACS, 96(8):3147-3176 (1996).

Sabio, G., et al., "p38γ regulates the localisation of SAP97 in the cytoskeleton by modulating its interaction with GKAP," The EMBO Journal, 24(6):1134-1145 (2005).

Saccani, S., et al., "p38-dependent marking of inflammatory genes for increased NF-κB recruitment," Nature Immunology, 3(1): 69-75 (2002).

Santilli, A. A., et al., "7-Deazapurines v. synthesis and reactions of 7-amino-5,7-dihydro-4-methyl-2-phenyl-6H-pyrrolo[2,3-d]pyrimidin-6-one," Journal of Heterocyclic Chemistry, 12:1291-1293 (1975).

Schäfers, M., et al., "Tumor necrosis factor-α induces mechanical allodynia after spinal nerve ligation by activation of p38 MAPK in primary sensory neurons," The Journal of Neuroscience, 23(7): 2517-2521 (2003).

See, F., et al., "p38 MAP kinase as a therapeutic target in cardiovascular disease," Drug Discovery Today: Therapeutic Strategies, 1(2):149-154 (2004).

Shi, Y., et al., "In the cellular garden of forking paths: how p38 MAPKs signal for downstream assistance," Biol. Chem., 383(10):1519-1536 (2002).

Tamura, K., et al., "Requirement for p38α in erythropoietin expression: a role for stress kinases in erythropoiesis," Cell, 102:221-231 (2000).

Tsuda, M., et al., "Activation of p38 mitogen-activated protein kinase in spinal hyperactive microglia contributes to pain hypersensitivity following peripheral nerve injury," GLIA, 89:89-95 (2004).

Underwood, D. C., et al., "SB 239063, a p38 MAPK inhibitor, reduces neutrophilia, inflammatory cytokines, MMP-9, and fibrosis in lung," Am. J. Physiol. Lung Cell Mol. Physiol., 279:L895-L902 (2000).

Waetzig, G. H., et al., "p38 Mitogen-activated protein kinase Is activated and linked to TNF-α signaling in inflammatory bowel disease," The Journal of Immunology, 168:5342-5351 (2002).

Wang, X. S., et al., "Molecular cloning and characterization of a novel p38 mitogen-activated protein kinase," The Journal of Biological Chemistry, 272(38):23668-23674 (1997).

Zhou, Z., et al., "TNFR-induced the NF-kB, but not the ERK, p38MAPK or JNK activation, mediates TNF-induced ICAM-1 and VCAM-1 expression on endothelial cells," Cellular Signalling, 19:1238-1248 (2007).

* cited by examiner

4,8-DIPHENYL-POLYAZANAPHTHALENE DERIVATIVES

This is a national stage filing under 35 U.S.C. §371 of International Application No. PCT/EP2008/003357, filed on Apr. 25, 2008, which claims priority to Spanish Patent Application No. P200701132, filed Apr. 26, 2007. The contents of both applications are incorporated herein by reference.

The present invention relates to new inhibitors of the p38 mitogen-activated protein kinase.

MAP kinases are evolutionary conserved enzymes translating membrane signals into gene expression responses. In mammals, four MAPK families can be distinguished: extracellular signal-related kinases (ERK1/2), Jun amino terminal kinases (JNK1/2/3), p38 proteins (alpha, beta, gamma and delta) and ERK5. The regulation of these proteins is exerted by a three-tier cascade composed of MAPK, MAPK kinase, and MAPK kinase kinase.

p38 MAPK was originally identified as the target of CSAIDs (cytokine suppressive anti-inflammatory drugs), having a central role in the signal transduction pathway leading to the production of TNF-alpha and other cytokines (Lee et al, 1984). p38 is activated by phosphorylation in Thr and Tyr by either MKK3, MKK4, or MKK6 (Kyriakis and Avruch, 2001) in response to stress and pro-inflammatory stimuli. In turn, p38 phosphorylates its effectors in Ser and Thr residues, namely protein kinases phosphatases and transcription factors, such as ATF-2, MEF2, MAPKAPK2, MSK1/2 or MNK1/2. Altogether this activation cascade results in control of gene expression through four different mechanisms: transcription factor activation; mRNA stabilization; mRNA translation; and histone phosphorylation at NF-kB binding sites in chromatin (Shi and Gaestel, 2002; Sacanni et al, 2001).

There are four different p38 isoforms encoded by separate genes: p38 alpha, beta, gamma and delta, each one showing a distinct tissue expression pattern. As assessed by mRNA and protein levels (Beardmore et al, 2005; Wang et al, 1997), p38 alpha and beta are ubiquitously expressed, with p38 beta expression being more relevant in CNS tissues (brain, cortex, cerebellum, hippocampus, etc). The expression of p38 gamma is more prominent in skeletal muscle while p38 delta localizes mainly in heart, kidney, lung and adrenal gland. At the cellular level, p38 alpha and delta seem to be the most relevant isoforms in immune cells (monocytes, macrophages, neutrophils and T cells) (Hale et al, 1999). Pharmacological inhibition with specific p38alpha/beta inhibitors as well as gene targeting studies have indicated that p38alpha is the isoform regulating inflammatory responses most probably through its downstream substrate MAPKAP-K2 (Kotlyarov et al, 1999). Likewise, this isoform is necessary in early embryonic development as p38alpha KO (knock-out) mice die in embryonic day 12.5 due to placental insufficiency and vascular defects (Allen et al, 2000; Tamura et al, 2000; Adams et al, 2000), a phenotype that is also reproduced in the MKK3/MKK6 double KO mice (Brancho et al, 2003). In contrast, p38 beta, gamma and delta knock-out mice do not show any developmental deficiencies (Beardmore et al 2005; Sabio et al, 2005). p38 beta KO mice appear to respond similarly to pro-inflammatory stimuli (LPS) as wild type controls, indicating that this isoform does not have a role in inflammation (Beardmore et al 2005).

The contribution of the p38MAPK pathway to inflammation has been studied both in vitro and in vivo by employing different chemical series of p38 inhibitors (Pargellis and Regan, 2003; Kumar et al, 2003). The most widely used inhibitor molecule, SB203580, is, in fact, a dual p38alpha/beta inhibitor. Inhibition of p38 abrogates the release of TNF-alpha as well as other pro-inflammatory cytokines such as IL-1, IL-6, and IL-8, in PBMC, whole blood, or the human monocytic cell line THP-1.

By virtue of the involvement of p38 in TNFalpha production, inhibitors of p38 have been tested in animal models of diseases in which TNFalpha has a pathophysiological role. p38 inhibition decreases murine collagen-induced arthritis and rat adjuvant-induced arthritis severity (Pargellis and Regan, 2003). Furthermore, p38 inhibitors also improve bone resorption in animal models of arthritis, probably due to the implication of p38 MAPK in the differentiation of osteoclasts. p38 inhibition attenuates the inflammatory response in a murine model of Crohn's disease and diminishes TNF-alpha production in human Crohn's disease patient biopsies (Hollenbach et al 2005; Waetzig et al, 2002). Due to the exclusive usage of the p38 pathway by neutrophils, p38 has also been considered a target for chronic obstructive pulmonary disease (COPD) (Nick et al, 2002). p38 inhibition reduces neutrophilia, inflammatory cytokines, MMP-9 and fibrosis in lung (Underwood et al, 2000). In skin models of irradiation, inhibition of p38 protects the epidermis against acute ultraviolet radiation exposure by blocking apoptosis and inflammatory responses (Hildesheim et al, 2004). p38 inhibition also reverses hematopoietic defects in bone marrow from patients with myelodysplastic syndromes, in which TNF-alpha overproduction has a pathophysiological role (Katsoulidis et al, 2005).

In hematopoietic malignancies, a study has shown that p38 inhibitors can block the proliferation of multiple myeloma cells by inhibiting the production of IL-6 and VEGF in bone marrow stromal cells (Hideshima et al, 2002).

p38 is involved in key cellular mechanisms such as apoptosis, fibrosis and cellular hypertrophy, which are common to cardiac and vascular pathologies. Pharmacological inhibition of p38 has proven useful in improving ischemia-reperfusion injury, cerebral focal ischemia, acute coronary syndrome, chronic heart failure and post-myocardial infarction remodelling (See et al, 2004).

Experimental inhibition of p38 has been reported effective in reducing pain in animal models of neuropathy that rely on COX-2 expression and TNF-alpha production by glial cells (Schafers et al, 2003; Jin et al, 2003; Tsuda et al, 2004).

Therefore, the compounds of the invention may be useful in the prophylaxis or treatment of any disease or disorder in which p38 kinase plays a role including conditions caused by excessive or unregulated pro-inflammatory cytokine production including for example excessive or unregulated TNF, IL-1, IL-6 and IL-8 production in a human, or other mammal. The invention extends to such a use and to the use of the compounds for the manufacture of a medicament for treating such cytokine-mediated diseases or disorders. Further, the invention extends to the administration to a human an effective amount of a p38 inhibitor for treating any such disease or disorder.

Diseases or disorders in which p38 kinase plays a role either directly or via pro-inflammatory cytokines including the cytokines TNF, IL-1, IL-6 and IL-8 include without limitation autoimmune diseases, immune and inflammatory diseases, destructive bone disorders, neoplastic disorders, neurodegenerative disorders, viral diseases, infectious diseases, cardiovascular diseases, angiogenesis-related disorders, and pain-related disorders.

Autoimmune diseases which may be prevented or treated include but are not limited to psoriasis, rheumatoid arthritis, psoriatic arthritis, ankylosing spondilytis, Reiter's syndrome, fibromyalgia, inflammatory bowel disease such as ulcerative colitis and Crohn's disease, multiple sclerosis, diabetes, glomerulonephritis, systemic lupus erythematosus, scleroderma, chronic thyroiditis, Grave's disease, hemolytic anemia, autoimmune gastritis, autoimmune neutropenia, thrombocytopenia, autoimmune chronic active hepatitis, myasthenia gravis, or Addison's disease.

Immune and inflammatory diseases which may be prevented or treated include but are not limited to asthma, COPD, respiratory distress syndrome, acute or chronic pancreatitis, graft versus-host disease, Behcet syndrome, inflammatory eye conditions such as conjunctivitis and uveitis, psoriasis, contact dermatitis, atopic dermatitis, sarcoidosis, gout, pyresis, transplant rejection, allergic rhinitis, allergic conjunctivitis, Cardiovascular diseases which may be prevented or treated include but are not limited to ischemia-reperfusion injury, cerebral focal ischemia, acute coronary syndrome, congestive heart failure, cardiomyopathy, myocarditis, atherosclerosis, vasculitis and restenosis.

Destructive bone disorders which may be prevented or treated include but are not limited to osteoporosis, osteoarthritis and multiple myeloma-related bone disorder.

Neoplastic disorders which may be prevented or treated include but are not limited to solid tumors such as Kaposi's sarcoma, metastatic melanoma, and hematopoietic malignancies such as acute or chronic myelogenous leukemia and multiple myeloma.

Neurodegenerative diseases which may be prevented or treated include but are not limited to Parkinson's disease, Alzheimer's disease, neurodegenerative disease caused by traumatic injury, or Huntington's disease.

Viral diseases which may be prevented or treated include but are not limited to acute hepatitis infection (including hepatitis A, hepatitis B and hepatitis C), HIV infection, Epstein-Barr infection, CMV retinitis, SARS or avian influenza A infection.

Infectious diseases which may be prevented or treated include but are not limited to sepsis, septic shock, endotoxic shock, Gram negative sepsis, toxic shock syndrome, Shigellosis, or cerebral malaria.

Angiogenesis-related disorders which may be prevented or treated include but are not limited to hemangiomas, ocular neovascularization, macular degeneration or diabetic retinopathy.

Pain-related disorders which may be prevented or treated include but are not limited to neuropathic pain (such as diabetic neuropathy, post-herpetic or trigeminal neuralgia), cancer-related pain, chronic pain (such as lower back pain syndrome), and inflammatory pain.

Other miscellaneous diseases or disorders which may be prevented or treated include but are not limited to myelodysplastic syndrome, cachexia, endometriosis, acute skin injuries such as sunburn, and wound healing.

In view of the physiological effects mediated by inhibition of the p38 mitogen-activated protein kinase, several compounds have been recently disclosed for the treatment or prevention of rheumatoid arthritis, ischemia-reperfusion injury, cerebral focal ischemia, acute coronary syndrome, COPD, Crohn's disease, irritable bowel syndrome, adult respiratory distress syndrome, osteoporosis, neurodegenerative diseases such as Alzheimer's disease, rheumatoid spondylitis, psoriasis, atherosclerosis, osteoarthritis, multiple myeloma. See for example WO 99/01449, WO 00/63204, WO 01/01986, WO 01/29042, WO 02/046184, WO 02/058695, WO 02/072576, WO 02/072579, WO 03/008413, WO 03/033502, WO 03/087087, WO 03/097062, WO 03/103590, WO 2004/010995, WO 2004/014900, WO 2004/020438, WO 2004/020440, WO 2005/018624, WO 2005/032551, WO 2005/073219.

It has now been found that certain 1,7-naphthyridine derivatives are novel potent inhibitors of the p38 mitogen-activated protein kinase and can therefore be used in the treatment or prevention of these diseases.

Further objectives of the present invention are to provide a method for preparing said compounds; pharmaceutical compositions comprising an effective amount of said compounds; the use of the compounds in the manufacture of a medicament for the treatment of pathological conditions or diseases susceptible of being improved by inhibition of the p38 mitogen-activated protein kinase; and methods of treatment of pathological conditions or diseases susceptible to amelioration by inhibition of the p38 mitogen-activated protein kinase comprising the administration of the compounds of the invention to a subject in need of treatment.

Thus, the present invention is directed to new 4,8-diphenyl-polyazanaphthalene derivatives of formula (I) for use in the treatment of a human or animal body

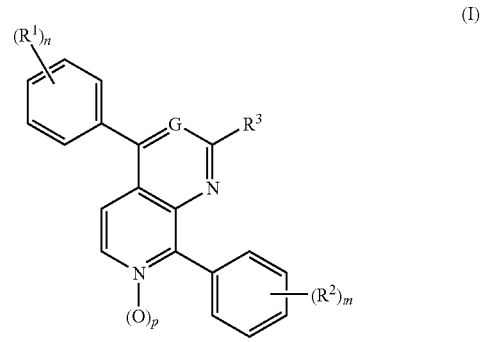

wherein:
G represents a nitrogen atom or a =CH— group
$R^1$ represents a halogen atom, a $C_{1-4}$ alkyl group optionally substituted by one, two or three halogen atoms, or a $C_{1-4}$ alkoxy group.
$R^2$ represents a halogen atom or a group selected from hydroxy, $C_{1-4}$ alkyl, $C_{1-4}$ alkoxy, $C_{1-4}$ alkylthio, $C_{1-4}$ alkoxy-$C_{1-4}$ alkoxy, morpholin-$C_{1-4}$ alkoxy, $C_{1-4}$ alkanesulfonamide and ($C_{1-4}$ alkoxy-$C_{1-4}$ alkyl)carbamoyl.
$R^3$ is selected from the groups consisting of a hydrogen atom, a hydroxy group, —$NR^4R^5$, —NH—$(CH_2)_q$—$NR^4R^5$, —S—$(CH_2)_q$— $NR^4R^5$, —O—$(CH_2)_q$—$NR^4R^5$, —$NHS(O)_2R^4$, —$NHCOR^4$, —$NHC(O)OR^4$, or $COOR^4$ groups.
$R^4$ and $R^5$ are independently selected from the group consisting of a hydrogen atom and $C_{1-4}$ alkyl group
n is an integer from 0 to 4
m is an integer from 0 to 4
p has the value of zero or one;
q is an integer from 1-4.
and pharmaceutically acceptable salts thereof.
with the proviso that when G is a =CH— group, $R^3$ can not be a hydrogen atom.

To avoid any confusion, it is clarified that in the above formula when p has the value of zero the compounds of formula (I) are 1,7-naphthyridines or pyrido[3,4-d]pyrimidines and when p has the value of one the compounds are 1,7-naphthyridine 7-oxides or pyrido[3,4-d]pyrimidines 7-oxides.

When $R^3$ is a hydroxy group the compounds of formula (I) may adopt its tautomeric form of formula (Ia):

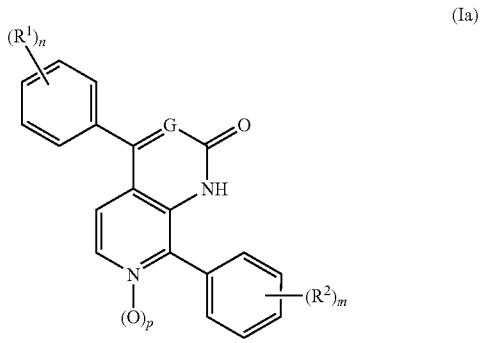

(Ia)

The present invention is also directed to new compounds of the formula (I) per se, and pharmaceutically acceptable salts thereof, wherein each of G, $R^1$, $R^2$, $R^3$, $R^4$, $R^5$, n, m, p and q is as herein defined, with the proviso that when G is a —CH— group, $R^3$ cannot be a hydroxy group.

As used herein the term alkyl embraces optionally substituted, linear or branched radicals having 1 to 4, preferably 1 to 3 and more preferably 1 to 2 carbon atoms. The substituents in said alkyl groups are selected from halogen atoms.

Examples include methyl, ethyl, n-propyl, i-propyl, n-butyl, sec-butyl and tert-butyl radicals.

As used herein, the term alkoxy embraces optionally substituted, linear or branched oxy-containing radicals each having alkyl portions of 1 to 4, preferably 1 to 3 and more preferably 1 to 2 carbon atoms. The substituents in said alkoxy groups are selected from halogen atoms and hydroxyl groups.

Preferred alkoxy radicals include methoxy, ethoxy, n-propoxy, i-propoxy, n-butoxy, sec-butoxy, t-butoxy, trifluoromethoxy, difluoromethoxy, hydroxymethoxy, 2-hydroxyethoxy or 2-hydroxypropoxy.

As used herein, the term alkylthio embraces radicals containing an optionally substituted, linear or branched alkyl radicals of 1 to 4, preferably 1 to 3 and more preferably 1 to 2 carbon atoms. The substituents in said alkylthio groups are selected from halogen atoms.

Preferred optionally substituted alkylthio radicals include methylthio, ethylthio, n-propylthio, i-propylthio, n-butylthio, sec-butylthio, t-butylthio, trifluoromethylthio, difluoromethylthio, hydroxymethylthio, 2-hydroxyethylthio or 2-hydroxypropylthio.

As used herein, the term heteroaryl radical (also named aromatic heterocycle) embraces typically a 5- to 14-membered ring system comprising at least one heteroaromatic ring and containing at least one heteroatom selected from O, S and N. A heteroaryl radical may be a single ring or two or more fused rings wherein at least one ring contains a heteroatom.

Examples include pyridyl, pyrazinyl, pyrimidinyl, pyridazinyl, furyl, oxadiazolyl, oxazolyl, imidazolyl, thiazolyl, thiadiazolyl, thienyl, pyrrolyl, pyridinyl, benzothiazolyl, indolyl, indazolyl, purinyl, quinolyl, isoquinolyl, phthalazinyl, naphthyridinyl, quinoxalinyl, quinazolinyl, quinolizinyl, cinnolinyl, triazolyl, indolizinyl, indolinyl, isoindolinyl, isoindolyl, imidazolidinyl, pteridinyl and pyrazolyl radicals. Pyridyl, thienyl, furanyl, pyridazinyl, pyrimidinyl and quinolyl radicals are preferred.

When a heteroaryl radical carries 2 or more substituents, the substituents may be the same or different.

As used herein, some of the atoms, radicals, moieties, chains or cycles present in the general structures of the invention are "optionally substituted". This means that these atoms, radicals, moieties, chains or cycles can be either unsubstituted or substituted in any position by one or more, for example 1, 2, 3 or 4, substituents, whereby the hydrogen atoms bound to the unsubstituted atoms, radicals, moieties, chains or cycles are replaced by chemically acceptable atoms, radicals, moieties, chains or cycles. When two or more substituents are present, each substituent may be the same or different.

As used herein, the term halogen atom embraces chlorine, fluorine, bromine or iodine atoms typically a fluorine, chlorine or bromine atom, most preferably chlorine or fluorine. The term halo when used as a prefix has the same meaning.

As used herein, the term pharmaceutically acceptable salt embraces salts with a pharmaceutically acceptable acid or base. Pharmaceutically acceptable acids include both inorganic acids, for example hydrochloric, sulphuric, phosphoric, diphosphoric, hydrobromic, hydroiodic and nitric acid and organic acids, for example citric, fumaric, maleic, malic, mandelic, ascorbic, oxalic, succinic, tartaric, benzoic, acetic, methanesulphonic, ethanesulphonic, benzenesulphonic or p-toluenesulphonic acid. Pharmaceutically acceptable bases include alkali metal (e.g. sodium or potassium) and alkali earth metal (e.g. calcium or magnesium) hydroxides and organic bases, for example alkyl amines, arylalkyl amines and heterocyclic amines.

Other preferred salts according to the invention are quaternary ammonium compounds wherein an equivalent of an anion (X—) is associated with the positive charge of the N atom. X— may be an anion of various mineral acids such as, for example, chloride, bromide, iodide, sulphate, nitrate, phosphate, or an anion of an organic acid such as, for example, acetate, maleate, fumarate, citrate, oxalate, succinate, tartrate, malate, mandelate, trifluoroacetate, methanesulphonate and p-toluenesulphonate. X— is preferably an anion selected from chloride, bromide, iodide, sulphate, nitrate, acetate, maleate, oxalate, succinate or trifluoroacetate. More preferably X— is chloride, bromide, trifluoroacetate or methanesulphonate.

As used herein, an N-oxide is formed from the tertiary basic amines or imines present in the molecule, using a convenient oxidising agent.

When $R^3$ is a $NHCOR^4$ group, then $R^4$ is typically a $C_{1-4}$ alkyl group.

In one embodiment of the present invention the compounds are 4,8-diphenyl-polyazanaphthalene 7-N-oxides, i.e. compounds of formula (I) wherein p has a value of 1.

In another embodiment of the present invention, in the formula (I), n is 1 or 2 and each $R^1$ independently represents an halogen atom or a $C_{1-4}$ alkyl group. In a more specific embodiment at least one group $R^1$, in the formula (I), is at an ortho position with respect to the carbon atom through which the phenyl group is attached to the naphtyridine or pyrido[3,4-d]pyrimidine core. In yet a more specific embodiment $R^1$, in the formula (I), represents a halogen atom, preferably selected from chlorine or fluorine atoms. In a further more specific embodiment, in the formula (I), n is 2 and both $R^1$ groups are identical.

In another embodiment of the present invention, in the formula (I), m is 1 or 2 and each $R^2$ independently represents an halogen atom or a $C_{1-4}$ alkyl group. In a more specific embodiment at least one group $R^2$, in the formula (I), is at an ortho position with respect to the carbon atom through which the phenyl group is attached to the naphtyridine or pyrido[3,4-d]pyrimidine core. In yet a more specific embodiment, in the formula (I), m is 2 and the two groups $R^2$ are at an ortho position with respect to the carbon atom through which the phenyl group is attached to the naphtyridine or pyrido[3,4-d]pyrimidine core. In still a more specific embodiment both $R^2$ groups, in the formula (I), are halogen atoms, preferably they are identical and are selected from chlorine or fluorine atoms.

In another embodiment of the present invention $R^3$, in the formula (I), represents a hydrogen atom or is selected from the group consisting of a hydroxy, —NR$^4$R$^5$, —NH—(CH$_2$)$_q$—NR$^4$R$^5$ and —NHS(O)$_2$R$^4$ group, wherein R$^4$ and R$^5$ independently represent a hydrogen atom or a methyl group and q has a value from 2 to 4.

In a still another embodiment of the present invention, R$^3$, in the formula (I), is selected from the group consisting of —NR$^4$R$^5$, —NH—(CH$_2$)$_q$—NR$^4$R$^5$ wherein R$^4$ and R$^5$ independently represent a hydrogen atom or a methyl group and q has a value of 2

In a more specific embodiment of the present invention R$^3$, in the formula (I), represents —NH$_2$ group.

Particular individual compounds of the invention include:
4-(2,4-Difluorophenyl)-8-(2,6-difluorophenyl)-1,7-naphthyridine-2-carboxylic acid
4-(2,4-Difluorophenyl)-8-(2,6-difluorophenyl)-1,7-naphthyridine-2-carboxylic acid 7-oxide
4-(2,4-Difluorophenyl)-8-(2,6-difluorophenyl)-1,7-naphthyridin-2-amine
4-(2,4-Difluorophenyl)-8-(2,6-difluorophenyl)-1,7-naphthyridin-2-amine 7-oxide
4-(2,4-Difluorophenyl)-8-(2-methylphenyl)-1,7-naphthyridin-2(1H)-one
4-(2,4-Difluorophenyl)-8-(2-methylphenyl)-1,7-naphthyridin-2(1H)-one 7-oxide
4-(2-Chloro-4-fluorophenyl)-8-(2,6-difluorophenyl)-1,7-naphthyridin-2(1H)-one
4-(2-Chloro-4-fluorophenyl)-8-(2,6-difluorophenyl)-1,7-naphthyridin-2(1H)-one 7-oxide
N'-[4-(2-Chloro-4-fluorophenyl)-8-(2,6-difluorophenyl)-1,7-naphthyridin-2-yl]-N,N-dimethylethane-1,2-diamine
N'-[4-(2-Chloro-4-fluorophenyl)-8-(2,6-difluorophenyl)-7-oxido-1,7-naphthyridin-2-yl]-N,N-dimethylethane-1,2-diamine
4-(2-Chloro-4-fluorophenyl)-8-(2,6-dichlorophenyl)-1,7-naphthyridin-2(1H)-one
4-(2-Chloro-4-fluorophenyl)-8-(2,6-dichlorophenyl)-1,7-naphthyridin-2(1H)-one 7-oxide
4-(2-Chloro-4-fluorophenyl)-8-(2,6-dichlorophenyl)-1,7-naphthyridin-2-amine
4-(2-Chloro-4-fluorophenyl)-8-(2,6-dichlorophenyl)-1,7-naphthyridin-2-amine 7-oxide
4-(2-Chlorophenyl)-8-(2,6-difluorophenyl)-1,7-naphthyridin-2(1H)-one
4-(2-Chlorophenyl)-8-(2,6-difluorophenyl)-1,7-naphthyridin-2(1H)-one 7-oxide
4-(2-Chlorophenyl)-8-(2,6-dichlorophenyl)-1,7-naphthyridin-2(1H)-one
4-(2-Chlorophenyl)-8-(2,6-dichlorophenyl)-1,7-naphthyridin-2(1H)-one 7-oxide
4-(2-Chlorophenyl)-8-(2,6-dichlorophenyl)-N-methyl-1,7-naphthyridin-2-amine 7-oxide
4-(2-Chlorophenyl)-8-(2,6-dichlorophenyl)-N,N-dimethyl-1,7-naphthyridin-2-amine 7-oxide
N-[4-(2-Chlorophenyl)-8-(2,6-dichlorophenyl)-7-oxido-1,7-naphthyridin-2-yl]methanesulfonamide
4-(2-Chlorophenyl)-8-(2,6-dichlorophenyl)-1,7-naphthyridin-2-amine 7-oxide
Methyl 4-(2-chlorophenyl)-8-(2,6-dichlorophenyl)-1,7-naphthyridine-2-carboxylate 7-oxide
4-(2-Chlorophenyl)-8-(2,6-dichlorophenyl)-1,7-naphthyridine-2-carboxylic acid 7-oxide
4-(2-Chloro-4-fluorophenyl)-8-(2,6-difluorophenyl)pyrido[3,4-d]pyrimidine
4-(2-Chloro-4-fluorophenyl)-8-(2,6-difluorophenyl)pyrido[3,4-d]pyrimidine 7-oxide
4-(2-Chloro-4-fluorophenyl)-8-(2,6-difluorophenyl)pyrido[3,4-d]pyrimidin-2-amine
4-(2-Chloro-4-fluorophenyl)-8-(2,6-difluorophenyl)pyrido[3,4-d]pyrimidin-2-amine 7-oxide
4-(2-Chloro-4-fluorophenyl)-8-(2,6-dichlorophenyl)pyrido[3,4-d]pyrimidine
4-(2-Chloro-4-fluorophenyl)-8-(2,6-dichlorophenyl)pyrido[3,4-d]pyrimidine 7-oxide
4-(2-Chloro-4-fluorophenyl)-8-(2,6-dichlorophenyl)pyrido[3,4-d]pyrimidin-2-amine
4-(2-Chloro-4-fluorophenyl)-8-(2,6-dichlorophenyl)pyrido[3,4-d]pyrimidin-2-amine 7-oxide
4-(2,4-Difluorophenyl)-8-(2,6-difluorophenyl)pyrido[3,4-d]pyrimidin-2-amine
4-(2,4-Difluorophenyl)-8-(2,6-difluorophenyl)pyrido[3,4-d]pyrimidin-2-amine 7-oxide Of outstanding interest are:
4-(2,4-Difluorophenyl)-8-(2,6-difluorophenyl)-1,7-naphthyridin-2-amine 7-oxide
N'-[4-(2-Chloro-4-fluorophenyl)-8-(2,6-difluorophenyl)-7-oxido-1,7-naphthyridin-2-yl]-N,N-dimethylethane-1,2-diamine
4-(2-Chloro-4-fluorophenyl)-8-(2,6-dichlorophenyl)-1,7-naphthyridin-2-amine 7-oxide
4-(2-Chlorophenyl)-8-(2,6-dichlorophenyl)-1,7-naphthyridin-2-amine 7-oxide
4-(2-Chloro-4-fluorophenyl)-8-(2,6-difluorophenyl)pyrido[3,4-d]pyrimidin-2-amine 7-oxide
4-(2-Chloro-4-fluorophenyl)-8-(2,6-dichlorophenyl)pyrido[3,4-d]pyrimidin-2-amine 7-oxide
4-(2,4-Difluorophenyl)-8-(2,6-difluorophenyl)pyrido[3,4-d]pyrimidin-2-amine 7-oxide According to a further feature of the present invention, compounds of general formula (I) wherein G is =CH— and R$^3$ is OH group are prepared following the synthetic scheme illustrated in FIG. 1.

FIGURE 1

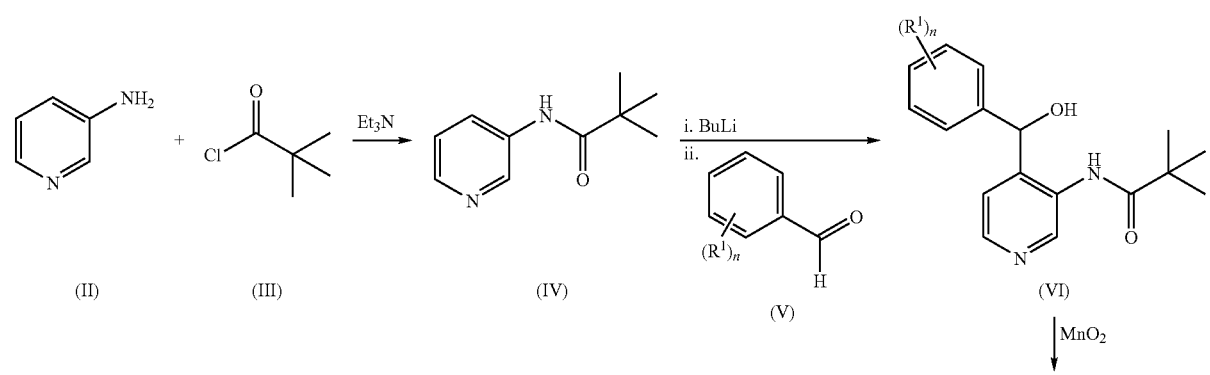

-continued

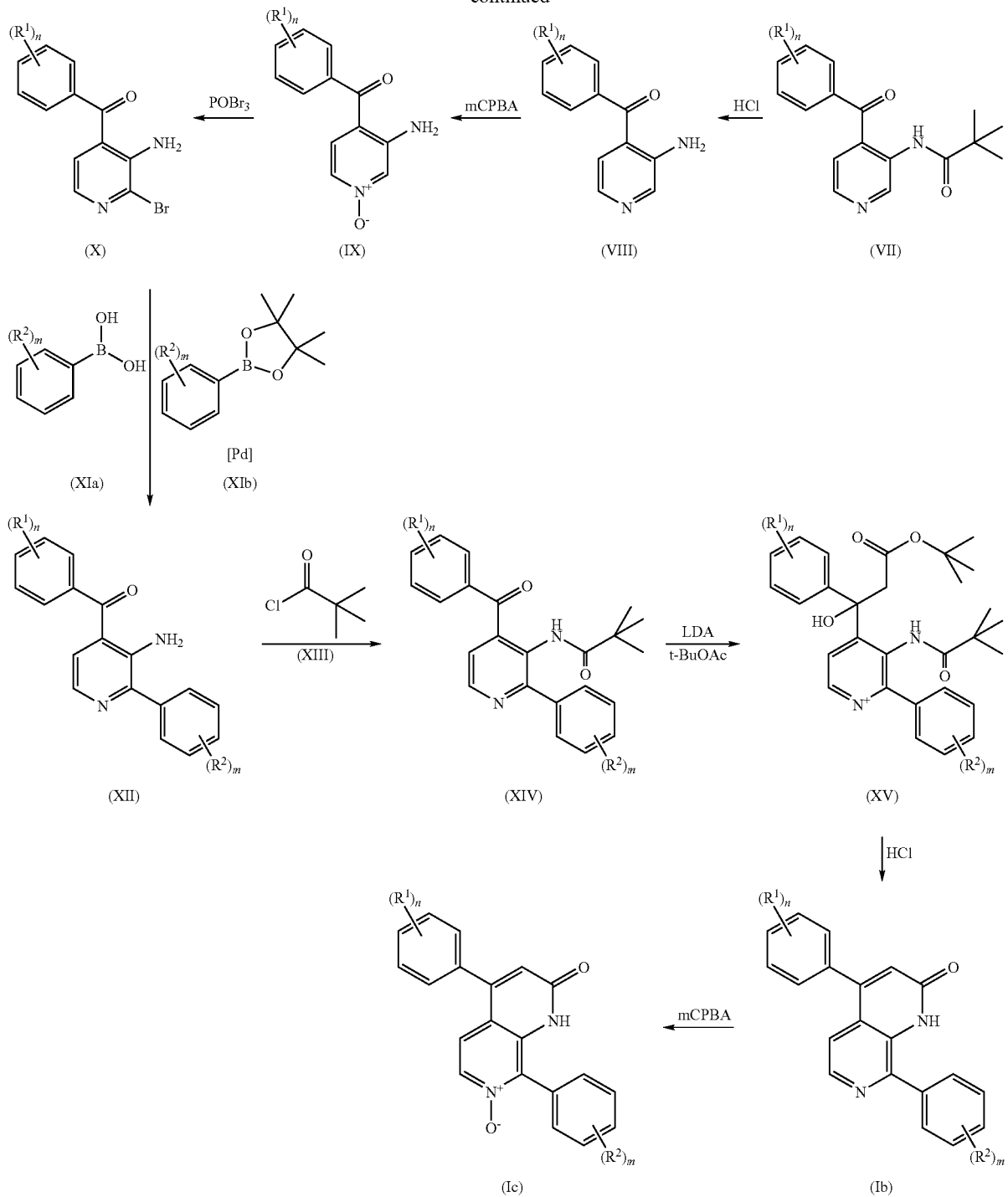

Reaction of 3-aminopyridine (II) with an acyl chloride (III) such as pivaloyl chloride in the presence of a base such as triethylamine, or diisopropylethylamine, using an halogenated solvent such as dichloromethane or an ether solvent such as dioxane at a temperature from 0° C. to 110° C. yields compound of formula (IV).

Compounds of formula (VI) can be obtained by lithiation of the compounds of formula (IV) with a solution of BuLi in hexanes, possibly in the presence of a cosolvent such as N,N,N',N'-tetramethylethane-1,2-diamine and subsequent addition of the corresponding aldehydes of formula (V) at a temperature from −78° C. to room temperature.

Oxidation of the alcohol compound of formula (VI) with an oxidizing agent such as manganese dioxide, Dess-Martin periodinane, tetrapropyl-ammonium perruthenate or pyridinium chlorochromate, preferably with manganese dioxide in an halogenated solvent such as chloroform at a temperature from room temperature to the boiling point of the solvent yields the compounds of formula (VII).

Subsequent hydrolysis of the pivaloylamide group in compounds of formula (VII) in acidic conditions such as treatment with HCl 5N using a solvent miscible with water such as ethanol at a temperature from 100° C. to 150° C. yields the aminopyridine of formula (VIII).

Subsequent oxidation of the aminopyridine of formula (VIII) with an oxidizing agent such as Oxone®, magnesium monoperoxyphthalate hexahydrate, hydrogen peroxide or meta-chloroperbenzoic acid, preferably with meta-chloroperbenzoic in an halogenated solvent such as dichloromethane and a temperature ranging from 0° C. to the boiling point of the solvent, yields the pyridine N-oxide of formula (IX).

The intermediate of formula (X) may be obtained by reacting the pyridine N-oxide of formula (IX) with phosphorus oxybromide neat or in an halogenated solvent such as dichloromethane at a temperature from 60° C. to 140° C.

The compounds of formula (XII) may be obtained by coupling a bromoderivative of formula (X) with the corresponding boronic acids (XIa) or boronates of formula (XIb) using Suzuki reactions (Miyaura, N.; Suzuki, A. Chem. Rev. 1995, 95, 2457). These reactions may be catalyzed by a palladium catalyst such as [1,1'-bis(diphenylphosphino)-ferrocene] dichloropalladium (II) complex with dichloromethane (1:1), tetrakis(triphenylphosphine)-palladium(0), bis(triphenylphosphine)palladium(II) chloride or tris(dibenzylideneacetone)-dipalladium(0) in an aprotic organic solvent such as dioxane, toluene, DMF or 1,2-dimethoxyethane and in the presence of a base such as cesium carbonate, sodium carbonate or potassium phosphate at a temperature from 80° C. to 140° C.

In the particular case where m is 2 and the groups $R^2$ are both in the ortho position and selected from alkyl groups, alkoxy groups or halogens the bromoderivative of formula (X) may be coupled with the corresponding boronic acid or boronate by a Suzuki reaction (Miyaura, N.; Suzuki, A. Chem. Rev. 1995, 95, 2457) using a palladium catalyst such as tris(dibenzylideneacetone)dipalladium(0) in the presence of a ligand such as 2-(dicyclohexylphosphino)-2',6'-dimethoxy-1-t-biphenyl (S-PHOS) and a base such as potassium phosphate, and in a solvent such as toluene at a temperature from 80° C. to 140° C. to yield the compound of formula (XII).

In the particular case where m is 2 and the two $R^2$ groups are fluorine atoms, the bromoderivative (X) may be coupled with the corresponding 1,3-difluorobenzene by a Negishi reaction (Negishi, E.-I.; Baba, S. J. Chem. Soc., Chem. Commun. 1976, 596) to yield the compound (XII). In this reaction, the first step is the lithiation of 1,3-difluorobenzene by treatment with a base such as BuLi at −78° C. using THF as solvent, afterwards a transmetalation step is carried out by treatment of the corresponding organolithium derivative with zinc dichloride at −50° C. and finally, the resulting organozinc is coupled with the bromoderivative of formula (III) using a palladium catalyst such as tetrakis(triphenylphosphine)palladium(0), bis(triphenylphosphine)-palladium(II) chloride or tris(dibenzylideneacetone)dipalladium(0) at a temperature between room temperature and the boiling point of the solvent.

Reaction of 3-aminopyridine of formula (XII) with an acyl chloride (III) such as pivaloyl chloride in the presence of a base such as triethylamine, or diisopropylethylamine, using an halogenated solvent such as dichloromethane or an ether solvent such as dioxane at a temperature from 0° C. to 110° C. yields compound of formula (XIV).

Compounds of formula (XV) can be obtained by addition of the lithium enolate of an alkyl acetate such as tert-butyl acetate to intermediate compound (XIV) in a solvent such as THF at a temperature between −78° C. and room temperature.

Such lithium enolates can be obtained by procedures well known in the literature using a base such as LDA.

Reaction of compounds (XV) with organic or inorganic acids such as aqueous 3M HCl at a temperature ranging from room temperature to 110° C. yields naphthyridones derivatives of formula (Ib).

Naphthyridinones derivatives of formula (Ib) can react with an oxidising agent such as Oxone®, magnesium monoperoxyphthalate hexahydrate, hydrogen peroxide or meta-chloroperbenzoic acid, preferably with meta-chloroperbenzoic acid in a halogenated solvent such as dichloromethane and a temperature from 0° C. to the boiling point of the solvent, to yield compounds of formula (Ic).

The present invention also provides a process, following the synthetic scheme illustrated in FIG. 2, for the preparation of compounds of formula (I) wherein G is =CH— and $R^3$ is selected from the group consisting of —NR$^4$R$^5$, —NH—(CH$_2$)$_q$—NR$^4$R$^5$, —S—(CH$_2$)$_q$—NR$^4$R$^5$, —O—(CH$_2$)$_q$—NR$^4$R$^5$

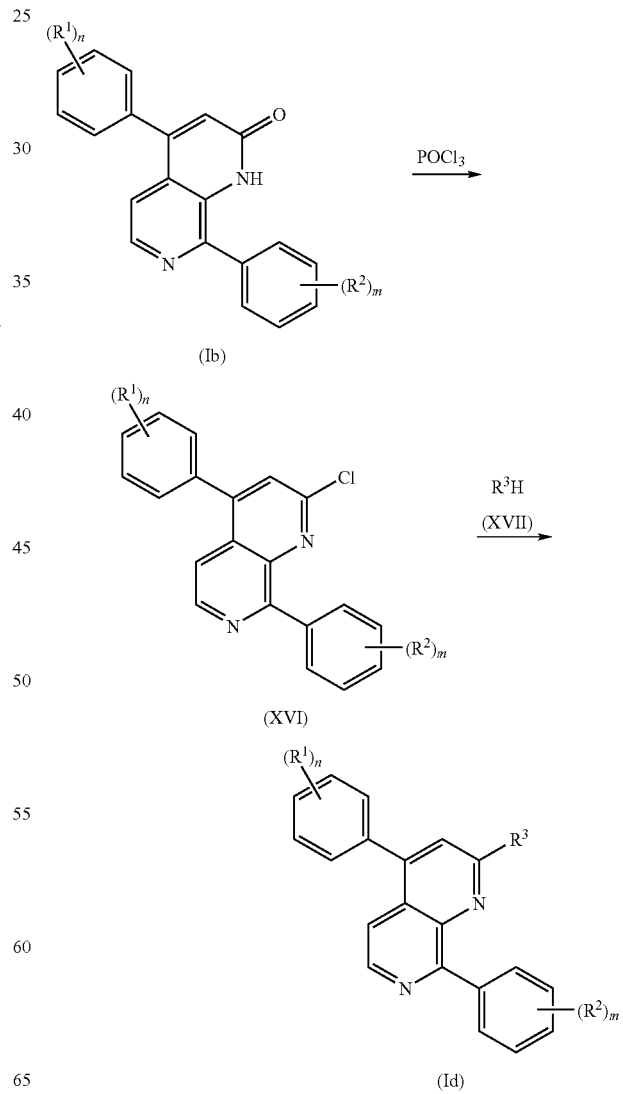

FIGURE 2

FIGURE 3

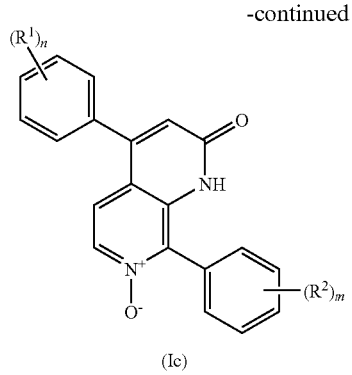
(Ic)

POCl₃ →

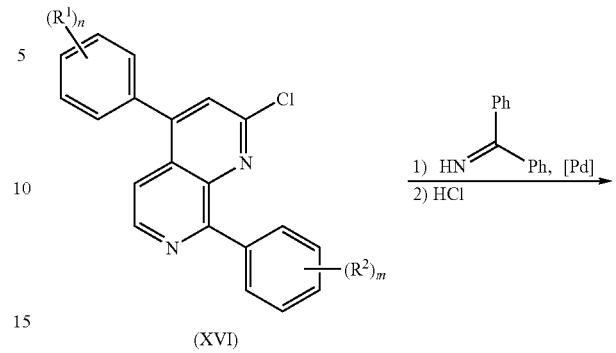
(XVI)

1) HN=C(Ph)Ph, [Pd]
2) HCl
→

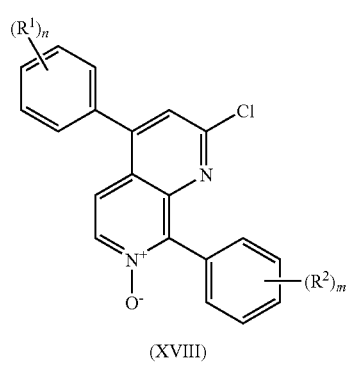
(XVIII)

R³H
(XVII)
→

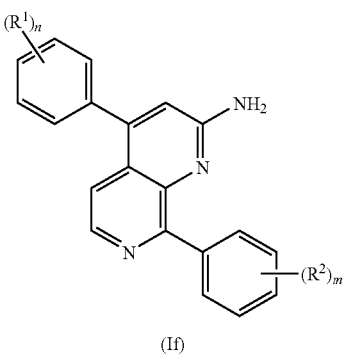
(If)

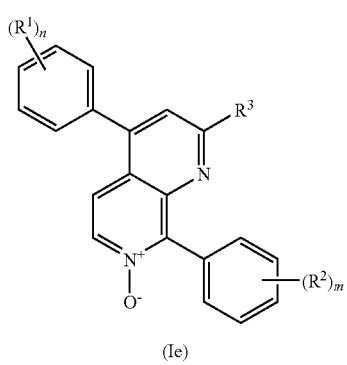
(Ie)

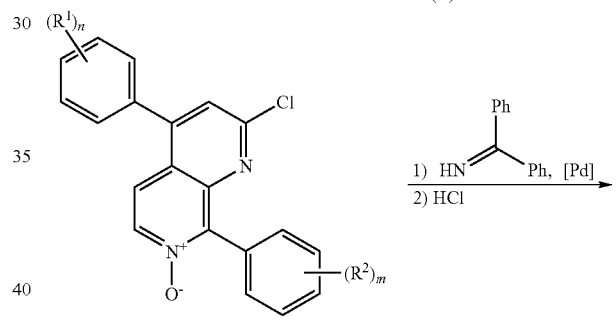
(XVIII)

1) HN=C(Ph)Ph, [Pd]
2) HCl
→

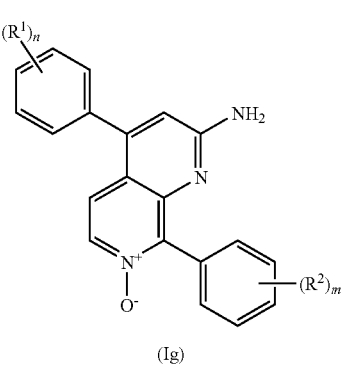
(Ig)

Thus, treatment of naphthyridones (Ib) or naphthyridones N-oxides (Ic) with a halogenating reagent such as neat phosphorus oxychloride or in a halogenated solvent at a temperature ranging from room temperature to 150° C. affords chloronaphthyridines (XVI) or chloronaphthyridines N-oxides (XVIII).

The reaction of compounds (XVI) or (XVIII) with compounds of formula (XVII) in protic solvents such as 2-ethoxyethanol or in aprotic solvents such as toluene, in the presence or absence of a base such as diisopropylethylamine, triethylamine, cesium carbonate, potassium carbonate, sodium carbonate or potassium phosphate at a temperature between room temperature and 160° C. gives naphthyridines (Id) or napthyridine N-oxides (Ie).

In the particular case of compounds of formula (I) where G is =CH— and R³ is an unsubstituted amino group the synthetic scheme shown below in FIG. 3 may be used.

The chloronaphthyridines (XVI) or their N-oxides (XVIII) may be coupled with 1,1-diphenylmethanimine by a Buchwald-Hartwig-type coupling reaction [a) Muci, A. R.; Buchwald, S. L. *Top. Curr. Chem.* 2002, 219, 131; b) Hartwig, J. F. *Angew. Chem. Int. Ed.* 1998, 37, 2046] and the resulting imine hydrolysed to yield, respectively, the compounds of formula (If) and (Ig). In the first step, such reactions may be catalysed by a palladium catalyst such as [1,1'-bis(diphenyl-phosphino)-ferrocene] dichloropalladium (II) complex with dichloromethane (1:1), tetrakis-(triphenylphosphine)-palladium(0), bis(triphenylphosphine)palladium(II) chloride, tris (dibenzylideneacetone)-dipalladium(0) or palladium (II) acetate in an aprotic organic solvent such as dioxane, toluene, DMF or 1,2-dimethoxyethane in the presence of a ligand such as racemic-2,2'-bis(diphenylphosphino)-1,1'-binaphthyl (racemic BINAP) and a base such as cesium carbonate, sodium carbonate or potassium phosphate at a temperature ranging from 80° C. to 140° C. In the second step, the iminium intermediate can be hydrolysed by treatment with an aqueous acidic medium, such as hydrochloric acid or trifluoroacetic acid at a temperature ranging from room temperature to 100° C.

Alternatively, compounds of formula (If) and (Ig) may be prepared following the synthetic scheme illustrated in FIG. 4. This route may also be used to obtain the compounds wherein G is =CH— and $R^3$ is a —COOH group.

FIGURE 4

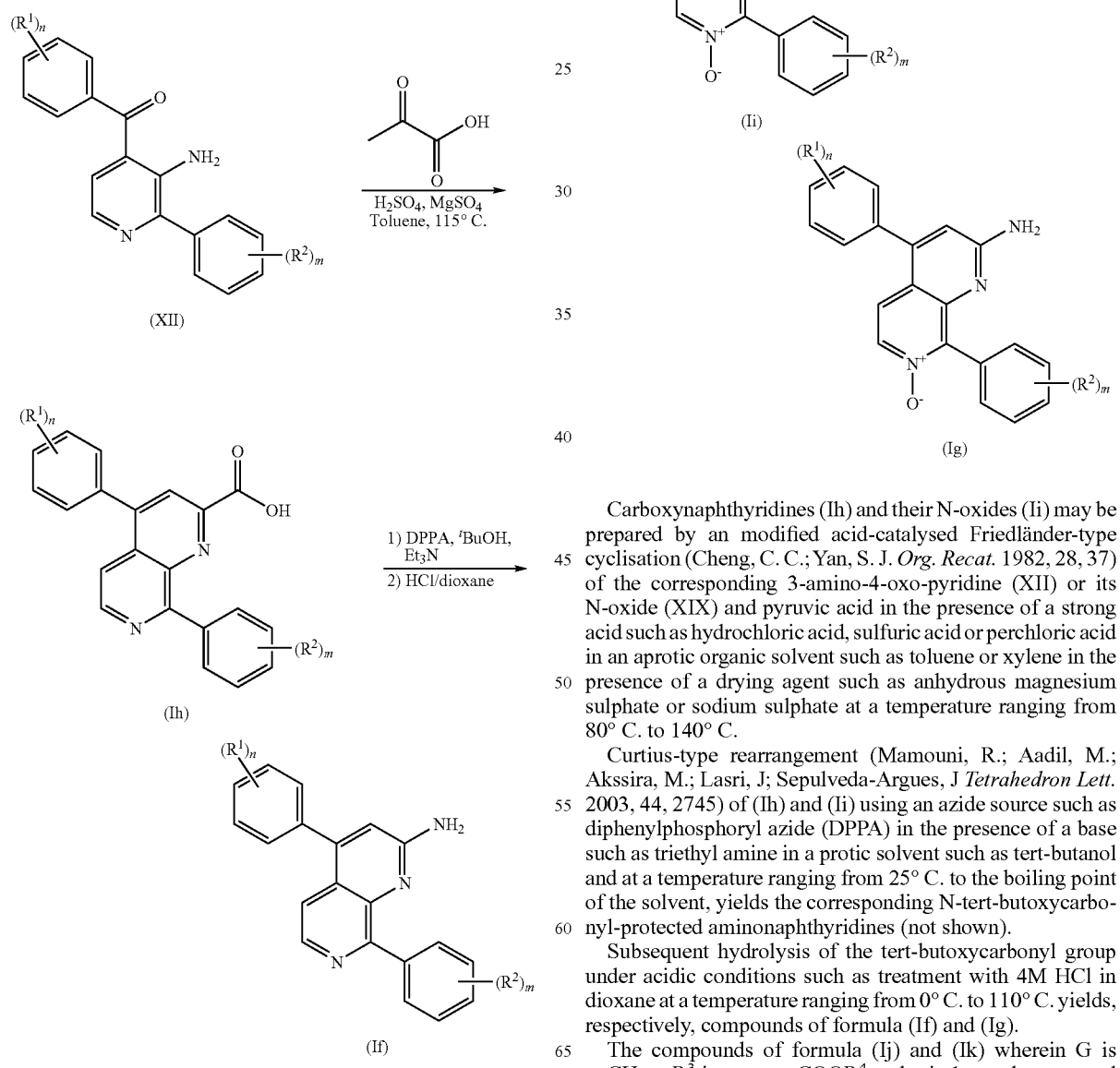

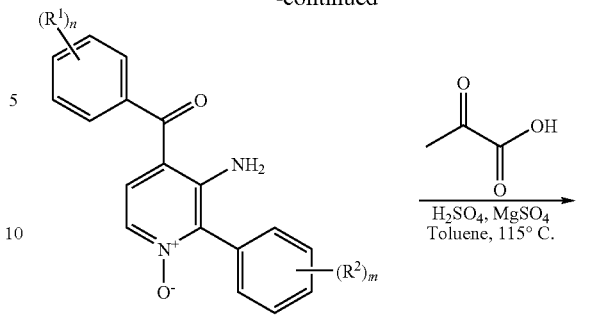

Carboxynaphthyridines (Ih) and their N-oxides (Ii) may be prepared by an modified acid-catalysed Friedländer-type cyclisation (Cheng, C. C.; Yan, S. J. Org. Recat. 1982, 28, 37) of the corresponding 3-amino-4-oxo-pyridine (XII) or its N-oxide (XIX) and pyruvic acid in the presence of a strong acid such as hydrochloric acid, sulfuric acid or perchloric acid in an aprotic organic solvent such as toluene or xylene in the presence of a drying agent such as anhydrous magnesium sulphate or sodium sulphate at a temperature ranging from 80° C. to 140° C.

Curtius-type rearrangement (Mamouni, R.; Aadil, M.; Akssira, M.; Lasri, J; Sepulveda-Argues, J Tetrahedron Lett. 2003, 44, 2745) of (Ih) and (Ii) using an azide source such as diphenylphosphoryl azide (DPPA) in the presence of a base such as triethyl amine in a protic solvent such as tert-butanol and at a temperature ranging from 25° C. to the boiling point of the solvent, yields the corresponding N-tert-butoxycarbonyl-protected aminonaphthyridines (not shown).

Subsequent hydrolysis of the tert-butoxycarbonyl group under acidic conditions such as treatment with 4M HCl in dioxane at a temperature ranging from 0° C. to 110° C. yields, respectively, compounds of formula (If) and (Ig).

The compounds of formula (Ij) and (Ik) wherein G is =CH—, $R^3$ is a group $COOR^4$ and p is 1 may be prepared following the synthetic scheme illustrated in FIG. 5.

FIGURE 5

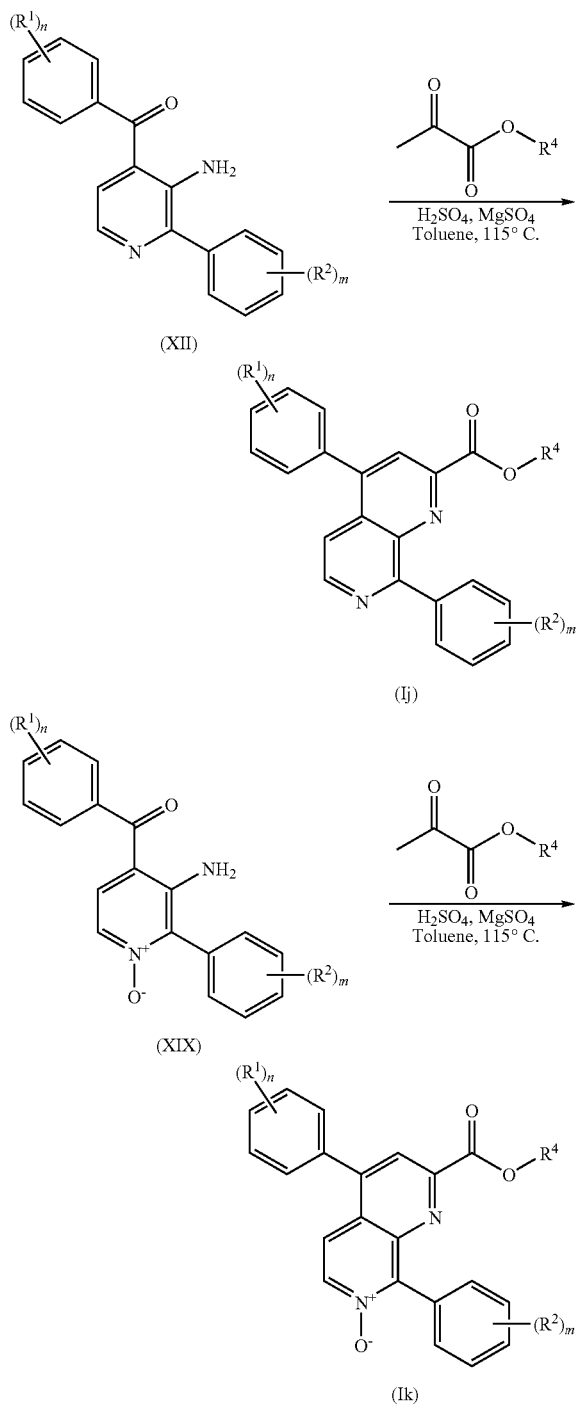

(XII)

(Ij)

(XIX)

(Ik)

Compounds of formula (Ij) or (Ik) may be prepared by an modified acid-catalysed Friedländer-type cyclisation (Cheng, C. C.; Yan, S. J. *Org. Recat* 1982, 28, 37) of the corresponding 3-amino-4-oxo-pyridine (XII) or its N-oxide (XIX) and pyruvic acid methyl ester in the presence of a strong acid such as hydrochloric acid, sulfuric acid or perchloric acid in an aprotic organic solvent such as toluene or xylene in the presence of a drying agent such as anhydrous magnesium sulphate or sodium sulphate at a temperature ranging from 80° C. to 140° C.

In the particular case of compounds of formula (I) wherein G is =CH— and $R^3$ is a group —NH—CO—$R^4$ the synthetic scheme shown below in FIG. 6 may be used.

FIGURE 6

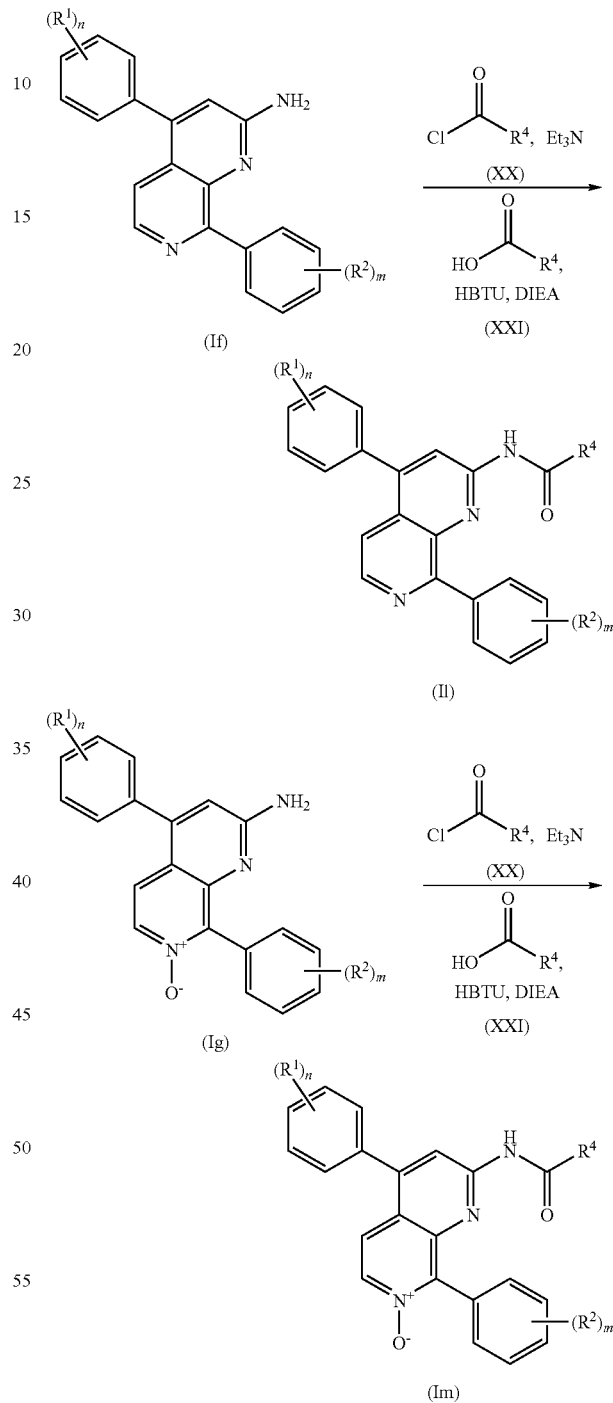

(If)

(Il)

(Ig)

(Im)

Reaction of aminonaphthyridines (If) or their N-oxides (Ig) with an acyl chloride (XX) in the presence of a base such as triethylamine, or diisopropylethylamine, using an halogenated solvent such as dichloromethane or an ether solvent such as dioxane at a temperature from 0° C. to 110° C. yields, respectively, compounds of formula (Il) and (Im).

Alternatively, compounds of formula (Il) and (Im) may be prepared by an amidation reaction of the corresponding aminonaphthyridines (If) and (Ig) with a carboxylic acid (XXI) in the presence of an amidation reagent such as 2-benzotriazol-1-yl-N,N,N',N'-tetramethyluronium hexafluorphosphate (HBTU), 2-benzotriazol-1-yl-N,N,N',N'-tetramethyluronium tetrafluoroborate (TBTU) or 1-(3-dimethylaminopropyl)-3-ethylcarbodiimide hydrochloride (EDC) and an organic base such as diisopropylethylamine or triethylamine in an aprotic organic solvent such as DMF or acetonitrile at room temperature.

In the particular case of compounds of formula (I) wherein G is =CH— and $R^3$ is a group —NH—SO$_2$—$R^4$ the synthetic scheme shown below in FIG. 7 may be used.

FIGURE 7

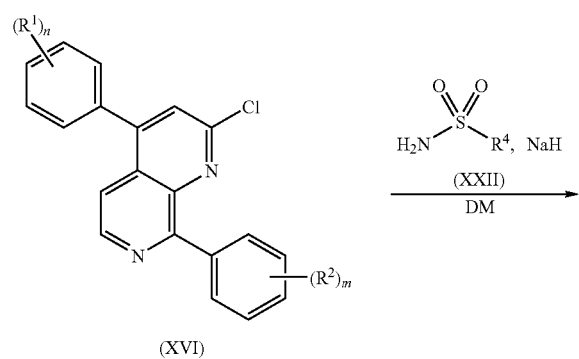

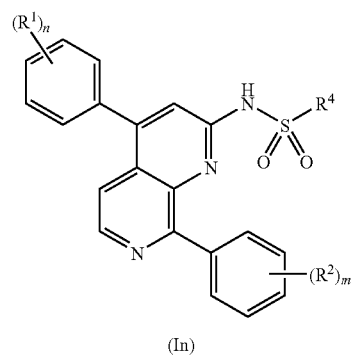

(In)

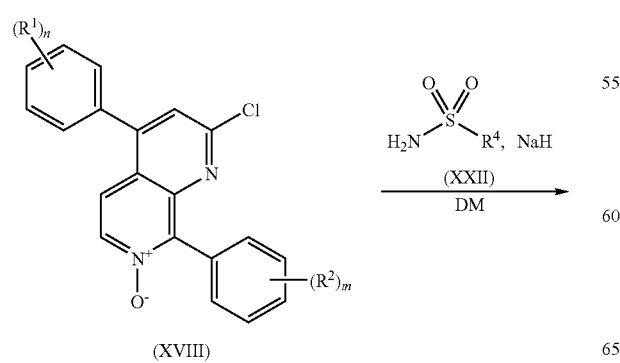

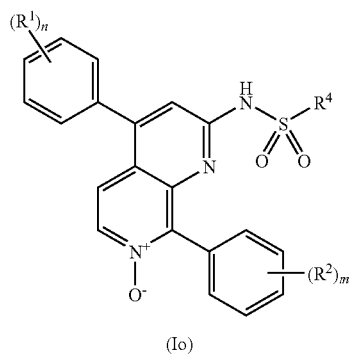

(Io)

Thus, compounds of formula (In) and (Io) can be obtained by treatment, respectively, of chloronaphthyridines (XVI) or their N-oxides (XVIII) with sulfonamides of formula (XXII) in the presence of a base such as sodium hydride or potassium hydride using an aprotic organic solvent such as dioxane, toluene, DMF, THF or 1,2-dimethoxyethane at a temperature ranging from room temperature to the boiling point of the solvent.

The present invention also provides a process, following the synthetic scheme illustrated in FIG. 8, for the preparation of compounds of formula (I) wherein G is =CH— and $R^3$ is group —NH—CO—OR$^4$.

FIGURE 8

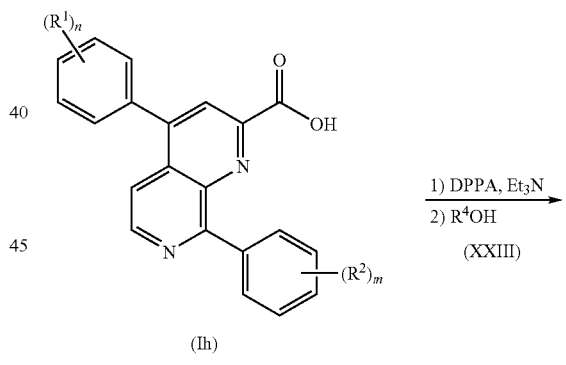

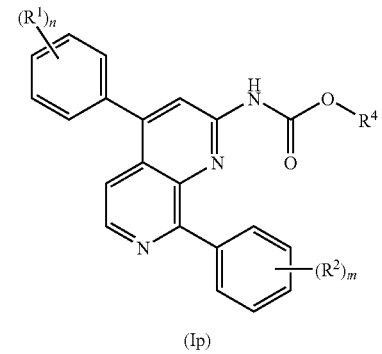

(Ip)

-continued

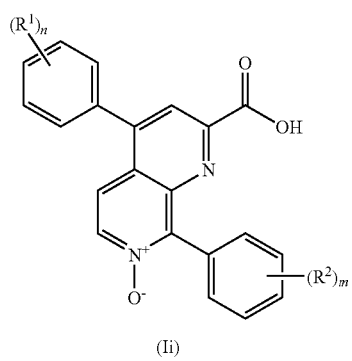

(Ii)

1) DPPA, Et₃N
2) R⁴OH
(XXIII)

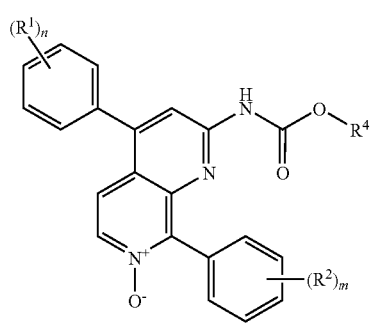

(Iq)

Curtius-type rearrangement (Mamouni, R.; Aadil, M.; Akssira, M.; Lasri, J; Sepulveda-Argues, J *Tetrahedron Lett.* 2003, 44, 2745) of (Ih) and (Ii) using an azide source such as diphenylphosphoryl azide (DPPA) in the presence of a base such as triethyl amine in an aprotic organic solvent such as dioxane, toluene, DMF or 1,2-dimethoxyethane and at a temperature ranging from 25° C. to the boiling point of the solvent, followed by the addition of alcohols of formula (XXIII), yields, respectively, carbamates (Ip) and (Iq).

In the particular case of compounds of formula (I) where G is =CH— and R³ is a group —CO—NH—R⁴ the synthetic scheme shown below in FIG. 9 may be used.

FIGURE 9

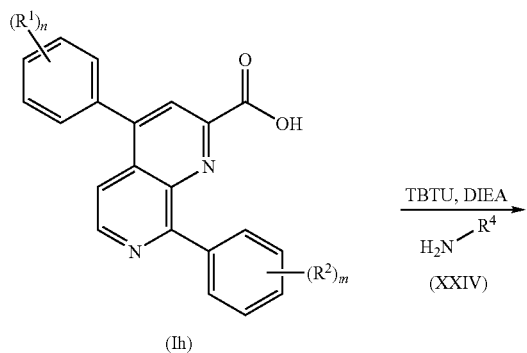

(Ih)

TBTU, DIEA
H₂N—R⁴
(XXIV)

-continued

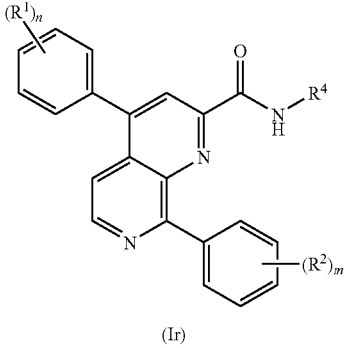

(Ir)

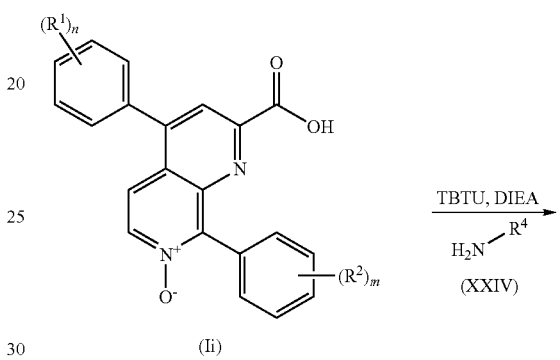

(Ii)

TBTU, DIEA
H₂N—R⁴
(XXIV)

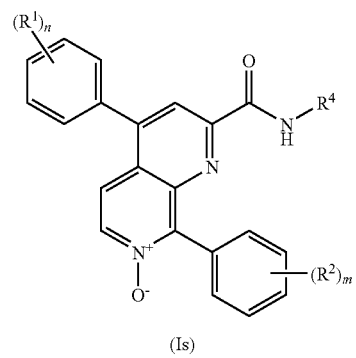

(Is)

Compounds of formula (Ir) and (Is) may be prepared by an amidation reaction of the corresponding carboxynaphthyridines (Ih) and (Ii) with an amine of formula (XXIV) in the presence of an amidation reagent such as 2-benzotriazol-1-yl-N,N,N',N'-tetramethyluronium hexafluorphosphate (HBTU), 2-benzotriazol-1-yl-N,N,N',N'-tetramethyluronium tetrafluoroborate (TBTU) or 1-(3-dimethylaminopropyl)-3-ethylcarbodiimide hydrochloride (EDC) and an organic base such as diisopropylethylamine or triethylamine in an aprotic organic solvent such as DMF or acetonitrile at room temperature.

According to a further feature of the present invention, compounds of general formula (I) wherein G is nitrogen and R³ is a hydrogen atom can be prepared following the synthetic scheme illustrated in FIG. 10.

FIGURE 10

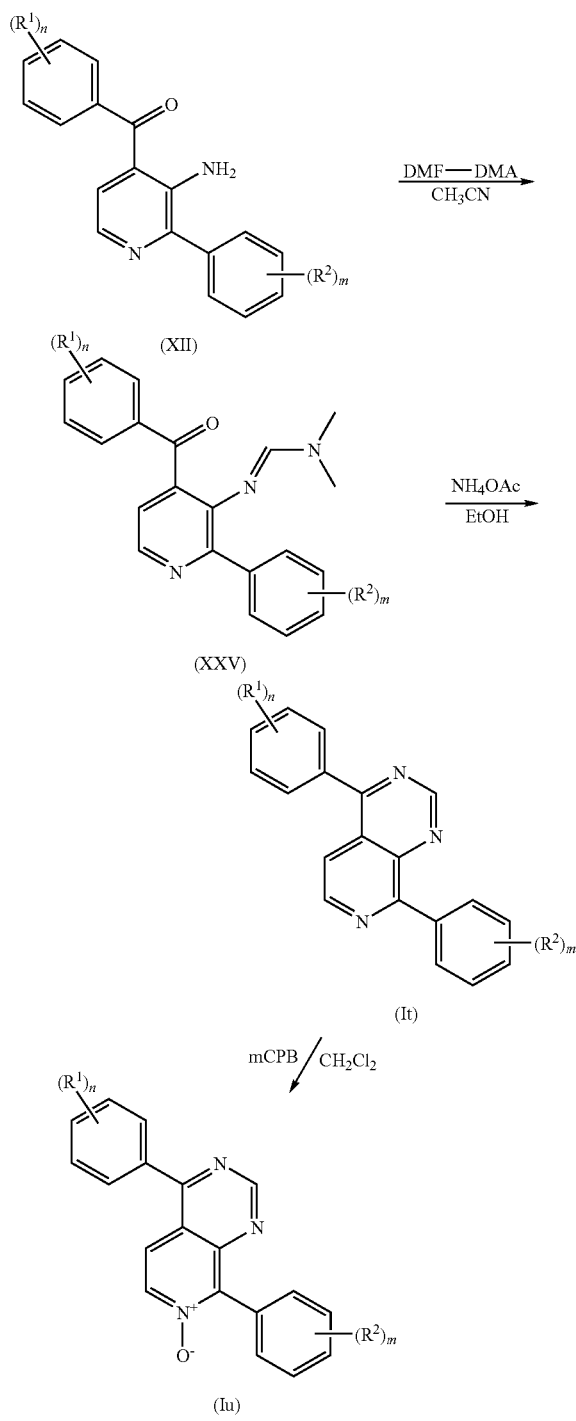

FIGURE 11

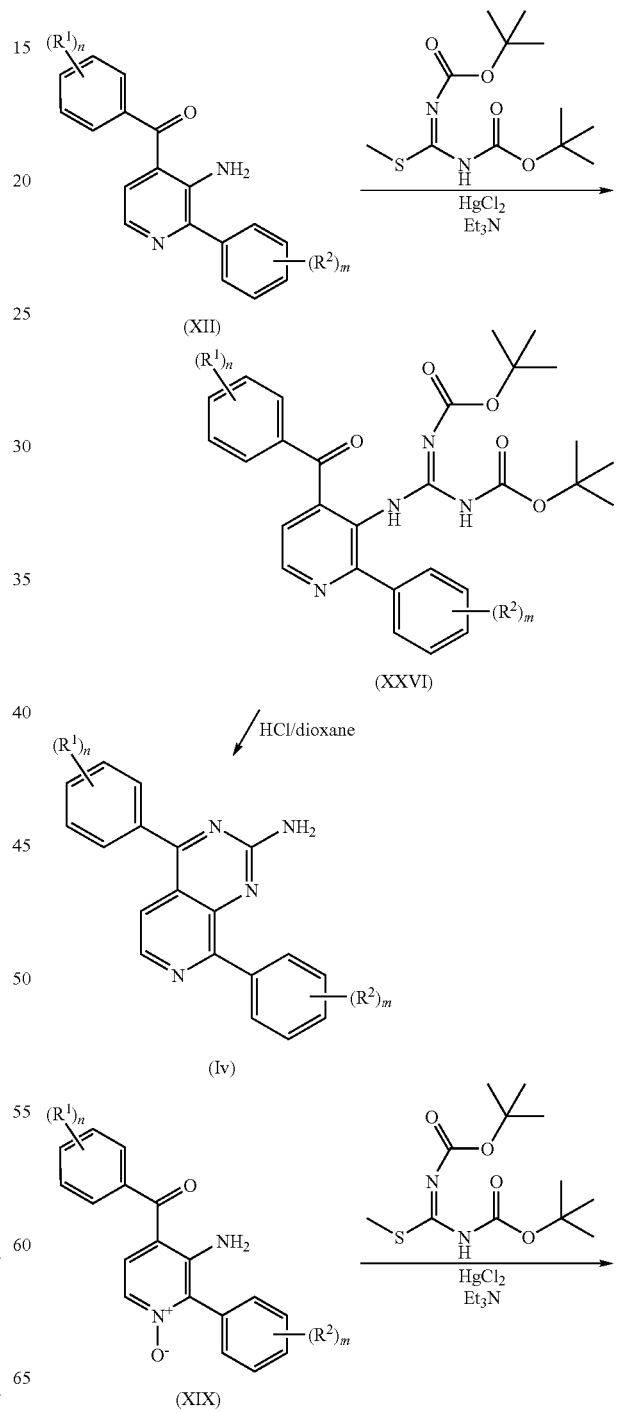

agent such as Oxone®, magnesium monoperoxyphthalate hexahydrate, hydrogen peroxide or meta-chloroperbenzoic acid, preferably with meta-chloroperbenzoic acid in an halogenated solvent such as dichloromethane, at a temperature ranging from 0° C. to the boiling point of the solvent to yield the pyridine N-oxides of formula (Iu).

In the particular case of compounds of formula (I) where G is nitrogen and $R^3$ is an amino group, the present invention also provides a process, following the synthetic scheme illustrated in FIG. 11, for the preparation of compounds of formula (XXXVI) and (XXXVII).

Reaction of aminopyridines (XII) with N,N-dimethylformamide dimethyl acetal using acetonitrile or a halogenated solvent such as dichloromethane at a temperature ranging from 0° C. to 110° C. yields compounds (XXV).

Compounds of formula (It) can be obtained by reaction of compounds of formula (XXV) with an ammonium source such as ammonium acetate in a protic solvent such as methanol, or ethanol at a temperature ranging from 0° C. to the boiling point of the solvent.

The nitrogen atom of the pyridine ring in the compounds of formula (It) may be selectively oxidised with an oxidising

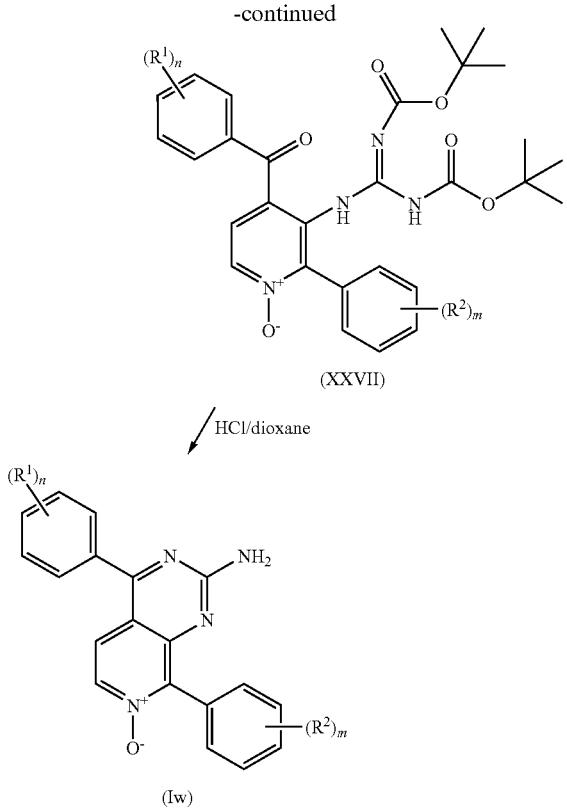

The intermediates of formula (XXVI) and (XXVII) may be obtained by reacting, respectively, the aminopyridines of formula (XII) and (XIX) with 1,3-bis(tert-butoxycarbonyl)-2-methyl-2-thiopseudourea. These reactions may be promoted by a Lewis acid such as mercury (II) chloride in an halogenated solvent such as dichloromethane and in the presence of a base such as cesium carbonate, sodium carbonate or triethyl amine at a temperature ranging from 0° C. to the boiling point of the solvent.

Reaction of intermediates (XXVI) and (XXVII) with organic or inorganic acids such as 4M HCl in dioxane at a temperature ranging from 0° C. to 110° C. yields, after an intramolecular cyclization reaction, the compounds of formula (Iv) and (Iw), respectively.

The present invention also provides a process, following the synthetic scheme illustrated in FIG. 12, for the preparation of compounds of formula (I) wherein G is nitrogen and $R^3$ is selected from the group consisting of —OH, —$NR^4R^5$, —NH—$(CH_2)$q-$NR^4R^5$, —S—$(CH_2)_q$—$NR^4R^5$, —O—$(CH_2)_q$—$NR^4R^5$

FIGURE 12

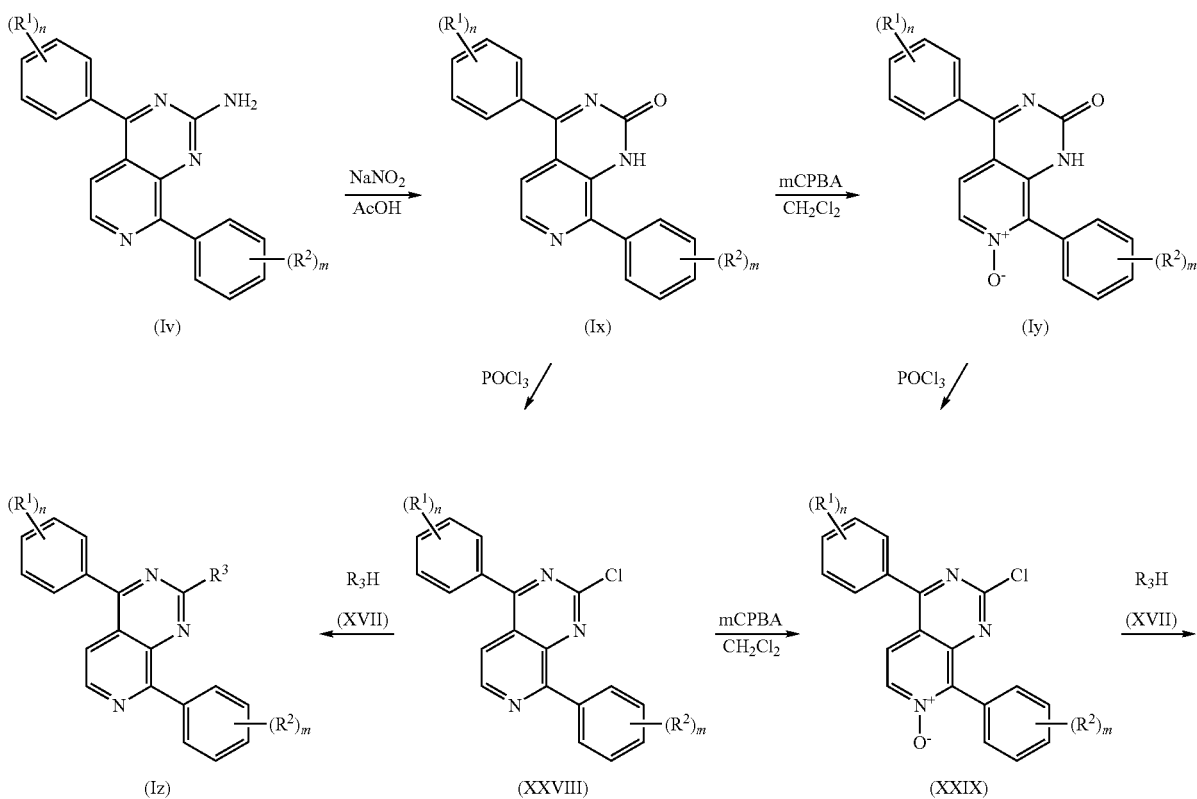

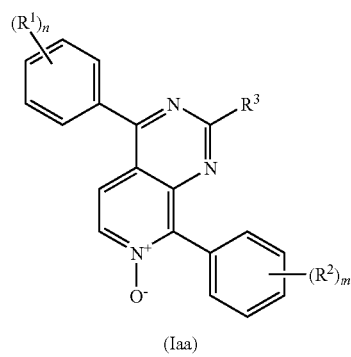

(Iaa)

Reaction of aminopyridopyrimidines (Iv) with a nitrite source such us sodium nitrite in a protic solvent such as acetic acid at a temperature ranging from room temperature to the boiling point of the solvent yields the pyridopyrimidones (Ix).

Subsequent oxidation of the pyridopyrimidones of formula (Ix) with an oxidizing agent such as Oxone®, magnesium monoperoxyphthalate hexahydrate, hydrogen peroxide or meta-chloroperbenzoic acid, preferably with meta-chloroperbenzoic in an halogenated solvent such as dichloromethane and a temperature ranging from 0° C. to the boiling point of the solvent, yields the pyridopyrimidone N-oxides of formula (Iy).

The intermediates of formula (XXVIII) and (XXIX) may be obtained by reacting, respectively, the corresponding pyridopyrimidones of formula (Ix) and (Iy) with phosphorus oxybromide neat or in an halogenated solvent such as dichloromethane at a temperature from 60° C. to 140° C.

The reaction of compounds (XXVIII) or (XXIX) with compounds of formula (XVII) in protic solvents such as 2-ethoxyethanol or in aprotic solvents such as toluene, in the presence or absence of a base such as diisopropylethylamine, triethylamine, cesium carbonate, potassium carbonate, sodium carbonate or potassium phosphate at a temperature between room temperature and 160° C. gives, respectively, pyridopyrimidines (Iz) or pyridopyrimidine N-oxides (Iaa).

Alternatively, compounds of formula (XXIX) can be obtained by oxidation of the chloropyridopyrimidines of formula (XXVIII) with an oxidizing agent such as Oxone®, magnesium monoperoxyphthalate hexahydrate, hydrogen peroxide or meta-chloroperbenzoic acid, preferably with meta-chloroperbenzoic acid in an halogenated solvent such as dichloromethane and a temperature ranging from 0° C. to the boiling point of the solvent.

In the particular case of compounds of formula (I) where G is nitrogen and $R^3$ is a group —NH—CO—$R^4$ the synthetic scheme shown below in FIG. 13 may be used.

FIGURE 13

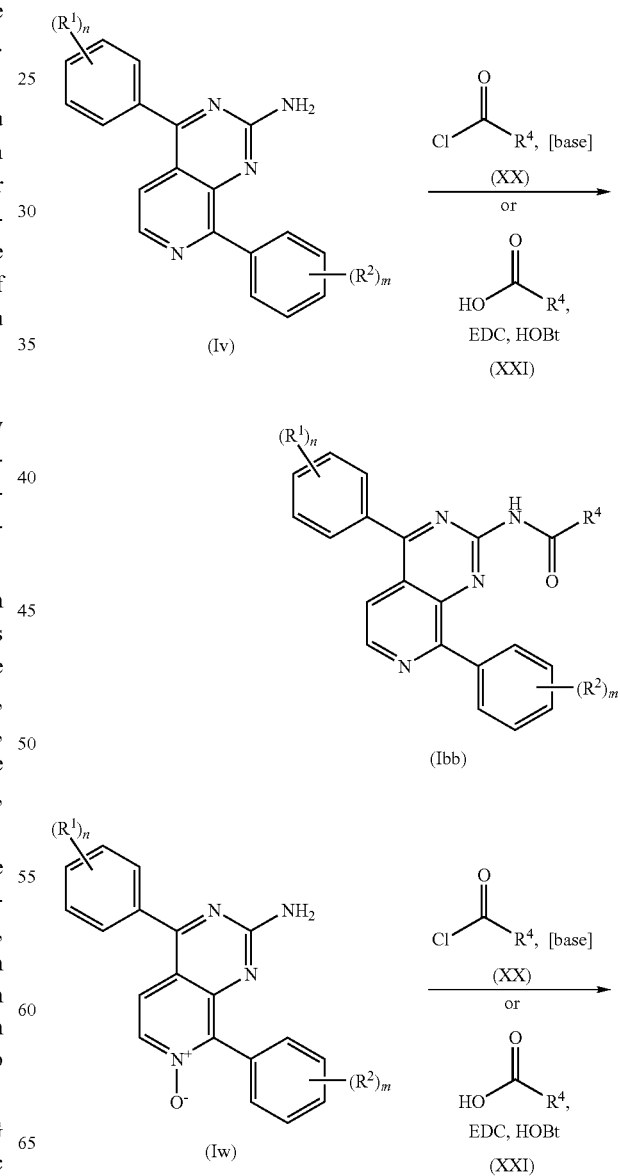

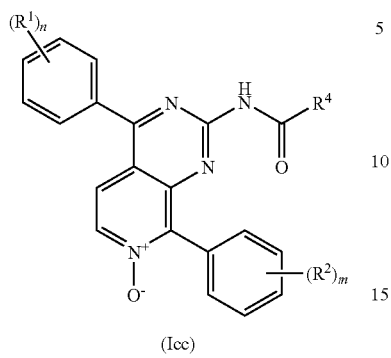

(Icc)

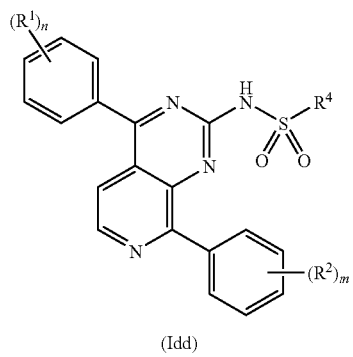

(Idd)

Reaction of aminopyridopyrimidines (Iv) or their N-oxides (Iw) with an acyl chloride (XX) in the presence of a base such as triethylamine, or diisopropylethylamine, using an halogenated solvent such as dichloromethane or an ether solvent such as dioxane at a temperature from 0° C. to 110° C. yields, respectively, compounds of formula (Ibb) and (Icc).

Alternatively, compounds of formula (Ibb) and (Icc) may be prepared by an amidation reaction of the corresponding aminopyridopyrimidines (Iv) and (Iw) with a carboxilic acid (XXI) in the presence of an amidation reagent such as 2-benzotriazol-1-yl-N,N,N',N'-tetramethyluronium hexafluorphosphate (HBTU), 2-benzotriazol-1-yl-N,N,N',N'-tetramethyluronium tetrafluoroborate (TBTU) or 1-(3-dimethylaminopropyl)-3-ethylcarbodiimide hydrochloride (EDC) and an organic base such as diisopropylethylamine or triethylamine in an aprotic organic solvent such as DMF or acetonitrile at room temperature.

In the particular case of compounds of formula (I) where G is nitrogen and $R^3$ is a group —NH—SO$_2$—R$^4$ the synthetic scheme shown below in FIG. 14 may be used.

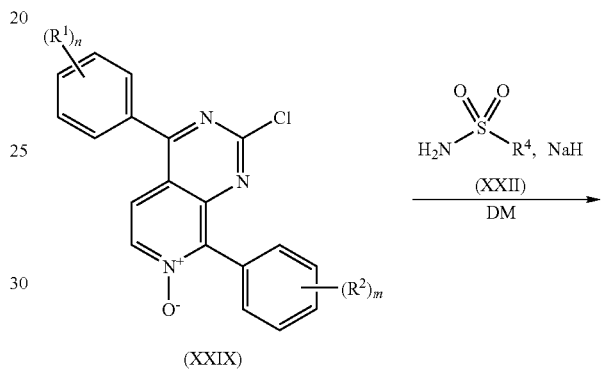

(XXIX)

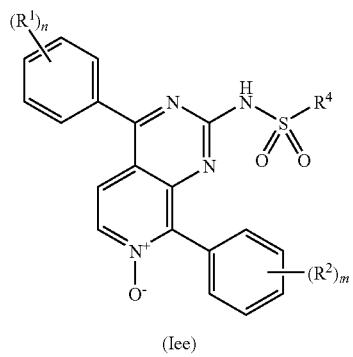

(Iee)

Thus, compounds of formula (Idd) and (Iee) can be obtained by treatment, respectively, of chloropyridopyrimidines (XXVIII) or their N-oxides (XXIX) with sulfonamides of formula (XII) in the presence of a base such as sodium hydride or potassium hydride using an aprotic organic solvent such as dioxane, toluene, DMF, THF or 1,2-dimethoxyethane at a temperature ranging from room temperature to the boiling point of the solvent.

The present invention also provides a process, following the synthetic scheme illustrated in FIG. 15, for the preparation of compounds of formula (I) wherein G is nitrogen and $R^3$ is selected from the group consisting of —COOH and —COOR$^4$.

FIGURE 14

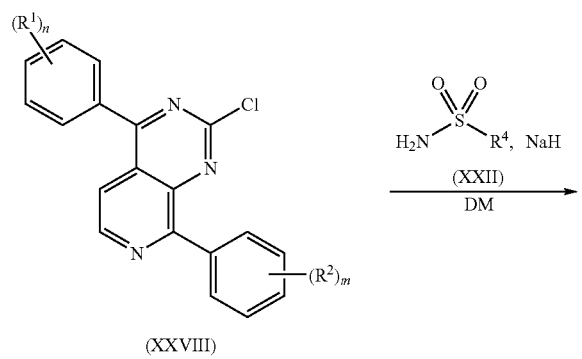

(XXVIII)

FIGURE 15

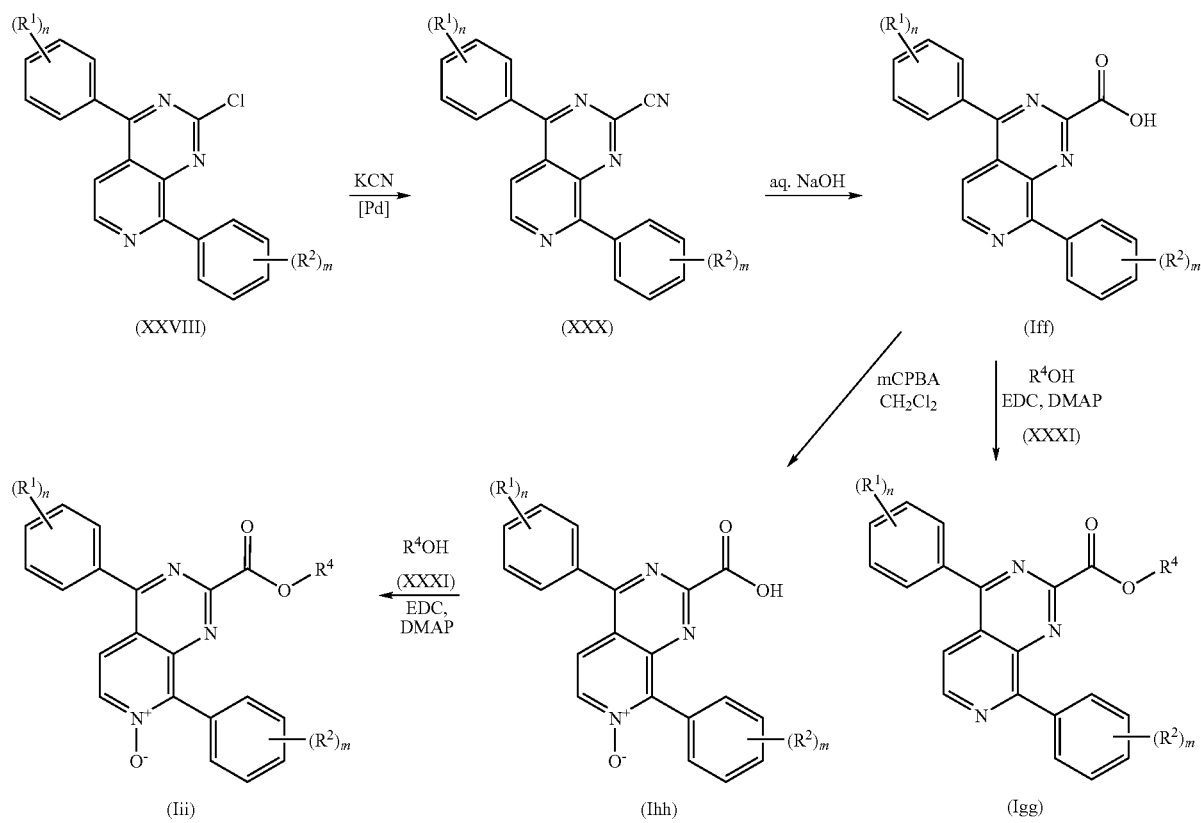

Cyanoderivatives (XXX) may be obtained by reacting chloropyridopyrimidines (XXVIII) with a cyanide source such as potassium cyanide or sodium cyanide in the presence of a palladium catalyst such as [1,1'-bis(diphenylphosphino)-ferrocene] dichloropalladium (II) complex with dichloromethane (1:1), tetrakis(triphenylphosphine)-palladium(0), bis(triphenylphosphine)palladium(II) chloride or tris(dibenzylideneacetone)-dipalladium(0) in an aprotic organic solvent such as dioxane, toluene, DMF or 1,2-dimethoxyethane at a temperature from 80° C. to 140° C.

Subsequent hydrolysis of the cyano group in compounds of formula (XXX) in basic conditions such as treatment with aqueous 1M NaOH or 1M KOH at a temperature ranging from room temperature to 110° C. yields the carboxypyridopyrimidines of formula (Iff).

Oxidation of the carboxypyridopyrimidines of formula (Iff) with an oxidizing agent such as Oxone®, magnesium monoperoxyphthalate hexahydrate, hydrogen peroxide or meta-chloroperbenzoic acid, preferably with meta-chloroperbenzoic in an halogenated solvent such as dichloromethane and a temperature ranging from 0° C. to the boiling point of the solvent, yields the carboxypyridopyrimidine N-oxides of formula (Ihh).

Thus, treatment of compounds of formula (Iff) or (Ihh) with an alcohol of formula (XXXI) in the presence of an esterification reagent such as 1-(3-dimethylaminopropyl)-3-ethylcarbodiimide hydrochloride (EDC) and a catalyst such as N,N-dimethylaminopyridine (DMAP) in an aprotic organic solvent such as THF, DMF or acetonitrile at room temperature yields, respectively, compounds (Igg) and (Iii).

In the particular case of compounds of formula (I) where G is nitrogen and $R^3$ is a group —NH—CO—$OR^4$ the synthetic scheme shown below in FIG. 16 may be used.

FIGURE 16

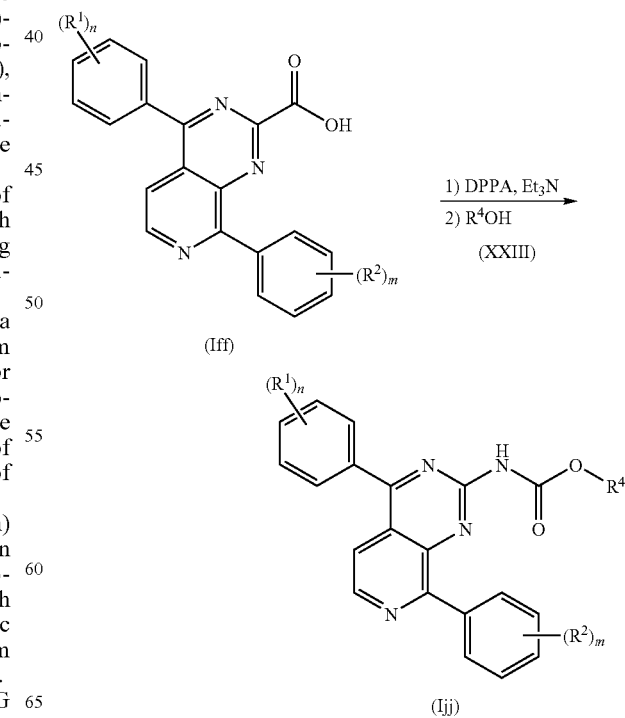

33

-continued

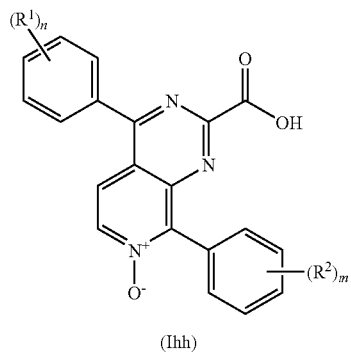

(Ihh)

1) DPPA, Et₃N
2) R⁴OH
(XXIII)

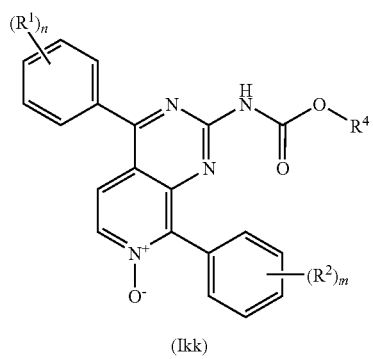

(Ikk)

Curtius-type rearrangement (Mamouni, R.; Aadil, M.; Akssira, M.; Lasri, J; Sepulveda-Argues, J *Tetrahedron Lett.* 2003, 44, 2745) of (Iff) and (Ihh) using an azide source such as diphenylphosphoryl azide (DPPA) in the presence of a base such as triethyl amine in an aprotic organic solvent such as dioxane, toluene, DMF or 1,2-dimethoxyethane and at a temperature ranging from 25° C. to the boiling point of the solvent, followed by the addition of alcohols of formula (XXIII), yields, respectively, carbamates (Ijj) and (Ikk).

In the particular case of compounds of formula (I) where G is nitrogen and R³ is a group —CO—NH—R⁴ the synthetic scheme shown below in FIG. 17 may be used.

FIGURE 17

34

-continued

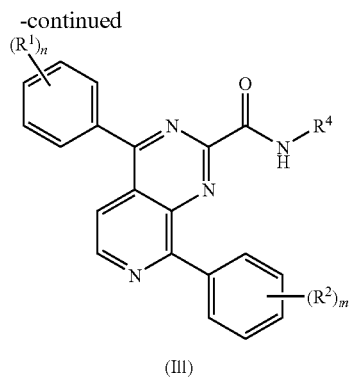

(Ill)

TBTU, DIEA $H_2N-R^4$ (XXIV)

Compounds of formula (Ill) and (Imm) may be prepared by an amidation reaction of the corresponding carboxypyridopyrimidines (Iff) and (Ihh) with an amine of formula (XXIV) in the presence of an amidation reagent such as 2-benzotriazol-1-yl-N,N,N',N'-tetramethyluronium hexafluorphosphate (HBTU), 2-benzotriazol-1-yl-N,N,N',N'-tetramethyluronium tetrafluoroborate (TBTU) or 1-(3-dimethylaminopropyl)-3-ethylcarbodiimide hydrochloride (EDC) and an organic base such as diisopropylethylamine or triethylamine in an aprotic organic solvent such as DMF or acetonitrile at room temperature.

The 1,7-naphthyridine or pyrido[3,4-d]pyrimidine derivatives of formula (I) can be converted by methods known per se into pharmaceutically acceptable salts or N-oxides. Preferred salts are acid addition salts obtainable by treatment with organic or inorganic acids such as fumaric, tartaric, succinic or hydrochloric acid.

Biological Testing

Inhibition Assay

Enzymatic activity assay was performed in 96-well microtiter plates (Corning, catalog number #3686) using a total volume of 50 μl of an assay buffer composed of 50 mM HEPES pH 7.5, 10 mM $MgCl_2$, 1.75 mM $Na_3VO_4$.

Various concentrations of the test compound or vehicle controls were pre-incubated for one hour with 0.055 μg/ml of the human p38alfa (SAPKa) enzyme (obtained from University of Dundee). The reaction started by addition of biotinylated ATF2 substrate and ATP in concentrations around their Km values (final concentration 0.62 µM and 60 µM respectively) and took place for one hour at 25° C. Addition of the detection reagents, streptavidin-XL665 and anti-phospho-residue antibody coupled to Europium cryptate, caused the juxtaposition of the cryptate and the XL665 fluorophore, resulting in fluorescence energy transfer (FRET). The FRET intensity depends on the amount of bounded cryptate antibody, which is proportional to the extent of substrate phosphorylation. FRET intensity was measured using Victor 2V spectrofluorometer. Data were analyzed by non-linear regression (Hill equation) to generate a dose-response curve. The calculated $IC_{50}$ value is the concentration of the test compound that caused a 50% decrease in the maximal FRET intensity.

Functional Assay

The activity of compounds in inhibiting TNFα production was measured in a cellular assay using the human monocytic cel line THP-1. For this purpose, $2 \times 10^5$ cells/well were plated in tissue-culture treated round-bottom 96-well plates in RPMI (containing 10% FCS, L-Gln 2 mM, Hepes buffer 10 mM, sodium pyruvate 1 mM, glucose 4.5 gr/L, $HNaCO_3$ 1.5 g/L and beta-mercaptoethanol 50 µM), together with compounds at the desired test concentration and LPS (Sigma, L2630) at a final 10 µg/ml concentration. Compounds were resuspended in 100% DMSO at a concentration of 1 mM and titrated thereof in 10× dilutions in medium. Controls included stimulated cells alone and stimulated cells treated with the highest concentration of compound vehicle (1% DMSO). Cells were incubated for 5 h at 37° C. in a 5% $CO_2$ atmosphere. Cell supernatant was recovered by centrifugation and diluted 5-fold prior to testing in a standard human TNFα ELISA (RnD systems).

Data were analyzed by non-linear regression (Hill equation) to generate a dose-response curve. The calculated $IC_{50}$ value is the concentration of the test compound that caused a 50% decrease in the maximal TNFα production.

Compounds of the present invention are good inhibitors of TNFα production. Preferred 1,7-naphthyridine or pyrido[3,4-d]pyrimidine derivatives of the invention possess an $IC_{50}$ value for inhibiting TNFα production of less than 10 µM, preferably less than 1 µM and most preferably less than 100 nM.

Table 1 shows the activities in p38 assay of some compounds of the present invention.

TABLE 1

| Example | p38α $IC_{50}$ (nM) |
|---|---|
| 2 | 22 |
| 8 | 6 |
| 10 | 14 |
| 12 | 3.3 |
| 17 | 13 |
| 18 | 15 |
| 19 | 8 |
| 20 | 12 |
| 21 | 66 |
| 22 | 85 |
| 26 | 35 |
| 30 | 28 |
| 32 | 34 |

It can be seen from Table 1 that the compounds of formula (I) are potent inhibitors of the p38 mitogen-activated protein kinase. Preferred 1,7-naphthyridine or pyrido[3,4-d]pyrim- idines derivatives of the invention possess an $IC_{50}$ value of inhibition of p38α of less than 1 µM, preferably less than 100 nM, more preferably less than 80 nM and most preferably less than 50 nM.

The 1,7-naphthyridine or pyrido[3,4-d]pyrimidines derivatives of the invention are useful in the treatment or prevention of diseases known to be susceptible to improvement by inhibition of the p38 mitogen-activated protein kinase. Such diseases are, for example rheumatoid arthritis, ischemia-reperfusion injury, cerebral focal ischemia, acute coronary syndrome, COPD, Crohn's disease, irritable bowle syndrome, adult respiratory distress syndrome, osteoporosis Alzheimer's disease, rheumatoid spondylitis, psoriasis, atherosclerosis, osteoarthritis or multiple myeloma.

Accordingly, the 1,7-naphthyridine or pyrido[3,4-d]pyrimidine derivatives of the invention and pharmaceutical compositions comprising such compound and/or salts thereof may be used in a method of treatment of disorders of the human or animal body which comprises administering to a subject requiring such treatment an effective amount of a compound of the invention or a pharmaceutically acceptable salt thereof.

The present invention also provides pharmaceutical compositions which comprise, as an active ingredient, at least a naphthyridine or pyrido[3,4-d]pyrimidine derivative of formula (I) or a pharmaceutically acceptable salt thereof in association with a pharmaceutically acceptable excipient such as a carrier or diluent. The active ingredient may comprise 0.001% to 99% by weight, preferably 0.01% to 90% by weight of the composition depending upon the nature of the formulation and whether further dilution is to be made prior to application.

The diluents which may be used in the preparation of the compositions include those liquid and solid diluents which are compatible with the active ingredient, together with colouring or flavouring agents, if desired. Tablets or capsules may conveniently contain between 2 and 500 mg of active ingredient or the equivalent amount of a salt thereof.

The pharmaceutically acceptable excipients which are admixed with the active compound or salts of such compound, to form the compositions of this invention are well-known per se and the actual excipients used depend inter alia on the intended method of administering the compositions.

The 1,7-naphthyridine or pyrido[3,4-d]pyrimidine derivatives of the invention may also be combined with other active compounds in the treatment of diseases known to be susceptible to improvement by treatment with an inhibitor of the p38 mitogen-activated protein kinase.

The combinations of the invention can optionally comprise one or more additional active substances which are known to be useful in the treatment of respiratory or inflammatory disorders, such as antagonists of M3 muscarinic receptors, β2-agonists, PDE4 inhibitors, corticosteroids or glucocorticoids, CysLT1 and/or CysLT2 antagonists (also known as leukotriene D4 antagonists), inhibitors of egfr-kinase, antagonists of the A2b adenosine receptor, NK1-receptor antagonists, CRTh2 antagonists, syk kinase inhibitors, CCR3 antagonists, VLA-4 antagonists and disease modifying anti-rheumatic drugs (DMARDs) such as methotrexate.

When 1,7-naphthyridine or pyrido[3,4-d]pyrimidine derivatives of the invention are used for the treatment of respiratory diseases such as asthma, chronic obstructive pulmonary disorder, pulmonary fibrosis, emphysema it may be advantageous to use them in combination with other active compounds known to be useful in the treatment of respiratory diseases such as (1) antagonists of M3 muscarinic receptors, (2) β2-agonists, (3) PDE4 inhibitors, (4) corticosteroids, (5)

CysLT1 and/or CysLT2 antagonists, (6) inhibitors of egfr-kinase, (7) A2b antagonits, (8) NK1 receptor agonists, (9) CRTh2 antagonists, (10) syk kinase inhibitors, (11) CCR3 antagonists, (12) VLA-4 antagonists and (13) disease modifying antirheumatic drugs (DMARDs) such as methotrexate.

When 1,7-naphthyridine or pyrido[3,4-d]pyrimidine derivatives of the invention are used for the treatment of autoimmune diseases such as psoriasis, rheumatoid arthritis, psoriatic arthritis, ankylosing spondilytis, Reiter's syndrome, fibromyalgia, inflammatory bowel disease such as ulcerative colitis and Crohn's disease, multiple sclerosis, diabetes, glomerulonephritis, systemic lupus erythematosus, scleroderma, chronic thyroiditis, Grave's disease, hemolytic anemia, autoimmune gastritis, autoimmune neutropenia, thrombocytopenia, autoimmune chronic active hepatitis, myasthenia gravis, or Addison's disease it may be advantageous to use them in combination with other active compounds known to be useful in the treatment of autoimmune diseases such as PDE4 inhibitors, CysLT1 and/or CysLT2 antagonists, inhibitors of egfr-kinase, A2b antagonits, NK1 receptor agonists, CCR3 antagonists, VLA-4 antagonists and disease modifying antirheumatic drugs (DMARDs).

Examples of suitable M3 antagonists (anticholinergics) that can be combined with the inhibitors of the p38 mitogen-activated protein kinase of the present invention are tiotropium salts, oxitropium salts, flutropium salts, ipratropium salts, glycopyrronium salts, trospium salts, revatropate, espatropate, 3-[2-hydroxy-2,2-bis(2-thienyl)acetoxy]-1-(3-phenoxypropyl)-1-azoniabicyclo[2.2.2]octane salts, 1-(2-Phenylethyl)-3-(9H-xanthen-9-ylcarbonyloxy)-1-azoniabicyclo[2.2.2]octane salts, 2-oxo-1,2,3,4-tetrahydroquinazoline-3-carboxylic acid endo-8-methyl-8-azabicyclo[3.2.1]oct-3-yl ester salts (DAU-5884), 3-(4-Benzylpiperazin-1-yl)-1-cyclobutyl-1-hydroxy-1-phenylpropan-2-one (NPC-14695), N-[1-(6-Aminopyridin-2-ylmethyl)piperidin-4-yl]-2(R)-[3,3-difluoro-1(R)-cyclopentyl]-2-hydroxy-2-phenylacetamide (J-104135), 2(R)-Cyclopentyl-2-hydroxy-N-[1-[4(S)-methylhexyl]piperidin-4-yl]-2-phenylacetamide (J-106366), 2(R)-Cyclopentyl-2-hydroxy-N-[1-(4-methyl-3-pentenyl)-4-piperidinyl]-2-phenylacetamide (J-104129), 1-[4-(2-aminoethyl)piperidin-1-yl]-2(R)-[3,3-difluorocyclopent-1(R)-yl]-2-hydroxy-2-phenylethan-1-one (Banyu-280634), N—[N-[2-[N-[1-(cyclohexylmethyl)piperidin-3(R)-ylmethyl]carbamoyl]ethyl]carbamoylmethyl]-3,3,3-triphenylpropionamide (Banyu CPTP), 2(R)-cyclopentyl-2-hydroxy-2-phenylacetic acid 4-(3-azabicyclo[3.1.0]hex-3-yl)-2-butynyl ester (Ranbaxy 364057), UCB-101333, Merck's OrM3, 7-endo-(2-hydroxy-2,2-diphenylacetoxy)-9,9-dimethyl-3-oxa-9-azoniatricyclo[3.3.1.0(2,4)]nonane salts, 7-(2,2-diphenylpropionyloxy)-7,9,9-trimethyl-3-oxa-9-azoniatricyclo[3.3.1.0*2,4*]nonane salts, 7-hydroxy-7,9,9-trimethyl-3-oxa-9-azoniatricyclo[3.3.1.0*2,4*]nonane 9-methyl-9H-fluorene-9-carboxylic acid ester salts, all of them optionally in the form of their racemates, their enantiomers, their diastereomers and mixtures thereof, and optionally in the form of their pharmacologically-compatible acid addition salts. Among the salts chlorides, bromides, iodides and methanesulphonates are preferred.

Examples of suitable β2-agonists that can be combined with the inhibitors of the p38 mitogen-activated protein kinase of the present invention are: arformoterol, bambuterol, bitolterol, broxaterol, carbuterol, clenbuterol, dopexamine, fenoterol, formoterol, hexoprenaline, ibuterol, isoetharine, isoprenaline, levosalbutamol, mabuterol, meluadrine, metaproterenol, nolomirole, orciprenaline, pirbuterol, procaterol, reproterol, ritodrine, rimoterol, salbutamol, salmefamol, salmeterol, sibenadet, soterenot, sulfonterol, terbutaline, tiaramide, tulobuterol, GSK-597901, GSK-159797, HOKU-81, (−)-2-[7(S)-[2(R)-Hydroxy-2-(4-hydroxyphenyl)ethylamino]-5,6,7,8-tetrahydro-2-naphthyloxy]-N,N-dimethylacetamide hydrochloride monohydrate, carmoterol, QAB-149 and 5-[2-(5,6-diethylindan-2-ylamino)-1-hydroxyethyl]-8-hydroxy-1H-quinolin-2-one, 4-hydroxy-7-[2-{[2-{[3-(2-phenylethoxy)propyl]sulfonyl}ethyl]amino}ethyl]-2(3H)-benzothiazolone, 1-(2-fluoro-4-hydroxyphenyl)-2-[4-(1-benzimidazolyl)-2-methyl-2-butylamino]ethanol, 1-[3-(4-methoxybenzylamino)-4-hydroxyphenyl]-2-[4-(1-benzimidazolyl)-2-methyl-2-butylamino]ethanol, 1-[2H-5-hydroxy-3-oxo-4H-1,4-benzoxazin-8-yl]-2-[3-(4-N,N-dimethylaminophenyl)-2-methyl-2-propylamino]ethanol, 1-[2H-5-hydroxy-3-oxo-4H-1,4-benzoxazin-8-yl]-2-[3-(4-methoxyphenyl)-2-methyl-2-propylamino]ethanol, 1-[2H-5-hydroxy-3-oxo-4H-1,4-benzoxazin-8-yl]-2-[3-(4-n-butyloxyphenyl)-2-methyl-2-propylamino]ethanol, 1-[2H-5-hydroxy-3-oxo-4H-1,4-benzoxazin-8-yl]-2-{4-[3-(4-methoxyphenyl)-1,2,4-triazol-3-yl]-2-methyl-2-butylamino}ethanol, 5-hydroxy-8-(1-hydroxy-2-isopropylaminobutyl)-2H-1,4-benzoxazin-3-(4H)-one, 1-(4-amino-3-chloro-5-trifluoromethylphenyl)-2-tert-butylamino)ethanol and 1-(4-ethoxycarbonylamino-3-cyano-5-fluorophenyl)-2-(tert-butylamino)ethanol optionally in the form of their racemates, their enantiomers, their diastereomers, and mixtures thereof, and optionally their pharmacologically-compatible acid addition salts and the compounds claimed in Spanish Patent application numbers P200501229 and P200601082. When the β2-agonists are in the form of a salt or derivative It is particularly preferred that it is in a form selected from the sodium salts, sulfobenzoates, phosphates, isonicotinates, acetates, propionates, dihydrogen phosphates, palmitates, pivalates, fumarates, furoates, xinafoates or mixtures thereof.

The following β2-agonists are of special interest for the combination with the compounds of formula (I): arformoterol, bambuterol, bitolterol, broxaterol, carbuterol, clenbuterol, dopexamine, fenoterol, formoterol, hexoprenaline, ibuterol, isoprenaline, levosalbutamol, mabuterol, meluadrine, nolomirole, orciprenaline, pirbuterol, procaterol, (R,R)-formoterol, reproterol, ritodrine, rimoterol, salbutamol, salmeterol, sibenadet, sulfonterol, terbutaline, tulobuterol, GSK-597901, GSK-159797, KUL-1248, TA-2005 and QAB-149 optionally in the form of their racemates, their enantiomers, their diastereomers, and mixtures thereof, and optionally their pharmacologically-compatible acid addition salts Still most preferred are the following β2-agonists: formoterol, salmeterol and GSK-597901, GSK-159797, QAB-149 optionally in the form of their racemates, their enantiomers, their diastereomers and mixtures thereof, and optionally their pharmacologically-compatible acid addition salts. Still more preferred are salmeterol and formoterol.

Examples of suitable PDE4 inhibitors that can be combined with the inhibitors of the p38 mitogen-activated protein kinase of the present invention are denbufylline, rolipram, cipamfylline, arofylline, filaminast, piclamilast, mesopram, drotaverine hydrochloride, lirimilast, cilomilast, 6-[2-(3,4-Diethoxyphenyl)thiazol-4-yl]pyridine-2-carboxylic acid, (R)-(+)-4-[2-(3-Cyclopentyloxy-4-methoxyphenyl)-2-phenylethyl]pyridine, N-(3,5-Dichloro-4-pyridinyl)-2-[1-(4-fluorobenzyl)-5-hydroxy-1H-indol-3-yl]-2-oxoacetamide, 9-(2-Fluorobenzyl)-N-6-methyl-2-(trifluoromethyl)adenine, N-(3,5-Dichloro-4-pyridinyl)-8-methoxyquinoline-5-carboxamide, N-[9-Methyl-4-oxo-1-phenyl-3,4,6,7-tetrahydropyrrolo[3,2,1-jk][1,4]benzodiazepin-3(R)-yl]pyridine-4-carboxamide, 3-[3-(Cyclopentyloxy)-4-methoxybenzyl]-6-

(ethylamino)-8-isopropyl-3H-purine hydrochloride, 4-[6,7-Diethoxy-2,3-bis(hydroxymethyl)naphthalen-1-yl]-1-(2-methoxyethyl)pyridin-2(1H)-one, 2-carbomethoxy-4-cyano-4-(3-cyclopropylmethoxy-4-difluororomethoxyphenyl)cyclohexan1-one, cis[4-cyano-4-(3-cyclopropylmethoxy-4-difluoromethoxyphenyl) cyclohexan-1-ol, ONO-6126 (Eur Respir J 2003, 22(Suppl. 45): Abst 2557) and the compounds claimed in the PCT patent application numbers WO03/097613, WO2004/058729 A1 and WO 2005/049581 A1.

Examples of suitable corticosteroids and glucocorticoids that can be combined with the inhibitors of the p38 mitogen-activated protein kinase of the present invention are prednisolone, methylprednisolone, dexamethasone, naflocort, deflazacort, halopredone acetate, budesonide, beclomethasone dipropionate, hydrocortisone, triamcinolone acetonide, fluocinolone acetonide, fluocinonide, clocortolone pivalate, methylprednisolone aceponate, dexamethasone palmitoate, tipredane, hydrocortisone aceponate, prednicarbate, alclometasone dipropionate, halometasone, methylprednisolone suleptanate, mometasone furoate, rimexolone, prednisolone farnesylate, ciclesonide, deprodone propionate, fluticasone propionate, halobetasol propionate, loteprednol etabonate, betamethasone butyrate propionate, flunisolide, prednisone, dexamethasone sodium phosphate, triamcinolone, betamethasone 17-valerate, betamethasone, betamethasone dipropionate, hydrocortisone acetate, hydrocortisone sodium succinate, prednisolone sodium phosphate and hydrocortisone probutate.

Examples of suitable CysLT1 and/or CysLT2 antagonists that can be combined with the inhibitors of the p38 mitogen-activated protein kinase of the present invention are tomelukast, Ibudilast, pobilukast, pranlukast hydrate, zafirlukast, ritolukast, verlukast, sulukast, tipelukast, cinalukast, iralukast sodium, masilukast, montelukast sodium, 5-[3-[3-(2-Quinolinylmethoxy)phenoxy]propyl]-1H-tetrazole, (E)-8-[2-[4-[4-(4-Fluorophenyl)butoxy]phenyl]vinyl]-2-(1H-tetrazol-5-yl)-4H-benzopyran-4-one sodium salt, 2-[N-[4-(4-Chlorophenylsulfonamido)butyl]-N-[3-(4-isopropylthiazol-2-ylmethoxy)benzyl]sulfamoyl]benzoic acid, (3R,4R)-3-[6-(5-Fluorobenzothiazol-2-ylmethoxy)-4-hydroxy-3,4-dihydro-2H-1-benzopyran-3-ylmethyl]benzoic acid, 2-[2-[2-(4-tert-Butylthiazol-2-yl)benzofuran-5-yloxymethyl]phenyl]acetic acid hydrochloride, 5-[2-[4-(Quinolin-2-ylmethoxy)phenoxymethyl]benzyl]-1H-tetrazole, (E)-2,2-Diethyl-3'-[2-[2-(4-isopropyl)thiazolyl]ethenyl]succinanilic acid; 4-[4-[3-(4-Acetyl-3-hydroxy-2-propylphenoxy)propylsulfonyl]phenyl]-4-oxobutyric acid, [[5-[[3-(4-Acetyl-3-hydroxy-2-propylphenoxy)propyl]thio]-1,3,4-thiadiazol-2-yl]thio]acetic acid, 9-[(4-Acetyl-3-hydroxy-2-n-propylphenoxy)methyl]-3-(1H-tetrazol-5-yl)-4H-pyrido[1,2-a]pyrimidin-4-one, 5-[3-[2-(7-Chloroquinolin-2-yl)vinyl]phenyl]-8-(N,N-dimethylcarbamoyl)-4,6-dithiaoctanoic acid sodium salt; 3-[1-[3-[2-(7-Chloroquinolin-2-yl)vinyl]phenyl]-1-[3-(dimethylamino)-3-oxopropylsulfanyl]methylsulfanyl]propionic acid sodium salt, 6-(2-Cyclohexylethyl)-[1,3,4]thiadiazolo[3,2-a]-1,2,3-triazolo[4,5-d]pyrimidin-9(1H)-one, (R)-3-[2-Methoxy-4-[N-(2-methylphenylsulfonyl)carbamoyl]benzyl]-1-methyl-N-(4,4,4-trifluoro-2-methylbutyl)indole-5-carboxamide, MCC-847 (from AstraZeneca), (+)-4(S)-(4-Carboxyphenylthio)-7-[4-(4-phenoxybutoxy)phenyl]-5(Z)-heptenoic acid and the compounds claimed in PCT patent application WO2004/043966A1.

Examples of suitable inhibitors of egfr-kinase that can be combined with the inhibitors of the p38 mitogen-activated protein kinase of the present invention are palifermin, cetuximab, gefitinib, repifermin, erlotinib hydrochloride, canertinib dihydrochloride, lapatinib, and N-[4-(3-Chloro-4-fluorophenylamino)-3-cyano-7-ethoxyquinolin-6-yl]-4-(dimethylamino)-2(E)-butenamide.

Examples of suitable antagonists of the A2b adenosine receptor that can be combined with the inhibitors of the p38 mitogen-activated protein kinase of the present invention are CVT-6883 from CV Therapeutics, 4-(1-butylxanthin-8-yl) benzoic acid, 8-[1-[3-(4-chlorophenyl)-1,2,4-oxadiazol-5-ylmethyl]-1H-pyrazol-4-yl]-1,3-dipropylxanthine, N-(1,3-benzodioxol-5-yl)-2-[5-(1,3-dipropylxanthin-8-yl)-1-methyl-1H-pyrazol-3-yloxy]acetamide, 8-[4-[5-(2-methoxyphenyl)-1,2,4-oxadiazol-3-ylmethoxy]phenyl]-1,3-dipropylxanthine, 3-[5-(2-methyl-1H-imidazol-1-yl)-2-(pyrazin-2-ylamino)thiazol-4-yl]benzonitrile, 4-(2,6-dioxo-1-propyl-2,3,6,7-tetrahydro-1H-purin-8-yl)benzenesulfonic acid, 1-[2-[8-(3-fluorophenyl)-9-methyl-9H-adenin-2-yl] ethynyl]cyclopentanol hydrochloride, N-(2-acetylphenyl)-2-[4-(1,3-dipropylxanthin-8-yl)phenoxy]acetamide, N-(4-acetylphenyl)-2-[4-(1,3-dipropylxanthin-8-yl)phenoxy] acetamide, N-(4-cyanophenyl)-2-[4-(1,3-dipropylxanthin-8-yl)phenoxy]acetamide, 4-(3,4-dichlorophenyl)-5-(4-pyridinyl)thiazol-2-amine or the compounds of international patent applications WO 2005/040155 A1, WO2005/100353 A1 and Spanish patent applications P200502433 and P200501876.

Examples of suitable NK1-receptor antagonists that can be combined with the inhibitors of the p38 mitogen-activated protein kinase of the present invention are nolpitantium besilate, dapitant, lanepitant, vofopitant hydrochloride, aprepitant, ezlopitant, N-[3-(2-Pentylphenyl)propionyl]-threonyl-N-methyl-2,3-dehydrotyrosyl-leucyl-D-phenylalanyl-allothreonyl-asparaginyl-serine C-1.7-O-3.1 lactone, 1-Methylindol-3-ylcarbonyl-[4(R)-hydroxy]-L-proly-[3-(2-naphthyl)]-L-alanine N-benzyl-N-methylamide, (+)-(2S, 3S)-3-[2-Methoxy-5-(trifluoromethoxy)benzylamino]-2-phenylpiperidine, (2R,4S)—N-[1-[3,5-Bis(trifluoromethyl)benzoyl]-2-(4-chlorobenzyl)piperidin-4-yl]quinoline-4-carboxamide, 3-[2(R)-[1(R)-[3,5-Bis(trifluoromethyl) phenyl]ethoxy]-3(S)-(4-fluorophenyl)morpholin-4-ylmethyl]-5-oxo-4,5-dihydro-1H-1,2,4-triazole-1-phosphinic acid bis(N-methyl-D-glucamine) salt; [3-[2(R)-[1(R)-[3,5-bis(trifluoromethyl)phenyl]ethoxy]-3(S)-(4-fluorophenyl)-4-morpholinylmethyl]-2,5-dihydro-5-oxo-1H-1,2,4-triazol-1-yl]phosphonic acid 1-deoxy-1-(methylamino)-D-glucitol (1:2) salt, 1'-[2-[2(R)-(3,4-Dichlorophenyl)-4-(3,4,5-trimethoxybenzoyl)morpholin-2-yl]ethyl]spiro[benzo[c]thiophen-1(3H)-4'-piperidine]2(S)-oxide hydrochloride and the compound CS-003 described in Eur Respir J 2003, 22(Suppl. 45): Abst P2664.

Examples of suitable CRTh2 antagonists that can be combined with the inhibitors of the p38 mitogen-activated protein kinase of the present invention are 2-[5-Fluoro-2-methyl-1-[4-(methylsulfonyl)phenylsulfonyl]-1H-indol-3-yl]acetic acid, Ramatroban, [(3R)-4-(4-chlorobenzyl)-7-fluoro-5-(methylsulfonyl)-1,2,3,4tetrahydrocyclopenta[b]indol-3-yl] acetic acid and (1R,2R,3S,5S)-7-[2-(5-Hydroxybenzothiophen-3-ylcarboxamido)-6,6-dimethylbicyclo[3.1.1] hept-3-yl]-5(Z)-heptenoic acid Examples of suitable Syk kinase inhibitors that can be combined with the inhibitors of the p38 mitogen-activated protein kinase of the present invention are piceatannol, 2-(2-Aminoethylamino)-4-[3-(trifluoromethyl)phenylamino]pyrimidine-5-carboxamide, R-091 (from Rigel), R-112 (from Rigel), R-343 (from Rigel), R-788 (from Rigel), 6-[5-Fluoro-2-(3,4,5-trimethoxyphenylamino)pyrimidin-4-ylamino]-2, 2-dimethyl-3,4-dihydro-2H-pyrido[3,2-b][1,4]oxazin-3-one benzenesulfonate, 1-(2,4,6-Trihydroxyphenyl)-2-(4-methoxyphenyl)ethan-1-one, N-[4-[6-(Cyclobutylamino)-9H-purin-2-ylamino]phenyl]-N-methylacetamide, 2-[7-(3,4-Dimethoxyphenyl)imidazo[1,2-c]pyrimidin-5-ylamino] pyridine-3-carboxamide dihydrochloride and AVE-0950 (from Sanofi-Aventis).

Examples of CCR3 antagonists that can be combined with the inhibitors of the p38 mitogen-activated protein kinase of the present invention are 4-[3-[4-(3,4-Dichlorobenzyl)morpholin-2(S)-ylmethyl]ureidomethyl]benzamide, N-[1(R)-[4-(3,4-Dichlorobenzyl)piperidin-1-ylmethyl]-2-methylpropyl]-N'-(3,4,5-trimethoxyphenyl)urea, N-[1(S)-[4-(4-Chlorobenzyl)piperidin-1-ylmethyl]-2-hydroxypropyl]-N'-(3,4,5-trimethoxyphenyl)urea, 3-[3-(3-Acetylphenyl) ureido]-2-[4-(4-fluorobenzyl)piperidin-1-ylmethyl]-N-methylbenzamide, 4-(3,4-Dichlorobenzyl)-1-methyl-1-[3-methyl-2(R)-[3-(3,4,5-trimethoxyphenyl)ureido]butyl] piperidinium chloride, N-[2-[4(R)-(3,4-Dichlorobenzyl) pyrrolidin-2(S)-yl]ethyl]-2-[5-(3,4-dimethoxyphenyl) pyrimidin-2-ylsulfanyl]acetamide, CRIC-3 (from IPF Pharmaceuticals), 2(R)-[1-[1-(2,4-Dichlorobenzyl)-4(S)-(3-thienyl)pyrrolidin-3(S)-ylmethyl]piperidin-4-ylmethyl]pentanoic acid, 8-[1-(2,4-Dichlorobenzyl)-4(S)-(3-thienyl)pyrrolidin-3(S)-ylmethyl]-3,3-dipropyl-1-oxa-8-azaspiro[4.5] decane-2(S)-carboxylic acid, 11-[1-(2,4-Dichlorobenzyl)-4 (S)-(3-thienyl)pyrrolidin-3(S)-ylmethyl]-3,14-dioxa-11-azadispiro[5.1.5.2]pentadecane-15(S)-carboxylic acid, W-56750 (from Mitsubishi Pharma), N-[1(S)-[3endo-(4-Chlorobenzyl)-8-azabicyclo[3.2.1]oct-8-ylmethyl]-2(S)-hydroxypropyl]-N'-(3,4,5-trimethoxyphenyl)urea, N-(3-Acetylphenyl)-N'-[(1R,2S)-2-[3(S)-(4-fluorobenzyl) piperidin-1-ylmethyl]cyclohexyl]urea benzenesulfonate, trans-1-(Cycloheptylmethyl)-4-(2,7-dichloro-9H-xanthen-9-ylcarboxamido)-1-methylpiperidinium iodide, GW-782415 (from GlaxoSmithKline), GW-824575 (from GlaxoSmithKline), N-[1'-(3,4-Dichlorobenzyl)-1,4'-bipiperidin-3-ylmethyl]quinoline-6-carboxamide, N-[1-(6-Fluoronaphthalen-2-ylmethyl)pyrrolidin-3(R)-yl]-2-[1-(3-hydroxy-5-methylpyridin-2-ylcarbonyl)piperidin-4-ylidene] acetamide fumarate and DIN-106935 (from Bristol-Myers Squibb).

Examples of VLA-4 antagonists that can be combined with the inhibitors of the p38 mitogen-activated protein kinase of the present invention are N-[4-[3-(2-Methylphenyl)ureido] phenylacetyl]-L-leucyl-L-aspartyl-L-valyl-L-proline, 3(S)-[2(S)-[4,4-Dimethyl-3-[4-[3-(2-methylphenyl)ureido]benzyl]-2,5-dioxoimidazolidin-1-yl]-4-methylpentanoylamino]-3-phenylpropionic acid, 2(S)-(2,6-Dichlorobenzamido)-3-(2',6'-dimethoxybiphenyl-4-yl) propionic acid, RBx-4638 (from Ranbaxy), R-411 (from Roche), RBx-7796 (from Ranbaxy), SB-683699 (from GlaxoSmithKline), DW-908e (from Daiichi Pharmaceutical), RO-0270608 (from Roche), AJM-300 (from Ajinomoto), PS-460644 (from Pharmacopeia) and the compounds claimed in PCT patent application numbers WO 02/057242 A2 and WO 2004/099126 A1.

Examples of disease modifying antirheumatic drugs (DMARs) that can be combined with the inhibitors of the p38 mitogen-activated protein kinase of the present invention are auranofin, azathioprine, bucillamine, cyclosporine, iguratimod, leflunomide, methotrexate, pentostatin, rimacalib hydrochloride, romazarit, salazodine, sulphasalazine, teriflunomide, (E)-5-(3,5-Di-tert-butyl-4-hydroxybenzylidene)-2-ethylisothiazolidine 1,1-dioxide, cis-2-(4-Chlorophenyl)-4,5-diphenyl-4,5-dihydro-1H-imidazole hydrochloride, 2-[8-[2-[6-(Methylamino)pyridyl-2-ylethoxy]-3-oxo-2-(2,2, 2-trifluoroethyl)-2,3,4,5-tetrahydro-1H-2-benzazepin-4-(S)-yl]acetic acid, 4-acetoxy-2-(4-methylphenyl)benzothiazole, 3-[4-Methyl-3-[N-methyl-N-(7H-pyrrolo[2,3-d]pyrimidin-4-yl)amino]piperidin-1-yl]-3-oxopropionitrile (CP-690550), 3-Deazaadenosine, 6-[5-Fluoro-2-(3,4,5-trimethoxyphenylamino)pyrimidin-4-ylamino]-2,2-dimethyl-3,4-dihydro-2H-pyrido[3,2-b][1,4]oxazin-3-one benzenesulfonate (R-406), AD-452 from Sosei, AD-827 from Arakis, BB-2983 from British Biotech, SC-12267 from 4SC, CPH-82 from Conpharm, R-1295 from Roche, R-1503 from Roche and N2-[3-[1(S)-(2-Fluorobiphenyl-4-yl)ethyl]isoxazol-5-yl] morpholine-4-carboxamidine hydrochloride (SMP-114).

The combinations of the invention may be used in the treatment of disorders which are susceptible to amelioration by inhibition of the p38 mitogen-activated protein kinase. Thus, the present application encompasses methods of treatment of these disorders, as well as the use of the combinations of the invention in the manufacture of a medicament for the treatment of these disorders.

Preferred examples of such disorders are those respiratory diseases, wherein the use of bronchodilating agents is expected to have a beneficial effect, for example asthma, acute or chronic bronchitis, emphysema, or Chronic Obstructive Pulmonary Disease (COPD).

The active compounds in the combinations of the invention may be administered by any suitable route, depending on the nature of the disorder to be treated, e.g. orally (as syrups, tablets, capsules, lozenges, controlled-release preparations, fast-dissolving preparations, etc); topically (as creams, ointments, lotions, nasal sprays or aerosols, etc); by injection (subcutaneous, intradermic, intramuscular, intravenous, etc.) or by inhalation (as a dry powder, a solution, a dispersion, etc).

The active compounds in the combination, i.e. the inhibitors of the p38 mitogen-activated protein kinase of the invention, and the other optional active compounds may be administered together in the same pharmaceutical composition or in different compositions intended for separate, simultaneous, concomitant or sequential administration by the same or a different route.

One execution of the present invention consists of a kit of parts comprising an the inhibitors of the p38 mitogen-activated protein kinase of the present invention together with instructions for simultaneous, concurrent, separate or sequential use in combination with another active compound useful in the treatment of a respiratory disease which responds to inhibition of the p38 mitogen-activated protein kinase.

Another execution of the present invention consists of a package comprising an inhibitors of the p38 mitogen-activated protein kinase of formula (I) and another active compound useful in the treatment of a respiratory disease for the simultaneous, concurrent, separate or sequential use in the treatment of a respiratory disease which responds to the inhibition of the p38 mitogen-activated protein kinase.

In a preferred embodiment of the invention the active compounds in the combination are administered by inhalation through a common delivery device, wherein they can be formulated in the same or in different pharmaceutical compositions.

In the most preferred embodiment the inhibitors of the p38 mitogen-activated protein kinase of the invention and the other active compound as defined above are both present in the same pharmaceutical composition and are administered by inhalation through a common delivery device.

The pharmaceutical formulations may conveniently be presented in unit dosage form and may be prepared by any of the methods well known in the art of pharmacy. All methods include the step of bringing the active ingredient(s) into association with the carrier. In general the formulations are prepared by uniformly and intimately bringing into association the active ingredient with liquid carriers or finely divided solid carriers or both and then, if necessary, shaping the product into the desired formulation.

Formulations of the present invention suitable for oral administration may be presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion. The active ingredient may also be presented as a bolus, electuary or paste.

A syrup formulation will generally consist of a suspension or solution of the compound or salt in a liquid carrier for example, ethanol, peanut oil, olive oil, glycerine or water with flavouring or colouring agent.

Where the composition is in the form of a tablet, any pharmaceutical carrier routinely used for preparing solid formulations may be used. Examples of such carriers include magnesium stearate, talc, gelatine, acacia, stearic acid, starch, lactose and sucrose.

A tablet may be made by compression or moulding, optionally with one or more accessory ingredients. Compressed tablets may be prepared by compressing in a suitable machine the active ingredient in a free-flowing form such as a powder or granules, optionally mixed with a binder, lubricant, inert diluent, surface active or dispersing agent. Moulded tablets may be made by moulding in a suitable machine a mixture of the powdered compound moistened with an inert liquid diluent. The tablets may optionally be coated or scored and may be formulated so as to provide slow or controlled release of the active ingredient therein.

Where the composition is in the form of a capsule, any routine encapsulation is suitable, for example using the aforementioned carriers in a hard gelatine capsule. Where the composition is in the form of a soft gelatine capsule any pharmaceutical carrier routinely used for preparing dispersions or suspensions may be considered, for example aqueous gums, celluloses, silicates or oils, and are incorporated in a soft gelatine capsule.

Dry powder compositions for topical delivery to the lung by inhalation may, for example, be presented in capsules and cartridges of for example gelatine or blisters of for example laminated aluminium foil, for use in an inhaler or insufflator. Formulations generally contain a powder mix for inhalation of the compound of the invention and a suitable powder base (carrier substance) such as lactose or starch. Use of lactose is preferred. Each capsule or cartridge may generally contain between 2 µg and 150 µg of each therapeutically active ingredient. Alternatively, the active ingredient (s) may be presented without excipients.

Packaging of the formulation may be suitable for unit dose or multi-dose delivery. In the case of multi-dose delivery, the formulation can be pre-metered or metered in use. Dry powder inhalers are thus classified into three groups: (a) single dose, (b) multiple unit dose and (c) multi dose devices.

For inhalers of the first type, single doses have been weighed by the manufacturer into small containers, which are mostly hard gelatine capsules. A capsule has to be taken from a separate box or container and inserted into a receptacle area of the inhaler. Next, the capsule has to be opened or perforated with pins or cutting blades in order to allow part of the inspiratory air stream to pass through the capsule for powder entrainment or to discharge the powder from the capsule through these perforations by means of centrifugal force during inhalation. After inhalation, the emptied capsule has to be removed from the inhaler again. Mostly, disassembling of the inhaler is necessary for inserting and removing the capsule, which is an operation that can be difficult and burdensome for some patients. Other drawbacks related to the use of hard gelatine capsules for inhalation powders are (a) poor protection against moisture uptake from the ambient air, (b) problems with opening or perforation after the capsules have been exposed previously to extreme relative humidity, which causes fragmentation or indenture, and (c) possible inhalation of capsule fragments. Moreover, for a number of capsule inhalers, incomplete expulsion has been reported (e.g. Nielsen et al, 1997).

Some capsule inhalers have a magazine from which individual capsules can be transferred to a receiving chamber, in which perforation and emptying takes place, as described in WO 92/03175. Other capsule inhalers have revolving magazines with capsule chambers that can be brought in line with the air conduit for dose discharge (e.g. WO91/02558 and GB 2242134). They comprise the type of multiple unit dose inhalers together with blister inhalers, which have a limited number of unit doses in supply on a disk or on a strip.

Blister inhalers provide better moisture protection of the medicament than capsule inhalers. Access to the powder is obtained by perforating the cover as well as the blister foil, or by peeling off the cover foil. When a blister strip is used instead of a disk, the number of doses can be increased, but it is inconvenient for the patient to replace an empty strip. Therefore, such devices are often disposable with the incorporated dose system, including the technique used to transport the strip and open the blister pockets.

Multi-dose inhalers do not contain pre-measured quantities of the powder formulation. They consist of a relatively large container and a dose measuring principle that has to be operated by the patient. The container bears multiple doses that are isolated individually from the bulk of powder by volumetric displacement. Various dose measuring principles exist, including rotatable membranes (e.g. EP0069715) or disks (e.g. GB 2041763; EP 0424790; DE 4239402 and EP 0674533), rotatable cylinders (e.g. EP 0166294; GB 2165159 and WO 92/09322) and rotatable frustums (e.g. WO 92/00771), all having cavities which have to be filled with powder from the container. Other multi dose devices have measuring slides (e.g. U.S. Pat. No. 5,201,308 and WO 97/00703) or measuring plungers with a local or circumferential recess to displace a certain volume of powder from the container to a delivery chamber or an air conduit e.g. EP 0505321, WO 92/04068 and WO 92/04928.

Reproducible dose measuring is one of the major concerns for multi dose inhaler devices.

The powder formulation has to exhibit good and stable flow properties, because filling of the dose measuring cups or cavities is mostly under the influence of the force of gravity.

For reloaded single dose and multiple unit dose inhalers, the dose measuring accuracy and reproducibility can be guaranteed by the manufacturer. Multi dose inhalers on the other hand, can contain a much higher number of doses, whereas the number of handlings to prime a dose is generally lower.

Because the inspiratory air stream in multi-dose devices is often straight across the dose measuring cavity, and because the massive and rigid dose measuring systems of multi dose inhalers can not be agitated by this inspiratory air stream, the powder mass is simply entrained from the cavity and little de-agglomeration is obtained during discharge.

Consequently, separate disintegration means are necessary. However in practice, they are not always part of the inhaler design. Because of the high number of doses in multi-dose devices, powder adhesion onto the inner walls of the air conduits and the de-agglomeration means must be minimized and/or regular cleaning of these parts must be possible, without affecting the residual doses in the device. Some multi dose inhalers have disposable drug containers that can be replaced after the prescribed number of doses has been taken (e.g. WO 97/000703). For such semi-permanent multi dose inhalers with disposable drug containers, the requirements to prevent drug accumulation are even stricter.

Apart from applications through dry powder inhalers the compositions of the invention can be administered in aerosols which operate via propellant gases or by means of so-called atomisers, via which solutions of pharmacologically-active substances can be sprayed under high pressure so that a mist of inhalable particles results. The advantage of these atomisers is that the use of propellant gases can be completely dispensed with.

Such atomisers are described, for example, in PCT Patent Application No. WO 91/14468 and International Patent Application No. WO 97/12687, reference here being made to the contents thereof.

Spray compositions for topical delivery to the lung by inhalation may for example be formulated as aqueous solutions or suspensions or as aerosols delivered from pressurised packs, such as a metered dose inhaler, with the use of a suitable liquefied propellant. Aerosol compositions suitable for inhalation can be either a suspension or a solution and generally contain the active ingredient (s) and a suitable propellant such as a fluorocarbon or hydrogen-containing chlorofluorocarbon or mixtures thereof, particularly hydrofluoroalkanes, e.g. dichlorodifluoromethane, trichlorofluoromethane, dichlorotetra-fluoroethane, especially 1,1,1,2-tetrafluoroethane, 1,1,1,2,3,3,3-heptafluoro-n-propane or a mixture thereof. Carbon dioxide or other suitable gas may also be used as propellant. The aerosol composition may be excipient free or may optionally contain additional formulation excipients well known in the art such as surfactants eg oleic acid or lecithin and cosolvents eg ethanol. Pressurised formulations will generally be retained in a canister (eg an aluminium canister) closed with a valve (eg a metering valve) and fitted into an actuator provided with a mouthpiece.

Medicaments for administration by inhalation desirably have a controlled particle size. The optimum particle size for inhalation into the bronchial system is usually 1-10μ, preferably 2-5μ. Particles having a size above 20μ are generally too large when inhaled to reach the small airways. To achieve these particle sizes the particles of the active ingredient as produced may be size reduced by conventional means eg by micronisation. The desired fraction may be separated out by air classification or sieving. Preferably, the particles will be crystalline.

Achieving high dose reproducibility with micronised powders is difficult because of their poor flowability and extreme agglomeration tendency. To improve the efficiency of dry powder compositions, the particles should be large while in the inhaler, but small when discharged into the respiratory tract. Thus, an excipient such as lactose or glucose is generally employed. The particle size of the excipient will usually be much greater than the inhaled medicament within the present invention. When the excipient is lactose it will typically be present as milled lactose, preferably crystalline alpha lactose monohydrate.

Pressurized aerosol compositions will generally be filled into canisters fitted with a valve, especially a metering valve. Canisters may optionally be coated with a plastics material e.g. a fluorocarbon polymer as described in WO96/32150. Canisters will be fitted into an actuator adapted for buccal delivery.

Typical compositions for nasal delivery include those mentioned above for inhalation and further include non-pressurized compositions in the form of a solution or suspension in an inert vehicle such as water optionally in combination with conventional excipients such as buffers, anti-microbials, tonicity modifying agents and viscosity modifying agents which may be administered by nasal pump.

Typical dermal and transdermal formulations comprise a conventional aqueous or non-aqueous vehicle, for example a cream, ointment, lotion or paste or are in the form of a medicated plaster, patch or membrane.

Preferably the composition is in unit dosage form, for example a tablet, capsule or metered aerosol dose, so that the patient may administer a single dose.

The amount of each active which is required to achieve a therapeutic effect will, of course, vary with the particular active, the route of administration, the subject under treatment, and the particular disorder or disease being treated.

Effective doses are normally in the range of 2-2000 mg of active ingredient per day. Daily dosage may be administered in one or more treatments, preferably from 1 to 4 treatments, per day. Preferably, the active ingredients are administered once or twice a day.

Each dosage unit may contain for example from 0.1 mg to 1000 mg and preferably from 1 mg to 100 mg of a 1,7-naphthyridine or pyrido[3,4-d]pyrimidine derivative of the invention or a pharmaceutical acceptable salt thereof.

When combinations of actives are used, it is contemplated that all active agents would be administered at the same time, or very close in time. Alternatively, one or two actives could be taken in the morning and the other(s) later in the day. Or in another scenario, one or two actives could be taken twice daily and the other(s) once daily, either at the same time as one of the twice-a-day dosing occurred, or separately. Preferably at least two, and more preferably all, of the actives would be taken together at the same time. Preferably, at least two, and more preferably all actives would be administered as an admixture.

The active substance compositions according to the invention are preferably administered in the form of compositions for inhalation delivered with the help of inhalers, especially dry powder inhalers, however, any other form or parenteral or oral application is possible. Here, the application of inhaled compositions embodies the preferred application form, especially in the therapy of obstructive lung diseases or for the treatment of asthma.

The syntheses of the compounds of the invention and of the intermediates for use therein are illustrated by the following Examples (1 to 34) including Preparation Examples (Preparations 1-15) which do not limit the scope of the invention in any way.

$^1$H Nuclear Magnetic Resonance Spectra were recorded on a Varian Gemini 300 spectrometer. Melting points were recorded using a Büchi B-540 apparatus. The chromatographic separations were obtained using a Waters 2795 system equipped with a Symmetry C18 (2.1×100 mm, 3.5 mm) column. As detectors a Micromass ZMD mass spectrometer using ES ionization and a Waters 996 Diode Array detector were used. The mobile phase was formic acid (0.46 ml), ammonia (0.115 ml) and water (1000 ml) (A) and formic acid (0.4 ml), ammonia (0.1 ml), methanol (500 ml) and acetonitrile (500 ml) (B): initially from 0% to 95% of B in 20 min, and then 4 min. with 95% of B. The reequilibration time between two injections was 5 min. The flow rate was 0.4 ml/min. The injection volume was 5 μl. Diode array chromatograms were processed at 210 nm.

PREPARATIONS

Preparation 1

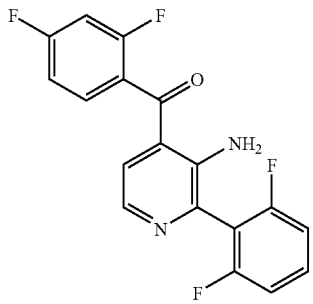

[3-Amino-2-(2,6-difluorophenyl)pyridin-4-yl](2,4-difluorophenyl)methanone a) 2,2-Dimethyl-N-pyridin-3-ylpropanamide To an ice-cooled solution of 3-aminopyridine (6 g, 63.8 mmol) and triethylamine (9.72 mL, 70.2 mmol) in 124 mL of dichloromethane under argon, was carefully added pivaloyl chloride (7.92 mL, 64.4 mmol) in 16 mL of dichloromethane. After the addition was completed, the reaction mixture was stirred at 0° C. for 15 minutes and then at room temperature for 18 hours. The mixture was washed with water, 4% aqueous sodium bicarbonate, brine, dried over sodium sulphate and the solvent removed under reduced pressure. The residue was purified by column chromatography on silica gel, using hexane/ethyl acetate (85:15) as eluent, to yield the title compound (8.5 g, 75%) as a white solid.

b) N-{4-[(2,4-Difluorophenyl)(hydroxy)methyl]pyridin-3-yl}-2,2-dimethylpropanamide nBuLi (2.5M in hexanes, 56 mL, 140 mmol) was added dropwise to a solution of the title compound of Preparation 1a (10 g, 56.2 mmol) in dry THF (140 mL) at −78° C. under argon and the resulting mixture was stirred at that temperature for 15 minutes and then at 0° C. for 3 hours. Then, the reaction mixture was cooled down to −78° C. and 2,4-difluoro-benzaldehyde (11.9 g, 84 mmol) in 14 mL of tetrahydrofuran was carefully added. After 15 minutes, the cooling bath was removed and the mixture was stirred overnight at room temperature. Subsequently, the mixture was poured into water (600 mL) and extracted with ethyl acetate (3×300 mL). The organic solution was washed with brine, dried over anhydrous sodium sulphate and the solvent removed under reduced pressure. The residue was purified by column chromatography on silica gel, using n-hexane/ethyl acetate (1:4 to 100% ethyl acetate) as eluent, to yield the title compound (9.5 g, 53%) as a white solid.

c) N-[4-(2,4-Difluorobenzoyl)pyridin-3-yl]-2,2-dimethylpropanamide

The title compound of Preparation 1b (20.1 g, 62.81 mmol) was dissolved in chloroform (550 mL) and activated manganese (IV) oxide (54.8 g, 628.1 mmol) was added portionwise over a 1 hour period. The suspension was then stirred at room temperature for 16 hours. The mixture was filtered through Celite®, the filter cake was washed with more chloroform and the combined filtrate and washings were evaporated to afford the title compound (19.9 g, 99%) as a solid.

d) (3-Aminopyridin-4-yl)(2,4-difluorophenyl)methanone

A solution of the title compound of Preparation 1c (19.9 g, 62.7 mmol) in 190 mL of ethanol was treated with aqueous 5N HCl (550 mL) and heated to 98° C. for 7 hours. The reaction mixture was cooled, poured into ice water and the pH adjusted to 9-10 with concentrated aqueous ammonia. The solution was extracted with ethyl acetate (4×200 mL) and the organic layer was washed with brine, dried over sodium sulphate and the solvent removed under reduced pressure to yield the title compound (12.2 g, 83%) as a yellowish solid.

e) (3-Amino-1-oxidopyridin-4-yl)(2,4-difluorophenyl)methanone

Meta-chloroperbenzoic acid (77%) (17.9 g, 79.82 mmol) was added portionwise to a solution of the title compound of Preparation 1d (12.2 g, 52.07 mmol) in dichloromethane (290 mL) at 0° C. and the reaction mixture was stirred overnight at room temperature. Then, more dichloromethane was added (2 L) and the solution was washed with 4% aqueous sodium bicarbonate (4×200 ml) and brine. The organic layer was dried over sodium sulphate and concentrated under reduced pressure to give a residue that was triturated in a mixture of hexane and ethyl acetate (9:1) and filtered to yield the title compound (9.4 g, 72%) as a bright yellow solid.

f) (3-Amino-2-bromopyridin-4-yl)(2,4-difluorophenyl)methanone

The title compound of Preparation 1e (9.4 g, 37.6 mmol) was dissolved in 350 mL of dry dichloromethane and phosphorus oxybromide (31.3 g, 109.2 mmol) was added portionwise. The mixture was stirred at 60° C. for 3 hours. The reaction was cooled, poured into ice water and the pH was adjusted to 10-11 with concentrated aqueous ammonia. The solution was extracted with ethyl acetate (2×500 mL) and the organic layer was washed with brine, dried over sodium sulphate and the solvent removed under reduced pressure. The residue was purified by column chromatography on silica gel, using n-hexane/ethyl acetate (4:1) as eluent, to yield the title compound (6.85 g, 58%) as a bright yellow solid.
$^1$H-NMR δ (CDCl$_3$): 6.75 (bs, 2H), 6.88-7.09 (m, 2H), 7.12 (dd, J=2 and 4 Hz, 1H), 7.45-7.56 (m, 1H), 7.70 (d, J=6 Hz, 1H).

g) [3-Amino-2-(2,6-difluorophenyl)pyridin-4-yl](2,4-difluorophenyl)methanone nBuLi (2.5M in hexanes, 0.56 mL) was added dropwise to a solution of 1,3-difluoro-benzene (146 mg, 1.28 mmol) in dry tetrahydrofuran (2 mL) at −78° C. under argon and the resulting mixture was stirred at that temperature for 30 minutes. Then, the reaction mixture was warmed to −50° C. and ZnCl$_2$ (0.5M in THF, 2.8 mL) was carefully added. After 20 minutes, the title compound from Preparation 1f (200 mg, 0.64 mmol, in 1.5 mL of THF) and tetrakis(triphenylphosphine)palladium(0) (66 mg, 0.06 mmol) were sequentially added. The mixture was then submitted to three vacuum-argon cycles and warmed, first to room temperature for 15 minutes and then to 40° C. for 48 hours. After this time the reaction was cooled and the solvent evaporated under reduced pressure. The resulting crude material was purified by column chromatography on silica gel using hexane/ethyl acetate (8:2 to 7:3) as eluent to yield the title compound (150 mg, 68%) as a yellow solid.

LRMS (m/z): 347 (M+1)$^+$.
Retention Time: 15 min.
$^1$H-NMR δ (CDCl$_3$): 6.20 (brs, 2H), 6.93-7.14 (m, 4H), 7.22 (dd, J=5.4 and 3.1 Hz, 1H), 7.39-7.59 (m, 2H), 8.08 (d, J=5.5 Hz, 1H).

Preparation 2

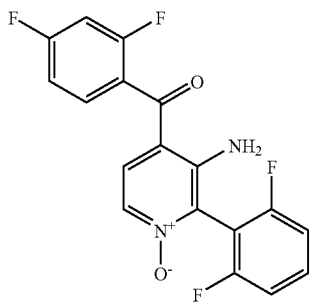

[3-Amino-2-(2,6-difluorophenyl)-1-oxidopyridin-4-yl]2,4-difluorophenyl)-methanone Meta-chloroperbenzoic acid (77%) (482 mg, 2.16 mmol) was added portionwise to a solution of the title compound from Preparation 1g (500 mg, 1.44 mmol) in dichloromethane (5.3 mL) at 0° C. and the reaction mixture was stirred overnight at room temperature. Then, more dichloromethane was added (50 mL) and the solution was washed with 4% aqueous sodium bicarbonate (3×30 ml) and brine. The organic layer was dried over sodium sulphate and concentrated under reduced pressure to give a residue that was purified by column chromatography on silica gel, using hexane/ethyl acetate (1:4) as eluent, to yield the title compound (380 mg, 73%) as a yellow solid.

LRMS (m/z): 363 (M+1)$^+$.
Retention Time: 13 min.
$^1$H-NMR δ (CDCl$_3$): 6.49 (brs, 2H), 6.92-7.17 (m, 4H), 7.27 (m, 1H), 7.46-7.60 (m, 2H), 7.67 (d, J=7.1 Hz, 1H).

Preparation 3

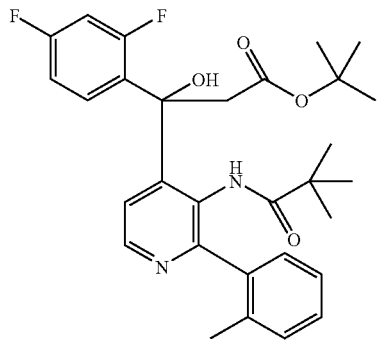

tert-Butyl 3-(2,4-difluorophenyl)-3-hydroxy-3-{3-[(2,2-dimethylpropanoyl)amino]-2-[2-methylphenyl]-4-yl}propanoate a) [3-Amino-2-(2-methylphenyl)pyridin-4-yl](2,4-difluorophenyl)methanone In a Schlenk tube were charged the compound of Preparation 1f (700 mg, 2.23 mmol), 2-methylphenyl boronic acid (456 mg, 3.39 mmol), cesium carbonate (2M aqueous solution, 3.35 mL, 6.7 mmol) and dioxane (18 mL). The mixture was submitted to three vacuum-argon cycles, then [1,1'-bis(diphenylphosphino)ferrocene]dichloropalladium(II) complex with dichloromethane (1:1) (127 mg, 0.15 mmol) was added and the mixture was purged in the same way. The reaction was stirred at 80° C. under argon for 17 h. Subsequently, water was added to the cold reaction mixture and it was extracted with ethyl acetate (3×50 ml) and the organic solution was washed with brine, dried over sodium sulphate and the solvent removed under reduced pressure. The residue was purified by column chromatography on silica gel, using hexane/ethyl acetate (5:1) as eluent, to yield the title compound (656 mg, 90%) as a yellow solid.

LRMS (m/z): 325 (M+1)$^+$.
Retention Time: 16 min.
$^1$H-NMR δ (CDCl$_3$): 2.21 (s, 3H), 6.17 (brs, 2H), 6.91-7.09 (m, 2H), 7.13 (dd, J=5.1 and 2.7 Hz, 1H), 7.31-7.37 (m, 4H), 7.48-7.59 (m, 1H), 8.00 (d, J=5.1 Hz, 1H).

b) 2,2-Dimethyl-N-[2-(2-methylphenyl)-4-(2,4-difluorobenzoyl)pyridin-3-yl]-propanamide To a solution of the title compound from Preparation 3a (2.3 g, 7.09 mmol) and diisopropyl ethyl amine (2.6 mL, 14.89 mmol) in dioxane (26 mL) under argon, was carefully added pivaloyl chloride (1.75 mL, 14.18 mmol). After the addition was complete, the reaction mixture was stirred in a sealed reactor at 110° C. for 6 hours. The mixture was allowed to cool to room temperature, diluted with ethyl acetate (500 mL) washed with 4% aqueous sodium bicarbonate, brine, dried over sodium sulphate and the solvent removed under reduced pressure. The residue was purified by column chromatography on silica gel, using hexane/ethyl acetate (3:1) as eluent, to yield the title compound (2.62 g, 89%) as a yellow solid.

LRMS (m/z): 409 (M+1)$^+$.
$^1$H-NMR δ (CDCl$_3$): 0.79 (s, 9H), 2.12 (s, 3H), 6.80-6.87 (m, 1H), 6.97-7.03 (m, 1H), 7.15 (brs, 1H), 7.26-7.28 (m, 1H), 7.32-7.42 (m, 4H), 7.90-7.98 (m, 1H), 8.65 (d, J=6 Hz, 1H).

c) tert-Butyl 3-(2,4-difluorophenyl)-3-hydroxy-3-{3-[(2,2-dimethylpropanoyl)amino]-2-[2-methylphenyl]-4-yl}propanoate nBuLi (1.6M in hexanes, 15.9 mL) was added dropwise to a solution of diisopropylamine (3.62 mL, 25.4 mmol) in dry tetrahydrofuran (20 mL) at −78° C. under argon and the resulting mixture was stirred at that temperature for 10 minutes. The reaction mixture was stirred at room temperature for 20 minutes and cooled again to −78° C. Then, tert-butyl acetate (3.42 mL, 25.4 mmol) in 10 mL of dry tetrahydrofuran was carefully added and the reaction mixture stirred at −78° C. for 15 minutes. The title compound from Preparation 3b (2.62 g, 6.35 mmol in 20 mL of dry tetrahydrofuran) was added dropwise and the reaction stirred overnight, allowing it to slowly reach room temperature. After this period of time, the solvent was evaporated, water was added to the reaction mixture and it was extracted with ethyl acetate (3×50 ml), the combined organic solutions were washed with brine, dried over sodium sulphate and the solvent removed under reduced pressure to afford the title compound (3.77 g, 98%) as a brownish oil.

LRMS (m/z): 525 (M+1)$^+$.

$^1$H-NMR δ (CDCl$_3$): 0.72 (s, 9H), 1.44 (s, 9H), 2.26 (s, 3H), 3.29-3.36 (m, 2H), 6.31 (brs, 1H), 6.74 (m, 1H), 6.85 (m, 1H), 7.10-7.23 (m, 4H), 7.52 (m, 1H), 8.08 (brs, 1H), 8.55 (d, J=6 Hz, 1H).

Preparation 4

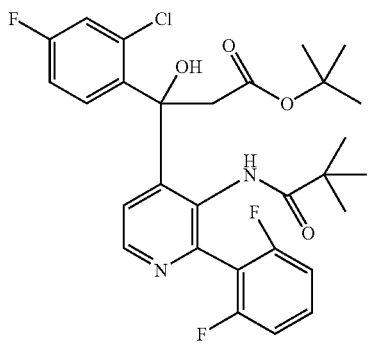

tert-Butyl 3-(2-chloro-4-fluorophenyl)-3-hydroxy-3-{3-[(2,2-dimethylpropanoyl)-amino]-2-[2,6-difluorophenyl]-4-yl}propanoate a) N-{-4-[(2-Chloro-4-fluorophenyl)(hydroxy)methyl]pyridin-3-yl}-2,2-dimethyl-propanamide nBuLi (2.5M in hexanes, 56.2 mL, 140.5 mmol) was added dropwise to a solution of the title compound of Preparation 1a (10 g, 56.2 mmol) and N,N,N',N'-tetramethylethylene-diamine (TMEDA) (20.9 mL, 140.5 mmol) in diethyl ether (338 mL) at −78° C. under argon and the resulting mixture was stirred at that temperature for 15 minutes and then at −10° C. for 2 hours. Then, the reaction mixture was cooled to −78° C. and 2-chloro-4-fluorobenzaldehyde (20 g, 140.5 mmol) in 34 mL of dry tetrahydrofuran was carefully added. After 15 minutes, the cooling bath was removed and the mixture stirred overnight at room temperature. Subsequently, water (100 mL) was added to the flask and it was extracted with ethyl acetate (3×200 mL), the organic solution was washed with brine, dried over sodium sulphate and the solvent removed under reduced pressure. The residue was purified by column chromatography on silica gel, using dichloromethane/ethyl acetate (7:3) as eluent, to yield the title compound (6.15 g, 33%) as a solid.

b) N-[4-(2-Chloro-4-fluorobenzoyl)pyridin-3-yl]-2,2-dimethylpropanamide

Obtained as a yellow solid (99%) from the title compound of Preparation 4a following the experimental procedure described in Preparation 1c.

c) (3-Aminopyridin-4-yl)(2-chloro-4-fluorophenyl)methanone

Obtained as a bright yellow solid (92%) from the title compound of Preparation 4b following the experimental procedure described in Preparation 1d.

d) (3-Amino-1-oxidopyridin-4-yl)(2-chloro-4-fluorophenyl)methanone

Obtained as a bright yellow solid (83%) from the title compound of Preparation 4c following the experimental procedure described in Preparation 1e.

e) (3-Amino-2-bromopyridin-4-yl)(2-chloro-4-fluorophenyl)methanone

Obtained as a bright yellow solid (46%) from the title compound of Preparation 4d following the experimental procedure described in Preparation 1f.

$^1$H-NMR δ (CDCl$_3$): 6.88 (brs, 2H), 6.96 (d, J=6 Hz, 1H), 7.08-7.17 (m, 1H), 7.23 (dd, J=2 and 8 Hz, 1H), 7.34 (dd, J=6 and 10 Hz, 1H), 7.65 (d, J=6 Hz, 1H).

f) [3-Amino-2-(2,6-difluorophenyl)pyridin-4-yl](2-chloro-4-fluorophenyl)methanone Obtained as a yellow solid (93%) from the title compound of Preparation 4e and 1,3-difluorobenzene following the experimental procedure described in Preparation 1g.

$^1$H-NMR δ (CDCl$_3$): 6.32 (brs, 2H), 7.03-7.18 (m, 4H), 7.27 (dd, J=2 and 8 Hz, 1H), 7.36-7.55 (m, 2H), 8.03 (d, J=6 Hz, 1H).

g) 2,2-Dimethyl-N-[2-(2,6-difluorophenyl)-4-(2-chloro-4-fluorobenzoyl)pyridin-3-yl]-propanamide Obtained as a bright yellow solid (87%) from the title compound of Preparation 4f following the experimental procedure described in Preparation 3b.

LRMS (m/z): 447, 449 (M+1)$^+$.

$^1$H-NMR δ (CDCl$_3$): 0.97 (s, 9H), 7.01-7.13 (m, 3H), 7.23 (dd, J=3 and 9 Hz, 1H), 7.34 (d, J=6 Hz, 1H), 7.38-7.44 (m, 1H), 7.67 (dd, J=6 and 9 Hz, 1H), 8.16 (brs, 1H), 8.72 (d, J=6 Hz, 1H).

h) tert-Butyl 3-(2-chloro-4-fluorophenyl)-3-hydroxy-3-{3-[(2,2-dimethylpropanoyl)-amino]-2-[2,6-difluorophenyl]-4-yl}propanoate Obtained as a white solid (93%) from the title compound of in Preparation 4g following the experimental procedure described in Preparation 3c.

LRMS (m/z): 563, 565 (M+1)$^+$.

¹H-NMR δ (CDCl₃): 0.71 (s, 9H), 1.47 (s, 9H), 3.21-3.37 (m, 2H), 6.30 (brs, 1H), 6.86 (m, 1H), 6.92-6.98 (m, 2H), 7.08 (m, 1H), 7.25 (m, 1H), 7.51 (m, 1H), 8.25 (brs, 1H), 8.58 (d, J=6 Hz, 1H).

Preparation 5

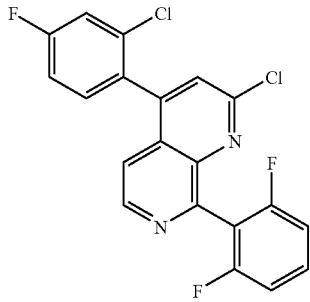

2-Chloro-4-(2-chloro-4-fluorophenyl)-8-(2,6-difluorophenyl)-1,7-naphthyridine

The title compound from Example 7 (152 mg, 0.37 mmol) was suspended in phosphorus oxychloride (1.60 mL) and the mixture was stirred at 110° C. for 19 hours. Subsequently, the cooled reaction mixture was poured into a mixture of ethyl acetate-ice and basified to pH 7-8 with saturated aqueous potassium carbonate. The aqueous layer was extracted with ethyl acetate (3×50 mL) and the combined organic layers washed with water, brine and dried over anhydrous sodium sulphate. Removal of the solvent under reduced pressure afforded the title compound (140 mg, 91%) as a beige solid.

LRMS (m/z): 405, 407, 409 (M+1)⁺.

¹H-NMR δ (CDCl₃): 7.05-7.12 (m, 2H), 7.18-7.24 (m, 1H), 7.34-7.40 (m, 3H), 7.42-7.50 (m, 1H), 7.51 (s, 1H), 8.72 (d, J=6 Hz, 1H).

Preparation 6

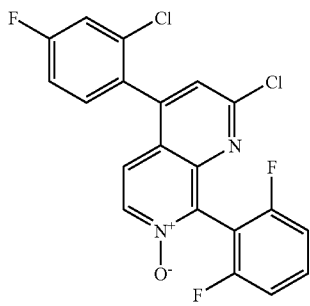

2-Chloro-4-(2-chloro-4-fluorophenyl)-8-(2,6-difluorophenyl)-1,7-naphthyridine 7-oxide Obtained as a light-brown solid (26%) from the title compound of Example 8 following the experimental procedure described in Preparation 5.

LRMS (m/z): 421, 423, 425 (M+1)⁺.

Preparation 7

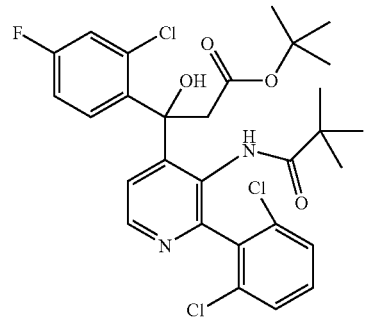

tert-Butyl 3-(2-chloro-4-fluorophenyl)-3-hydroxy-3-{3-[(2,2-dimethylpropanoyl)-amino]-2-[2,6-dichlorophenyl]-4-yl}propanoate a) [3-Amino-2-(2,6-dichlorophenyl)pyridin-4-yl](2-chloro-4-fluorophenyl)methanone In a Schlenk tube were charged the compound of Preparation 4e (7.33 g, 22.24 mmol), 2,6-dichlorophenyl boronic acid (8.6 g, 45.07 mmol), potassium phosphate (14.2 g, 66.9 mmol) and toluene (140 mL). The mixture was submitted to three vacuum-argon cycles, then 2-(dicyclohexylphosphino) 2',6'-dimethoxy-1-1'biphenyl (S-PHOS) (0.92 g, 2.24 mmol) and tris(dibenzylideneacetone)dipalladium(0) (1.24 g, 1.35 mmol) were added and the mixture purged in the same way. The reaction was stirred at 110° C. under argon for 3 days. Subsequently, the cold reaction mixture was filtered through Celite® and washed with more toluene (60 mL). The residue was directly purified by column chromatography on silica gel, using hexane/diethyl ether (9:1 to 2:8) as eluent, to yield the title compound (3.01 g, 34%) as a yellow solid.

LRMS (m/z): 395, 397, 399, 401 (M+1)⁺.

¹H-NMR δ (CDCl₃): 6.16 (brs, 2H), 7.07 (d, J=6 Hz, 1H), 7.11-7.18 (m, 1H), 7.25-7.29 (m, 1H), 7.35-7.45 (m, 2H), 7.48-7.52 (m, 2H), 8.04 (d, J=6 Hz, 1H).

b) 2,2-Dimethyl-N-[2-(2,6-dichlorophenyl)-4-(2-chloro-4-fluorobenzoyl)pyridin-3-yl]-propanamide Obtained as a light-brown solid (73%) from the title compound of Preparation 7a following the experimental procedure described in Preparation 3b.

LRMS (m/z): 479, 481, 483, 485 (M+1)⁺.

¹H-NMR δ (CDCl₃): 0.85 (s, 9H), 7.04-7.10 (m, 1H), 7.17 (d, J=9 Hz, 1H), 7.33-7.39 (m, 2H), 7.46-7.50 (m, 3H), 7.71-7.76 (m, 1H), 8.74 (d, J=6 Hz, 1H).

c) tert-Butyl 3-(2-chloro-4-fluorophenyl)-3-hydroxy-3-{3-[(2,2-dimethylpropanoyl)-amino]-2-[2,6-dichlorophenyl]-4-yl}propanoate Obtained as a brownish solid (99%) from the title compound of Preparation 7b following the experimental procedure described in Preparation 3c.

LRMS (m/z): 595. 597, 599, 601 (M+1)⁺.

¹H-NMR δ (CDCl₃): 0.70 (s, 9H), 1.43 (s, 9H), 3.20 (d, J=15 Hz, 1H), 3.39 (d, J=15 Hz, 1H), 6.29 (brs, 1H), 6.97-

7.08 (m, 2H), 7.16-7.21 (m, 1H), 7.30 (d, J=9 Hz, 1H), 7.35-7.38 (m, 2H), 7.70-7.75 (m, 2H), 8.63 (d, J=6 Hz, 1H).

Preparation 8

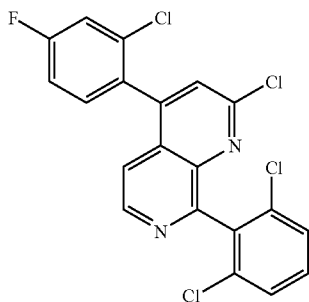

2-Chloro-4-(2-chloro-4-fluorophenyl)-8-(2,6-dichlorophenyl)-1,7-naphthyridine

Obtained as a white solid (80%) from the title compound of Example 11 following the experimental procedure described in Preparation 5.

LRMS (m/z): 437, 439, 441, 443 (M+1)$^+$.

$^1$H-NMR δ (CDCl$_3$): 7.20-7.25 (m, 1H), 7.37-7.44 (m, 4H), 7.47-7.52 (m, 3H), 8.73 (d, J=6 Hz, 1H).

Preparation 9

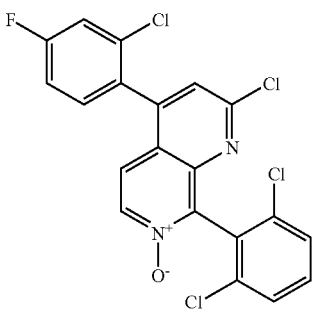

2-Chloro-4-(2-chloro-4-fluorophenyl)-8-(2,6-dichlorophenyl)-1,7-naphthyridine 7-oxide Obtained as a light-brown solid (67%) from the title compound of Example 12 following the experimental procedure described in Preparation 5.

LRMS (m/z): 453, 455, 457, 459 (M+1)$^+$.

$^1$H-NMR δ (CDCl$_3$): 7.20-7.24 (m, 1H), 7.35-7.48 (m, 5H), 7.50-7.55 (m 2H), 8.30 (d, J=6 Hz, 1H).

Preparation 10

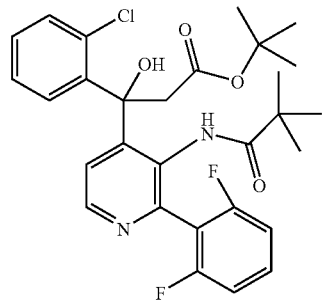

tert-Butyl 3-(2-chlorophenyl)-3-hydroxy-3-{3-[(2,2-dimethylpropanoyl)amino]-2-[2,6-difluorophenyl]-4-yl}propanoate a) N-{4-[(2-Chlorophenyl)(hydroxy)methyl]pyridin-3-yl}-2,2-dimethylpropanamide nBuLi (2.5M in hexanes, 30 mL, 75 mmol) was added dropwise to a solution of the title compound of Preparation 1a (5 g, 28.3 mmol) in dry tetrahydrofuran (70 mL) at −78° C. under argon and the resulting mixture was stirred at that temperature for 15 minutes and then at 0° C. for 3 hours. Then, the reaction mixture was cooled to −78° C. and 2-chloro-benzaldehyde (4.93 g, 43.4 mmol) in 7 mL of tetrahydrofuran was carefully added. After 15 minutes, the cooling bath was removed and the mixture stirred overnight at room temperature. Subsequently, the mixture was poured into water (300 mL) and extracted with ethyl acetate (3×300 mL). The organic solution was washed with brine, dried over anhydrous sodium sulphate and the solvent removed under reduced pressure. The residue was purified by column chromatography on silica gel, using n-hexane/ethyl acetate (1:4) as eluent, to yield the title compound (2.98 g, 33%) as a white solid.

b) N-[4-(2-Chlorobenzoyl)pyridin-3-yl]-2,2-dimethylpropanamide)

Obtained as a yellow solid (97%) from the title compound of Preparation 10a following the experimental procedure described in Preparation 1c.

c) (3-Aminopyridin-4-yl)(2-chlorophenyl)methanone

Obtained as a bright yellow solid (95%) from the title compound of Preparation 10b following the experimental procedure described in Preparation 1d.

d) (3-Amino-1-oxidopyridin-4-yl)(2-chlorophenyl)methanone

Obtained as a bright yellow solid (88%) from the title compound of Preparation 10c following the experimental procedure described in Preparation 1e.

e) (3-Amino-2-bromopyridin-4-yl)(2-chlorophenyl)methanone

Obtained as a bright yellow solid (57%) from the title compound of Preparation 10d following the experimental procedure described in Preparation 1f.

¹H-NMR δ (CDCl₃): 6.90 (bs, 2H), 6.98 (d, J=6 Hz, 1H), 7.29-7.49 (m, 4H), 7.64 (d, J=6 Hz, 1H).

f) [3-Amino-2-(2,6-difluorophenyl)pyridin-4-yl](2-chlorophenyl)methanone

Obtained as a yellow solid (46%) from the title compound of Preparation 10e and 1,3-difluorobenzene following the experimental procedure described in Preparation 1g.
LRMS (m/z): 345-347 (M+1)⁺.
Retention Time: 15 min.
¹H-NMR δ (CDCl₃): 6.34 (brs, 2H), 7.05-7.13 (m, 3H), 7.38-7.51 (m, 5H), 8.03 (d, J=6 Hz, 1H).

g) 2,2-Dimethyl-N-[2-(2,6-difluorophenyl)-4-(2-chlorobenzoyl)pyridin-3-yl]-propanamide Obtained as a orange solid (99%) from the title compound of Preparation 10f following the experimental procedure described in Preparation 3b.
LRMS (m/z): 429, 431 (M+1)⁺.
¹H-NMR δ (CDCl₃): 0.97 (s, 9H), 6.99-7.05 (m, 2H), 7.35-7.41 (m, 3H), 7.47-7.49 (m, 2H), 7.59 (d, J=6 Hz, 1H), 8.45 (brs, 1H), 8.71 (d, J=6 Hz, 1H).

h) tert-Butyl 3-(2-chlorophenyl)-3-hydroxy-3-{3-[(2,2-dimethylpropanoyl)amino]-2-[2,6-difluorophenyl]-4-yl}propanoate Obtained as a beige solid (93%) from the title compound of Preparation 10g following the experimental procedure described in Preparation 3c.
LRMS (m/z): 545, 547 (M+1)⁺.
¹H-NMR δ (CDCl₃): 0.68 (s, 9H), 1.45 (s, 9H), 3.26-3.39 (m, 2H), 6.27 (brs, 1H), 6.86 (t, J=9 Hz, 1H), 6.95 (t. J=9 Hz, 1H), 7.20-7.33 (m, 4H), 7.52-7.55 (m, 1H), 8.28 (brs, 1H), 8.57 (d, J=6 Hz, 1H).

Preparation 11

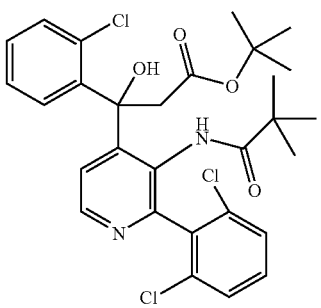

tert-Butyl 3-(2-chlorophenyl)-3-hydroxy-3-{3-[(2,2-dimethylpropanoyl)amino]-2-[2,6-dichlorophenyl]-4-yl}propanoate a) [3-Amino-2-(2,6-dichlorophenyl)pyridin-4-yl](2-chlorophenyl)methanone Obtained as a yellow solid (46%) from the title compound of Preparation 10e and 2,6-dichlorophenylboronic acid following the experimental procedure described in Preparation 7a.
LRMS (m/z): 377, 379, 381, 383 (M+1)⁺.

¹H-NMR δ (CDCl₃): 6.18 (brs, 2H), 7.09 (d, J=4 Hz, 1H), 7.34-7.43 (m, 3H), 7.47-7.53 (m, 4H), 8.03 (d, J=4 Hz, 1H).

b) 2,2-Dimethyl-N-[2-(2,6-dichlorophenyl)-4-(2-chlorobenzoyl)pyridin-3-yl]-propanamide Obtained as a bright yellow solid (97%) from the title compound of Preparation 11a following the experimental procedure described in Preparation 3b.
LRMS (m/z): 461, 463, 465, 467 (M+1)⁺.

c) tert-Butyl 3-(2-chlorophenyl)-3-hydroxy-3-{3-[(2,2-dimethylpropanoyl)amino]-2-[2,6-dichlorophenyl]-4-yl}propanoate Obtained as a white solid (99%) from the title compound of Preparation 11b following the experimental procedure described in Preparation 3c.
LRMS (m/z): 577, 579, 581, 583 (M+1)⁺.

Preparation 12

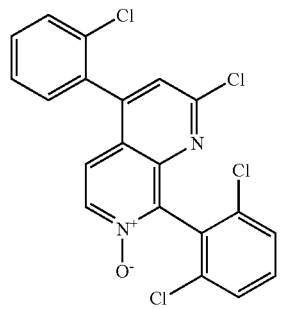

2-Chloro-4-(2-chlorophenyl)-8-(2,6-dichlorophenyl)-1,7-naphthyridine 7-oxide

Obtained as a yellow solid (67%) from the title compound of Example 18 following the experimental procedure described in Preparation 5.
LRMS (m/z): 435, 437, 439, 441 (M+1)⁺.
¹H-NMR δ (CDCl₃): 7.36-7.41 (m, 3H), 7.44-7.57 (m, 5H), 7.58-7.64 (m, 1H), 8.28 (d, J=6 Hz, 1H).

Preparation 13

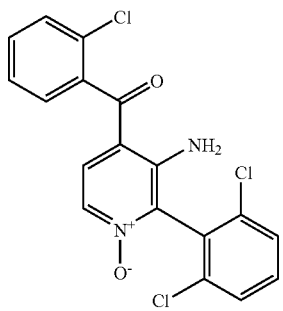

[3-Amino-2-(2,6-dichlorophenyl)-1-oxidopyridin-4-yl](2-chlorophenyl)methanone

Obtained as a yellow solid (61%) from the title compound of Preparation 11a following the experimental procedure described in Preparation 2a.

LRMS (m/z): 393, 395, 397, 399 (M+1)$^+$.

$^1$H-NMR δ (CDCl$_3$): 6.42 (brs, 2H), 7.13 (d, J=6 Hz, 1H), 7.40-7.57 (m, 7H), 7.61 (d, J=6 Hz, 1H).

Preparation 14

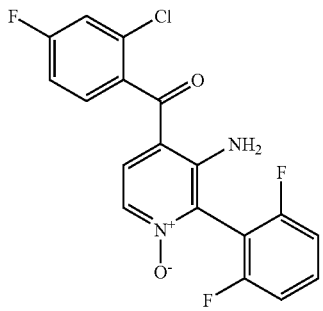

[3-Amino-2-(2,6-difluorophenyl)-1-oxidopyridin-4-yl](2-chloro-4-fluorophenyl)-methanone Obtained as a yellow solid (98%) from the title compound of Preparation 4f following the experimental procedure described in Preparation 2a.

LRMS (m/z): 379 (M+1)$^+$.

$^1$H-NMR δ (CDCl$_3$): 6.56 (brs, 2H), 7.10-7.20 (m, 4H), 7.27 (dd, J=2 and 8 Hz, 1H), 7.36-7.44 (m, 1H), 7.49-7.61 (m, 1H), 7.65 (d, J=8 Hz, 1H).

Preparation 15

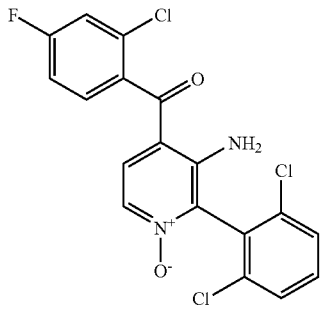

[3-Amino-2-(2,6-dichlorophenyl)-1-oxidopyridin-4-yl]2-chloro-4-fluorophenyl)-methanone Obtained as a yellow solid (76%) from the title compound of Preparation 7a following the experimental procedure described in Preparation 2a.

$^1$H-NMR δ (CDCl$_3$): 6.40 (brs, 2H), 7.12 (d, J=8 Hz, 1H), 7.11-7.20 (m, 1H), 7.26 (dd, J=2 and 8 Hz, 1H), 7.39-7.57 (m, 4H), 7.63 (d, J=8 Hz, 1H).

EXAMPLES

Example 1

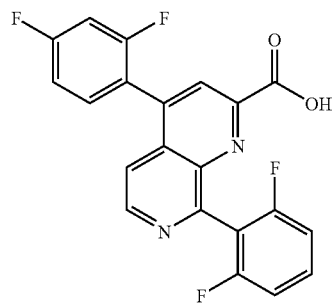

4-(2,4-Difluorophenyl)-8-(2,6-difluorophenyl)-1,7-naphthyridine-2-carboxylic acid Sulfuric acid 98% (0.053 mL, 1 mmol) was added to a suspension of the title compound as described in Preparation 1g (87 mg, 0.25 mmol), anhydrous magnesium sulphate (180 mg) and pyruvic acid (66 mg, 0.75 mmol) in 2.5 mL of toluene and the mixture was vigorously stirred in a pre-heated oil bath at 115° C. After 60 minutes, the reaction was cooled and the solvent decanted. The residue was dissolved in acetonitrile and filtered through sintered glass to eliminate most of the inorganic salts. The solvent was removed under reduced pressure and the oily material purified by column chromatography (C-18 silica from Waters©, reverse phase water/acetonitrile as eluent [0.1% v/v ammonium formate buffered, pH=3] 0% to 70%). The acetonitrile from the appropriate fractions was evaporated and the solid filtered and dried under reduced pressure to give the title compound as an off-white solid (60 mg, 60% yield).

LRMS (m/z): 399 (M+1)$^+$.

Example 2

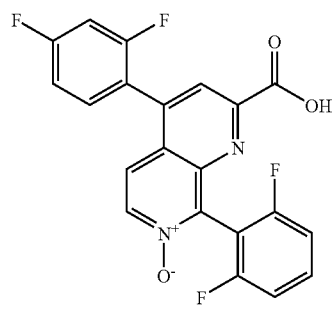

4-(2,4-Difluorophenyl)-8-(2,6-difluorophenyl)-1,7-naphthyridine-2-carboxylic acid 7-oxide Obtained as an off-white solid (55%) from the title compound of Preparation 2 following the experimental procedure described in Example 1.

LRMS (m/z): 415 (M+1)$^+$.

Example 3

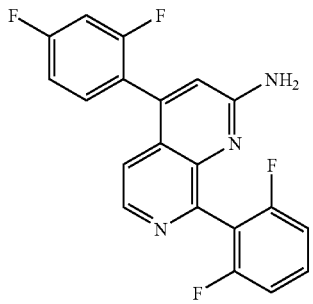

4-(2,4-Difluorophenyl)-8-(2,6-difluorophenyl)-1,7-naphthyridin-2-amine

To a suspension of the title compound from Example 1 (100 mg, 0.25 mmol) in tert-butanol (2.4 mL) were added diphenylphosphoryl azide (DPPA) (0.07 mL, 0.32 mmol) and triethylamine (0.045 mL, 0.32 mmol). The mixture was heated at 100° C. for 75 minutes. The solvent was evaporated and the mixture redissolved in HCl (4M in dioxane, 2 mL) and stirred at room temperature for 2.5 hours. Subsequently, 4% aqueous sodium bicarbonate (40 mL) was added to the mixture and the reaction was extracted with ethyl acetate (3×25 mL). The combined organic layers were washed with brine, dried over anhydrous sodium sulphate and the solvent was removed under reduced pressure to give 106 mg of a yellowish oil. The mixture was purified by column chromatography (C-18 silica from Waters©, reverse phase water/(acetonitrile/methanol 50:50) as eluent [0.1% v/v ammonium formate buffered] 0% to 100%). The organic solvent from the appropriate fractions was evaporated and the aqueous phase basified to pH 10 with ammonium hydroxide. This was extracted with ethyl acetate, dried over sodium sulphate and the solvent removed under reduced pressure to give the title compound as a white solid (55 mg, 60%).

LRMS (m/z): 370 (M+1)$^+$.

Retention Time: 14 min.

$^1$H-NMR δ (DMSO-$d_6$): 6.97 (brs, 2H), 7.00 (s, 1H), 7.22-7.31 (m, 3H), 7.35-7.41 (m, 1H), 7.53-7.64 (m, 2H), 7.67-7.74 (m, 1H), 8.34 (d, J=6 Hz, 1H).

Example 4

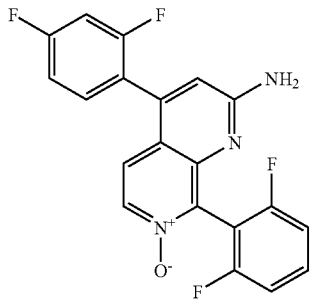

4-(2,4-Difluorophenyl)-8-(2,6-difluorophenyl)-1,7-naphthyridin-2-amine 7-oxide Obtained as a light-brown solid (44%) from the title compound of Example 2 following the experimental procedure as described in Example 3.

LRMS (m/z): 386 (M+1)$^+$.

Retention Time: 12 min.

$^1$H-NMR δ (DMSO-$d_6$): 6.80 (s, 1H), 7.11 (brs, 2H), 7.27-7.41 (m, 4H), 7.56-7.74 (m, 3H), 8.10 (d, J=6 Hz, 1H).

Example 5

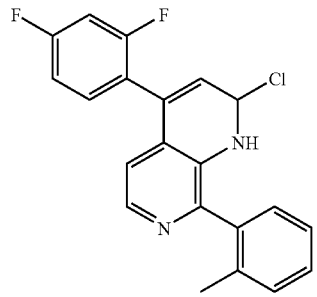

4-(2,4-Difluorophenyl)-8-(2-methylphenyl)-1,7-naphthyridin-2(1H)-one

A suspension of the title compound from Preparation 3 (3.71 g, 6.35 mmol) in 6N aqueous hydrochloric acid (55 mL) was vigorously stirred at 110° C. for 16 hours. After this period of time the mixture was cooled to room temperature and carefully poured into ice-cold 10% aq. sodium carbonate (200 mL). The solid precipitate was filtered, washed with cold water and dried to give the title compound (1.94 g, 88%) as an off-white solid.

LRMS (m/z): 349 (M+1)$^+$.

$^1$H-NMR δ (CDCl$_3$): 2.17 (s, 3H), 6.81 (s, 1H), 7.03-7.18 (m, 3H), 7.29-7.46 (m, 5H), 8.47 (brs, 1H), 8.48 (d, J=6 Hz, 1H).

Example 6

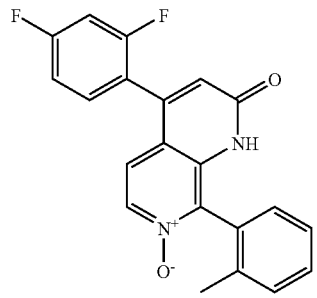

4-(2,4-Difluorophenyl)-8-(2-methylphenyl)-1,7-naphthyridin-2(1H)-one 7-oxide Meta-chloroperbenzoic acid (77%) (1.37 g, 6.12 mmol) was added portionwise to a solution of the title compound from Example 5 (1.40 g, 4.02 mmol) in dichloromethane (22 mL) at 0° C. and the reaction mixture was stirred overnight at room temperature. Then, more dichloromethane was added (100 mL) and the solution was washed with 4% aqueous sodium bicarbonate (4×30 ml) and brine. The organic layer was dried over sodium sulphate and concentrated under reduced pressure to yield the title compound (1.40 g, 96%) as a yellow solid.

LRMS (m/z): 365 (M+1)$^+$.

$^1$H-NMR δ (CDCl$_3$): 2.20 (s, 3H), 6.61 (s, 1H), 7.03-7.18 (m, 3H), 7.36-7.56 (m, 5H), 8.11 (d, J=6 Hz, 1H), 8.19 (brs, 1H).

Example 7

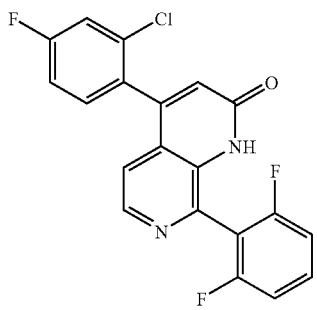

4-(2-Chloro-4-fluorophenyl)-8-(2,6-difluorophenyl)-1,7-naphthyridin-2(1H)-one

Obtained as an off-white solid (38%) from the title compound as described in Preparation 4 following the experimental procedure described in Example 5.

LRMS (m/z): 387, 389 (M+1)$^+$.

$^1$H-NMR δ (CDCl$_3$): 6.76 (s, 1H), 7.07-7.27 (m, 4H), 7.33-7.38 (m, 2H), 7.51-7.61 (m, 1H), 8.49 (d, J=6 Hz, 1H), 8.69 (brs, 1H).

Example 8

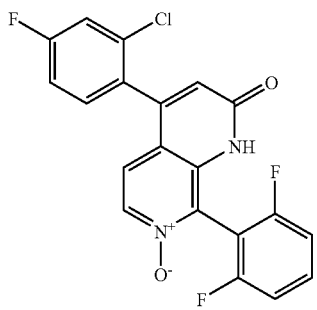

4-(2-Chloro-4-fluorophenyl)-8-(2,6-difluorophenyl)-1,7-naphthyridin-2(1H)-one 7-oxide Obtained as a light-yellow solid (88%) from the title compound of Example 7 following the experimental procedure described in Example 6.

LRMS (m/z): 403, 405 (M+1)$^+$.

$^1$H-NMR δ (CDCl$_3$): 6.56 (s, 1H), 7.04 (d, J=6 Hz, 1H), 7.15-7.23 (m, 3H), 7.34-7.39 (m, 2H), 7.59-7.70 (m, 1H), 8.08 (d, J=6 Hz, 1H), 8.38 (brs, 1H).

Example 9

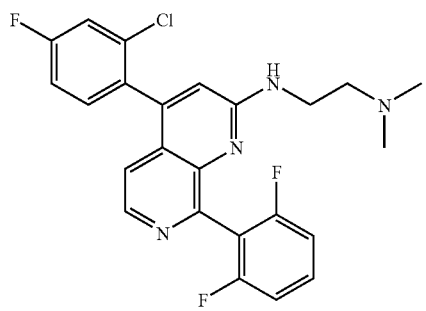

N'-[4-(2-Chloro-4-fluorophenyl)-8-(2,6-difluorophenyl)-1,7-naphthyridin-2-yl]-N,N-dimethylethane-1,2-diamine In a Schlenk tube were charged the title compound from Preparation 5 (140 mg, 0.346 mmol), ethoxyethanol (3 mL), diisopropylethyl amine (0.3 mL, 1.72 mmol) and N,N-dimethylethane-1,2-diamine (0.19 mL, 1.72 mmol). The mixture was submitted to three vacuum-argon cycles and the reaction was stirred at 80° C. under argon for 10 hours. Subsequently, water was added to the cold reaction mixture and it was extracted with ethyl acetate (3×50 mL). The combined organic layers were washed with brine, dried over sodium sulphate and the solvent removed under reduced pressure. The residue was purified by column chromatography (C-18 silica from Waters©, reverse phase water/(acetonitrile/methanol 50:50) as eluent [0.1% v/v ammonium formate buffered] 0% to 100%). The organic solvent from the appropriate fractions was evaporated and the aqueous phase basified to pH 10 with ammonium hydroxide. This was extracted with ethyl acetate, dried over sodium sulphate and the solvent removed under reduced pressure to give the title compound as a light-yellow solid (105 mg, 66%).

LRMS (m/z): 457, 459 (M+1)$^+$.

Retention Time: 11 min.

$^1$H-NMR δ (CDCl$_3$): 2.20 (s, 6H), 2.46 (t, J=6 Hz, 2H), 3.37 (t, J=6 Hz, 2H), 5.52 (brs, 1H), 6.70 (s, 1H), 6.98-7.05 (m, 2H), 7.10-7.16 (m, 2H), 7.28-7.40 (m, 3H), 8.37 (d, J=6 Hz, 1H).

Example 10

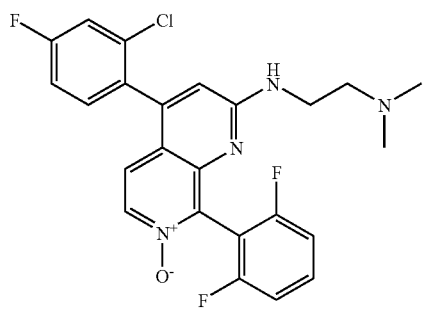

N'-[4-(2-Chloro-4-fluorophenyl)-8-(2,6-difluorophenyl)-7-oxido-1,7-naphthyridin-2-yl]-N,N-dimethylethane-1,2-diamine Obtained as a light-brown solid (12%) from the title compound of in Preparation 6 following the experimental procedure described in Example 9.
LRMS (m/z): 473, 475 (M+1)⁺.
Retention Time: 9 min.
¹H-NMR δ (CDCl₃): 2.20 (s, 6H), 2.44 (t, J=6 Hz, 2H), 3.31 (t, J=6 Hz, 2H), 5.69 (brs, 1H), 6.53 (s, 1H), 7.01-7.17 (m, 4H), 7.26-7.33 (m, 2H), 7.42-7.47 (m, 1H), 8.03 (d, J=6 Hz, 1H).

Example 11

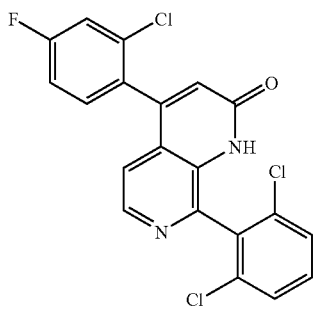

4-(2-Chloro-4-fluorophenyl)-8-(2,6-dichlorophenyl)-1,7-naphthyridin-2(1H)-one

Obtained as an off-white solid (55%) from the title compound of Preparation 7 following the experimental procedure described in Example 5.
LRMS (m/z): 419, 421, 423, 425 (M+1)⁺.
Retention Time: 16 min.
¹H-NMR δ (CDCl₃): 6.78 (s, 1H), 7.10 (d, J=6 Hz, 1H), 7.18-7.24 (m, 1H), 7.35-7.40 (m, 2H), 7.45-7.57 (m, 3H), 8.34 (brs, 1H), 8.50 (d, J=6 Hz, 1H).

Example 12

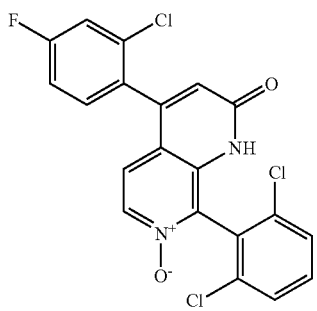

4-(2-Chloro-4-fluorophenyl)-8-(2,6-dichlorophenyl)-1,7-naphthyridin-2(1H)-one 7-oxide Obtained as a light-yellow solid (49%) from the title compound of Example 11 following the experimental procedure described in Example 6.
LRMS (m/z): 435, 437, 439, 441 (M+1)⁺.
Retention Time: 13 min.
¹H-NMR δ (CDCl₃): 6.55 (s, 1H), 7.06 (d, J=6 Hz, 1H), 7.18-7.24 (m, 1H), 7.35-7.44 (m, 2H), 7.51-7.60 (m, 3H), 8.09 (d, J=6 Hz, 1H), 8.29 (brs, 1H).

Example 13

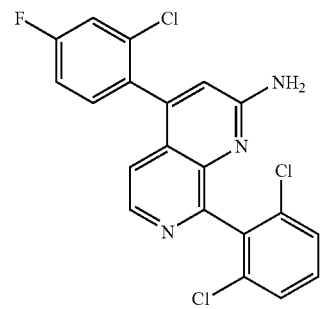

4-(2-Chloro-4-fluorophenyl)-8-(2,6-dichlorophenyl)-1,7-naphthyridin-2-amine

In a Schlenk tube were charged the compound as described in Preparation 8 (168 mg, 0.383 mmol), 1,1-diphenylmethanimine (0.09 mL, 0.537 mmol), rac-2,2'-bis(diphenylphosphino)-1,1'-binaphthyl (racemic BINAP) (25 mg, 0.039 mmol), cesium carbonate (251 mg, 0.77 mmol) and toluene (2.5 mL). The mixture was submitted to three vacuum-argon cycles, then palladium (II) acetate (5 mg, 0.023 mmol) was added and the mixture was purged in the same way. The reaction was stirred at 100° C. under argon for 16 hours. Subsequently, the cold reaction mixture was filtered through Celite® and the filter cake was washed with ethyl acetate (20 mL). The solvent was removed under reduced pressure and the residue re-dissolved in tetrahydrofuran (4 mL). Then, 2N aqueous HCl was added (1 mL) and the mixture vigorously stirred at room temperature for 4 hours. The pH was adjusted to 10 with 2N aqueous NaOH and the aqueous phase extracted with dichloromethane (3×20 mL). The solvent was evaporated and the crude material directly purified by column chromatography (dichloromethane/ethanol/ammonium hydroxide 200:8:1). The appropriate fractions were evaporated under reduced pressure to give the title compound as a light-brown solid (71 mg, 44%).
LRMS (m/z): 418, 420, 422, 424 (M+1)⁺.
Retention Time: 16 min.
¹H-NMR δ (CDCl₃): 4.89 (brs, 2H), 6.79 (s, 1H), 7.14-7.20 (m, 2H), 7.31-7.40 (m, 3H), 7.44-7.47 (m, 2H), 8.43 (d, J=6 Hz, 1H).

Example 14

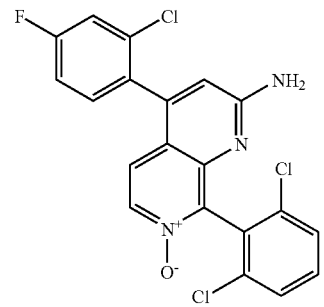

4-(2-Chloro-4-fluorophenyl)-8-(2,6-dichlorophenyl)-1,7-naphthyridin-2-amine 7-oxide Obtained as a yellowish solid (45%) from the title compound of Preparation 9 following the experimental procedure described in Example 13.

LRMS (m/z): 434, 436, 438, 440 (M+1)$^+$.

Retention Time: 13 min.

$^1$H-NMR δ (CDCl$_3$): 5.01 (brs, 2H), 6.60 (s, 1H), 7.13-7.20 (m, 2H), 7.32-7.41 (m, 3H), 7.46-7.49 (m, 2H), 8.06 (d, J=6 Hz, 1H).

Example 15

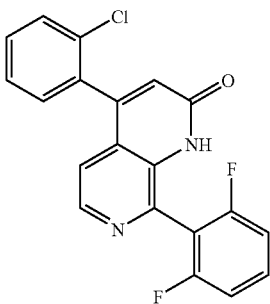

4-(2-Chlorophenyl)-8-(2,6-difluorophenyl)-1,7-naphthyridin-2(1H)-one

Obtained as a beige solid (69%) from the title compound of Preparation 10 following the experimental procedure described in Example 5.

LRMS (m/z): 369, 371 (M+1)$^+$.

$^1$H-NMR δ (CDCl$_3$): 6.78 (s, 1H), 7.10-7.18 (m, 3H), 7.36 (dd, J=6 and 3 Hz, 1H), 7.43-7.62 (m, 4H), 8.48 (d, J=6 Hz, 1H), 8.61 (brs, 1H).

Example 16

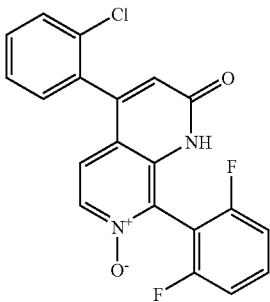

4-(2-Chlorophenyl)-8-(2,6-difluorophenyl)-1,7-naphthyridin-2(1H)-one 7-oxide

Obtained as a light-yellow solid (89%) from the title compound of Example 15 following the experimental procedure described in Example 6.

LRMS (m/z): 385, 387 (M+1)$^+$.

$^1$H-NMR δ (CDCl$_3$): 6.57 (s, 1H), 7.06 (d, J=6 Hz, 1H), 7.15-7.24 (m, 2H), 7.36-7.67 (m, 5H), 8.09 (d, J=6 Hz, 1H), 8.41 (brs, 1H).

Example 17

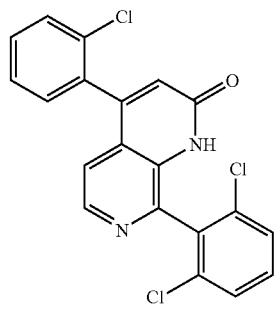

4-(2-Chlorophenyl)-8-(2,6-dichlorophenyl)-1,7-naphthyridin-2(1H)-one

Obtained as a beige solid (97%) from the title compound of Preparation 11 following the experimental procedure as described in Example 5.

LRMS (m/z): 401, 403, 405, 407 (M+1)$^+$.

$^1$H-NMR δ (CDCl$_3$): 6.78 (s, 1H), 7.11 (d, J=6 Hz, 1H), 7.38-7.62 (m, 7H), 8.39 (brs, 1H), 8.49 (d, J=6 Hz, 1H).

Example 18

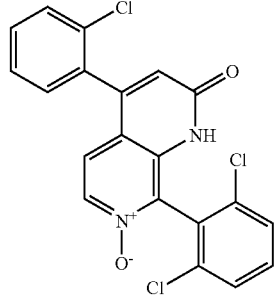

4-(2-Chlorophenyl)-8-(2,6-dichlorophenyl)-1,7-naphthyridin-2(1H)-one 7-oxide

Obtained as a light-yellow solid (91%) from the title compound of Example 17 following the experimental procedure described in Example 6.

LRMS (m/z): 417, 419, 421, 423 (M+1)$^+$.

$^1$H-NMR δ (CDCl$_3$): 6.58 (s, 1H), 7.07 (d, J=6 Hz, 1H), 7.38-7.61 (m, 7H), 8.08 (d, J=6 Hz, 1H), 8.28 (brs, 1H).

Example 19

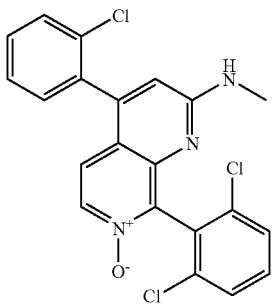

4-(2-Chlorophenyl)-8-(2,6-dichlorophenyl)-N-methyl-1,7-naphthyridin-2-amine 7-oxide In a sealed tube were charged the title compound from Preparation 12 (80 mg, 0.18 mmol), ethoxyethanol (1 mL) and N-methyl amine (2M in THF, 0.46 mL, 0.92 mmol). The mixture was stirred at 75° C. under argon for 5 hours. The solvent was removed from the cold reaction mixture and the residue was directly purified by column chromatography on silica gel, using hexane/ethyl acetate (7:3 to ethyl acetate) as eluent, to yield the title compound (58 mg, 72%) as a yellowish solid.

LRMS (m/z): 430, 432, 434, 436 (M+1)$^+$.

Retention Time: 15 min.

$^1$H-NMR δ (CDCl$_3$): 2.81 (d, J=3 Hz, 3H), 5.00 (brs, 1H), 6.54 (s, 1H), 7.13 (d, J=6 Hz, 1H), 7.33-7.49 (m, 6H), 7.56-7.59 (m, 1H), 8.03 (d, J=6 Hz, 1H).

Example 20

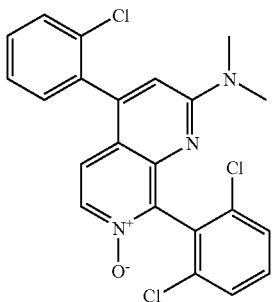

4-(2-Chlorophenyl)-8-(2,6-dichlorophenyl)-N,N-dimethyl-1,7-naphthyridin-2-amine 7-oxide Obtained as a yellow solid (74%) from the title compound of Preparation 12 and N,N-dimethyl amine following the experimental procedure described in Example 19.

LRMS (m/z): 444, 446, 448, 450 (M+1)$^+$.

Retention Time: 17 min.

$^1$H-NMR δ (CDCl$_3$): 3.02 (s, 6H), 6.77 (s, 1H), 7.13 (d, J=6 Hz, 1H), 7.33-7.49 (m, 6H), 7.57-7.60 (m, 1H), 8.00 (d, J=6 Hz, 1H).

Example 21

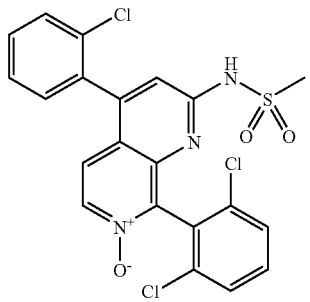

N-[4-(2-Chlorophenyl)-8-(2,6-dichlorophenyl)-7-oxido-1,7-naphthyridin-2-yl]methanesulfonamide To a solution of the title compound of Preparation 12 (100 mg, 0.23 mmol) in DMF (1 mL) under argon were added methanesulfonamide (87 mg, 0.92 mmol) and sodium hydride (60% in mineral oil, 37 mg, 0.92 mmol). The reaction was stirred at 50° C. for 48 hours. Then, saturated aqueous ammonium chloride (20 mL) was added and the mixture extracted with dichloromethane (3×20 mL). The combined organic layers were washed with brine, dried over sodium sulphate and the solvent removed under reduced pressure. The residue was purified by column chromatography on silica gel, using hexane/ethyl acetate (1:1 to 2:8) as eluent, to yield the title compound (22 mg, 19%) as a brown solid.

LRMS (m/z): 494, 496, 498, 500 (M+1)$^+$.

Retention Time: 13 min.

$^1$H-NMR δ (CD$_3$OD): 2.96 (s, 3H), 7.03 (s, 1H), 7.50-7.62 (m, 8H), 7.65-7.70 (m, 1H), 8.27 (d, J=6 Hz, 1H).

Example 22

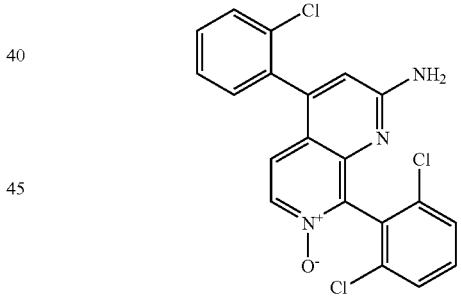

4-(2-Chlorophenyl)-8-(2,6-dichlorophenyl)-1,7-naphthyridin-2-amine 7-oxide

In a Schlenk tube were charged the compound of Preparation 12 (310 mg, 0.71 mmol), 1,1-diphenylmethanimine (0.167 mL, 1 mmol), rac-2,2'-bis(diphenylphosphino)-1,1'-binaphthyl (racemic BINAP) (44 mg, 0.07 mmol), cesium carbonate (347 mg, 1.07 mmol) and toluene (3.5 mL). The mixture was submitted to three vacuum-argon cycles, then palladium (II) acetate (8 mg, 0.04 mmol) was added and the mixture was purged in the same way. The reaction was stirred at 100° C. under argon for 16 hours. Subsequently, the cold reaction mixture was filtered through Celite® and the filter cake was washed with ethyl acetate (20 mL). The solvent was removed under reduced pressure and the residue redissolved in tetrahydrofuran (2.5 mL). Then, 2N aqueous HCl was added (1 mL) and the mixture vigorously stirred at room temperature for 4 hours. The pH was adjusted to 10 with 2N aqueous NaOH and the aqueous phase extracted with dichloromethane (3×20 mL). The solvent was evaporated and the crude material directly purified by column chromatography (C-18 silica from Waters©, reverse phase water/(acetonitrile/methanol 50:50) as eluent [0.1% v/v ammonium formate buffered] 0% to 100%). The organic solvent from the appropriate fractions was evaporated and the aqueous phase basified to pH 10 with ammonium hydroxide. This was extracted with dichloromethane, dried over sodium sulphate and the solvent removed under reduced pressure to give the title compound as a light-brown solid (125 mg, 42%).

LRMS (m/z): 416, 418, 420, 422 (M+1)$^+$.

Retention Time: 13 min.

$^1$H-NMR δ (CDCl$_3$): 4.96 (brs, 2H), 6.63 (s, 1H), 7.17 (d, J=6 Hz, 1H), 7.36-7.50 (m, 6H), 7.57-7.60 (m, 1H), 8.06 (d, J=6 Hz, 1H).

Example 23

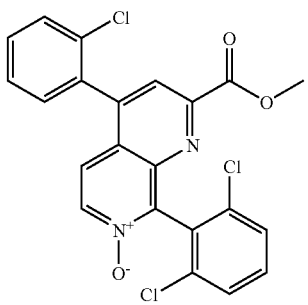

Methyl 4-(2-chlorophenyl)-8-(2,6-dichlorophenyl)-1,7-naphthyridine-2-carboxylate 7-oxide Obtained as an off-white solid (26%) from the title compound of Preparation 13 and methyl piruvate following the experimental procedure described in Example 1.

LRMS (m/z): 459, 461, 463, 465 (M+1)$^+$.

Retention Time: 16 min.

$^1$H-NMR δ (DMSO-d$_6$): 3.91 (s, 3H), 7.63-7.85 (m, 8H), 8.09 (s, 1H), 8.56 (d, J=6 Hz, 1H).

Example 24

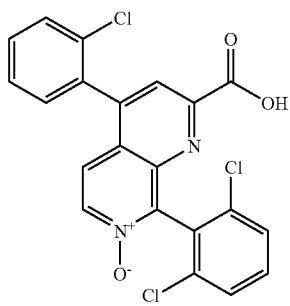

4-(2-Chlorophenyl)-8-(2,6-dichlorophenyl)-1,7-naphthyridine-2-carboxylic acid 7-oxide Obtained as an off-white solid (7%) from the title compound of Preparation 13 following the experimental procedure described in Example 1.

LRMS (m/z): 445, 447, 449, 451 (M+1)$^+$.

Retention Time: 14 min.

$^1$H-NMR δ (DMSO-d$_6$): 7.56-7.78 (m, 8H), 8.00 (s, 1H), 8.48 (d, J=6 Hz, 1H).

Example 25

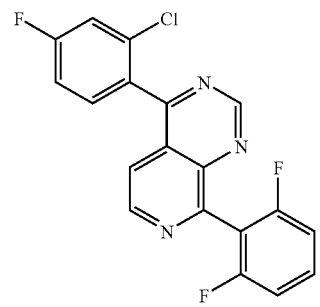

4-(2-Chloro-4-fluorophenyl)-8-(2,6-difluorophenyl)pyrido[3,4-d]pyrimidine a) N'-[4-(2-chloro-4-fluorobenzoyl)-2-(2,6-difluorophenyl)pyridin-3-yl]-N,N-dimethyl-imidoformamide In a sealed tube, the title compound from Preparation 4f (200 mg, 0.55 mmol) and N-(dimethoxymethyl)-N,N-dimethylamine (DMF-DMA) (0.109 mL, 0.82 mmol) were dissolved in acetonitrile (2 mL). The mixture was stirred at 85° C. under argon for 18 hours. After this period of time, the solvent was removed from the cold reaction mixture and the title compound used directly in the next step without further purification (210 mg, 86%).

LRMS (m/z): 418, 420 (M+1)$^+$.

$^1$H-NMR δ (CDCl$_3$): 2.28 (s, 3H), 2.74 (s, 3H), 6.87-7.01 (m, 4H), 7.13 (dd, J=3 and 9 Hz, 1H), 7.24-7.34 (m, 1H), 7.41 (dd, J=6 and 9 Hz, 1H), 7.52 (d, J=6 Hz, 1H), 8.50 (d, J=6 Hz, 1H).

b) 4-(2-Chloro-4-fluorophenyl)-8-(2,6-difluorophenyl)pyrido[3,4-d]pyrimidine

The title compound from Example 25a (210 mg, 0.5 mmol) was dissolved in anhydrous ethanol (4 mL) and ammonium acetate (83 mg, 1.075 mmol) was added portionwise. The mixture was heated at 80° C. for 18 hours. The solvent was removed under reduced pressure and the residue directly purified by column chromatography on silica gel, using hexane/ethyl acetate (10:1) as eluent, to yield the title compound (84 mg, 45%) as an off-white solid.

LRMS (m/z): 372, 374 (M+1)$^+$.

Retention Time: 16 min.

¹H-NMR δ (CDCl₃): 7.09-7.15 (m, 2H), 7.22-7.27 (m, 1H), 7.39 (dd, J=3 and 9 Hz, 1H), 7.47-7.58 (m, 3H), 8.67 (d, J=6 Hz, 1H), 9.53 (s, 1H).

Example 26

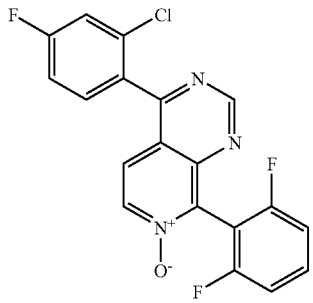

4-(2-Chloro-4-fluorophenyl)-8-(2,6-difluorophenyl) pyrido[3,4-d]pyrimidine 7-oxide Meta-chloroperbenzoic acid (77%) (30 mg, 0.13 mmol) was added portionwise to a solution of the title compound from Example 25 (50 mg, 0.13 mmol) in dichloromethane (2.5 mL) at 0° C. and the reaction mixture was stirred overnight at room temperature. Then, more dichloromethane was added (50 mL) and the solution was washed with 1N NaOH (2×30 ml) and brine. The organic layer was dried over sodium sulphate and concentrated under reduced pressure to yield an oil which was purified by column chromatography on silica gel, using hexane/ethyl acetate (5:1) as eluent, to yield the title compound (24 mg, 46%) as an off-white solid.

LRMS (m/z): 388, 390 (M+1)⁺.
Retention Time: 15 min.
¹H-NMR δ (CDCl₃): 7.11-7.17 (m, 2H), 7.22-7.29 (m, 1H), 7.38 (dd, J=3 and 9 Hz, 1H), 7.51-7.63 (m, 3H), 8.32 (d, J=9 Hz, 1H), 9.40 (s, 1H).

Example 27

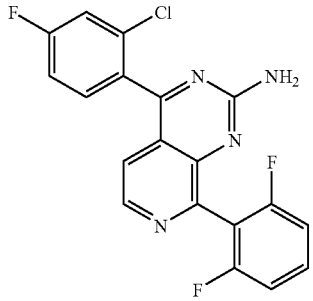

4-(2-Chloro-4-fluorophenyl)-8-(2,6-difluorophenyl) pyrido[3,4-d]pyrimidin-2-amine a) tert-Butyl (1Z)-[(tert-butoxycarbonyl)amino][(4-(2-chloro-4-fluorobenzoyl)-2-(2,6-difluorophenyl)-3-yl)amino]methylenecarbamate To a solution of the title compound from Preparation 4f (200 mg, 0.55 mmol) in dichloromethane (4 mL) were sequentially added tert-butyl (1Z)-[(tert-butoxycarbonyl)-amino](methylthio)methylenecarbamate (639 mg, 2.2 mmol), mercury (II) chloride (597 mg, 2.2 mmol) and triethylamine (0.23 mL, 1.65 mmol) and the mixture was stirred at room temperature for 18 hours. The mixture was filtered through Celite® and the filter cake was washed with ethyl acetate (20 mL). Water was added (30 mL) and the aqueous phase extracted with ethyl acetate (3×20 mL). The combined organic layers were washed with brine, dried over sodium sulphate and the solvent removed under reduced pressure to give an oily material which was purified by column chromatography on silica gel, using hexane/ethyl acetate (10:1 to 8:1) as eluent, to yield the title compound (246 mg, 74%) as an off-white solid.

LRMS (m/z): 605, 607 (M+1)⁺.
¹H-NMR δ (CDCl₃): 1.35 (s, 9H), 1.41 (s, 9H), 6.99-7.08 (m, 3H), 7.18 (dd, J=3 and 9 Hz, 1H), 7.37-7.45 (m, 2H), 7.83 (dd, J=6 and 9 Hz, 1H), 8.73 (d, J=6 Hz, 1H), 10.20 (brs, 1H), 11.19 (brs, 1H).

b) 4-(2-Chloro-4-fluorophenyl)-8-(2,6-difluorophenyl)pyrido[3,4-d]pyrimidin-2-amine The title compound from Example 27a (246 mg, 0.41 mmol) was dissolved in HCl (4M in dioxane, 6 mL) and the reaction mixture was stirred at room temperature for 18 hours. Subsequently, the solvent was removed and the residue suspended in water (50 mL). The pH was adjusted to 8-9 with solid sodium bicarbonate and the aqueous solution extracted with ethyl acetate (3×30 mL). The combined organic layers were washed with brine, dried over sodium sulphate and the solvent removed under reduced pressure to give a residue which was purified by column chromatography on silica gel, using hexane/ethyl acetate (5:1) as eluent, to yield the title compound (102 mg, 65%) as a light-brown solid.

LRMS (m/z): 387, 389 (M+1)⁺.
Retention Time: 15 min.
¹H-NMR δ (CDCl₃): 5.35 (brs, 2H), 7.03-7.11 (m, 3H), 7.18-7.25 (m, 1H), 7.36 (dd, J=3 and 9 Hz, 1H), 7.42-7.49 (m, 2H), 8.49 (d, J=6 Hz, 1H).

Example 28

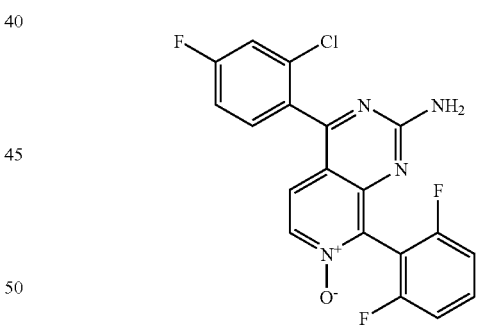

4-(2-Chloro-4-fluorophenyl)-8-(2,6-difluorophenyl) pyrido[3,4-d]pyrimidin-2-amine 7-oxide a) tert-Butyl (1Z)-[(tert-butoxycarbonyl)amino][(4-(2-chloro-4-fluorobenzoyl)-2-(2,6-difluorophenyl)-1-oxidopyridin-3-yl)amino]methylenecarbamate Obtained as an off-white solid (26%) from the title compound of Preparation 14 following the experimental procedure described in Example 27a.

LRMS (m/z): 621, 623 (M+1)⁺.
¹H-NMR δ (CDCl₃): 1.40 (s, 18H), 7.01-7.09 (m, 3H), 7.16 (dd, J=3 and 9 Hz, 1H), 7.43-7.52 (m, 2H), 7.71-7.76 (m 1H), 8.28 (d, J=9 Hz, 1H), 10.16 (brs, 1H), 11.08 (brs, 1H).

b) 4-(2-Chloro-4-fluorophenyl)-8-(2,6-difluorophenyl)pyrido[3,4-d]pyrimidin-2-amine 7-oxide Obtained as a light-brown solid (71%) from the title compound of Example 28a following the experimental procedure described in Example 27b.

LRMS (m/z): 403, 405 (M+1)+.

Retention Time: 13 min.

$^1$H-NMR δ (CDCl$_3$): 7.06-712 (m, 2H), 7.18-7.26 (m, 1H), 7.26 (d, J=9 Hz, 1H), 7.35 (dd, J=3 and 9 Hz, 1H), 7.45-7.57 (m, 2H), 8.01 (d, J=9 Hz, 1).

Example 29

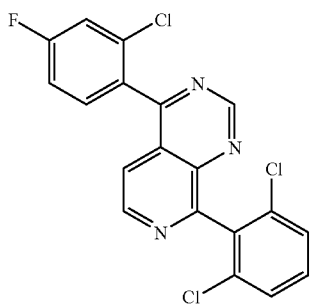

4-(2-Chloro-4-fluorophenyl)-8-(2,6-dichlorophenyl)pyrido[3,4-d]pyrimidine a) N'-[4-(2-Chloro-4-fluorobenzoyl)-2-(2,6-dichlorophenyl)pyridin-3-yl]-N,N-dimethyl-imidoformamide Obtained as an oil (95%) from the title compound of Preparation 7a following the experimental procedure described in Example 25a.

LRMS (m/z): 450, 452, 454, 456 (M+1)+.

$^1$H-NMR δ (CDCl$_3$): 2.23 (s, 3H), 2.68 (s, 3H), 6.92 (s, 1H), 6.95-7.01 (m, 1H), 7.12 (dd, J=3 and 9 Hz, 1H), 7.18-7.23 (m, 1H), 7.31-7.34 (m, 2H), 7.42 (dd, J=6 and 9 Hz, 1H), 7.53 (d, J=6 Hz, 1H), 8.48 (d, J=6 Hz, 1H).

b) 4-(2-Chloro-4-fluorophenyl)-8-(2,6-dichlorophenyl)pyrido[3,4-d]pyrimidine

Obtained as an off-white solid (41%) from the title compound of Example 29a following the experimental procedure described in Example 25b.

LRMS (m/z): 404, 406, 408, 410 (M+1)+.

Retention Time: 17 min.

$^1$H-NMR δ (CDCl$_3$): 7.23-7.28 (m, 1H), 7.38-7.45 (m, 2H), 7.51-7.59 (m, 4H), 8.87 (d, J=6 Hz, 1H), 9.51 (s, 1H).

Example 30

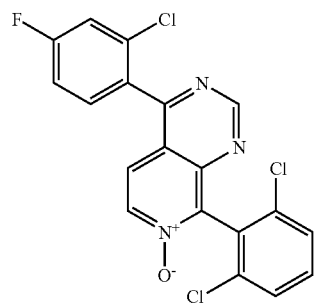

4-(2-Chloro-4-fluorophenyl)-8-(2,6-dichlorophenyl)pyrido[3,4-d]pyrimidine 7-oxide Obtained as an off-white solid (46%) from the title compound of Example 29 following the experimental procedure described in Example 26.

LRMS (m/z): 420, 422, 424, 426 (M+1)+.

Retention Time: 15 min.

$^1$H-NMR δ (CDCl$_3$): 7.24-7.30 (m, 1H), 7.37-7.41 (m, 1H), 7.48-7.62 (m, 5H), 8.32 (d, J=6 Hz, 1H), 9.38 (s, 1H).

Example 31

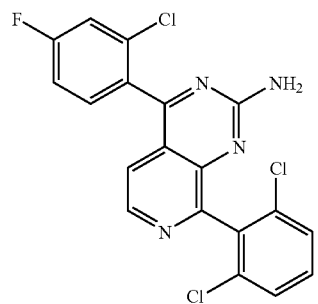

4-(2-Chloro-4-fluorophenyl)-8-(2,6-dichlorophenyl)pyrido[3,4-d]pyrimidin-2-amine a) tert-Butyl (1Z)-[(tert-butoxycarbonyl)amino][(4-(2-chloro-4-fluorobenzoyl)-2-(2,6-dichlorophenyl)-3-yl)amino]methylenecarbamate Obtained as an off-white solid (92%) from the title compound of Preparation 7a following the experimental procedure described in Example 27a.

LRMS (m/z): 637, 639, 641, 643 (M+1)+.

$^1$H-NMR δ (CDCl$_3$): 1.36 (s, 18H), 7.01-7.06 (m, 1H), 7.14-7.17 (m, 1H), 7.28-7.33 (m, 1H), 7.41-7.46 (m 3H), 7.82-7.87 (m, 1H), 8.72 (d. J=6 Hz, 1H), 9.97 (brs, 1H), 11.12 (brs, 1H).

b) 4-(2-Chloro-4-fluorophenyl)-8-(2,6-dichlorophenyl)pyrido[3,4-d]pyrimidin-2-amine Obtained as a light-brown solid (87%) from the title compound of Example 31a following the experimental procedure described in Example 27b.

LRMS (m/z): 419, 421, 423, 425 (M+1)+.
Retention Time: 16 min.
$^1$H-NMR δ (CDCl$_3$): 5.36 (brs, 2H), 7.19-7.29 (m, 2H), 7.34-7.39 (m, 2H), 7.46-7.53 (m, 3H), 8.48 (d, J=6 Hz, 1H).

Example 32

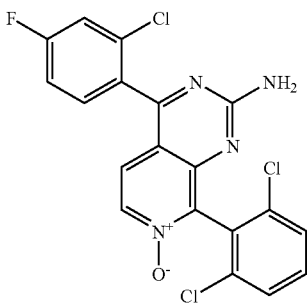

4-(2-Chloro-4-fluorophenyl)-8-(2,6-dichlorophenyl) pyrido[3,4-d]pyrimidin-2-amine 7-oxide a) tert-Butyl (1Z)-[(tert-butoxycarbonyl)amino][(4-(2-chloro-4-fluorobenzoyl)-2-(2,6-dichlorophenyl)-1-oxidopyridin-3-yl)amino]methylenecarbamate Obtained as a yellow oil (75%) from the title compound of Preparation 15 following the experimental procedure described in Example 27a.
LRMS (m/z): 653, 655, 657, 659 (M+1)+.

b) 4-(2-Chloro-4-fluorophenyl)-8-(2,6-dichlorophenyl)pyrido[3,4-d]pyrimidin-2-amine 7-oxide Obtained as a light-brown solid (87%) from the title compound of Example 32a following the experimental procedure described in Example 27b.
LRMS (m/z): 435, 437, 439, 441 (M+1)+.
Retention Time: 13 min.
$^1$H-NMR δ (CDCl$_3$): 5.39 (brs, 2H), 7.19-7.30 (m, 2H), 7.35 (dd, J=3 and 6 Hz, 1H), 7.39-7.46 (m, 1H), 7.49-7.54 (m, 3H), 8.00 (d, J=6 Hz, 1H).

Example 33

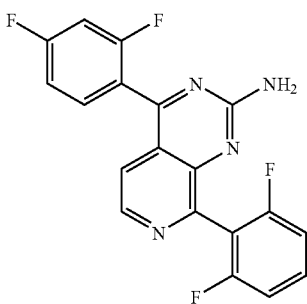

4-(2,4-Difluorophenyl)-8-(2,6-difluorophenyl)pyrido [3,4-d]pyrimidin-2-amine a) tert-Butyl (1Z)-[(tert-butoxycarbonyl)amino][(4-(2,4-difluorobenzoyl)-2-(2,6-difluorophenyl)-3-yl) amino]methylenecarbamate Obtained as a brownish solid (99%) from the title compound of Preparation 1g following the experimental procedure described in Example 27a.
LRMS (m/z): 589 (M+1)+.
$^1$H-NMR δ (CDCl$_3$): 1.29 (s, 9H), 1.41 (s, 9H), 6.96-7.12 (m, 4H), 7.36-7.47 (m, 2H), 7.88-7.96 (m, 1H), 8.70 (d. J=6 Hz, 1H), 10.27 (brs, 1H), 11.22 (brs, 1H).

b) 4-(2,4-Difluorophenyl)-8-(2,6-difluorophenyl) pyrido[3,4-d]pyrimidin-2-amine

Obtained as a light-yellow solid (67%) from the title compound of Example 33a following the experimental procedure described in Example 27b.
LRMS (m/z): 371 (M+1)+.
Retention Time: 15 min.
$^1$H-NMR δ (CDCl$_3$): 5.35 (brs, 2H), 7.04-7.16 (m, 4H), 7.40-7.48 (m, 2H), 7.57-7.65 (m, 1H), 8.52 (d, J=6 Hz, 1H).

Example 34

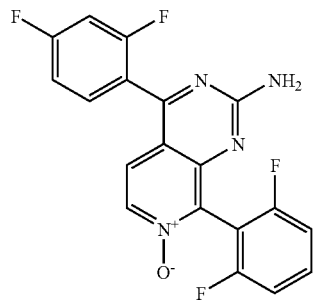

4-(2,4-Difluorophenyl)-8-(2,6-difluorophenyl)pyrido [3,4-d]pyrimidin-2-amine 7-oxide a) tert-Butyl (1Z)-[(tert-butoxycarbonyl)amino][(4-(2,4-difluorobenzoyl)-2-(2,6-difluorophenyl)-1-oxidopyridin-3-yl)amino]methylenecarbamate Obtained as a yellow oil (22%) from the title compound of Preparation 2a following the experimental procedure described in Example 27a.
LRMS (m/z): 605 (M+1)+.
$^1$H-NMR δ (CDCl$_3$): 1.35 (s, 9H), 1.41 (s, 9H), 6.84-6.91 (m, 1H), 6.97-7.09 (m, 3H), 7.47-7.55 (m, 2H), 7.81-7.89 (m, 1H), 8.30 (d. J=6 Hz, 1H), 10.24 (brs, 1H), 11.11 (brs, 1H).

b) 4-(2,4-Difluorophenyl)-8-(2,6-difluorophenyl) pyrido[3,4-d]pyrimidin-2-amine 7-oxide Obtained as a light-brown solid (56%) from the title compound of Example 34a following the experimental procedure described in Example 27b.
LRMS (m/z): 387 (M+1)+.
Retention Time: 12 min.

$^1$H-NMR δ (CDCl$_3$): 5.36 (brs, 2H), 7.02-7.15 (m, 4H), 7.42 (dd, J=3 and 6 Hz, 1H), 7.47-7.64 (m, 2H), 8.04 (d, J=6 Hz, 1H).

Composition Example 1

50,000 capsules each containing 100 mg of 4-(2,4-Difluorophenyl)-8-(2,6-difluorophenyl)-1,7-naphthyridin-2-amine 7-oxide (active ingredient) were prepared according to the following formulation:

| | |
|---|---|
| Active ingredient | 5 Kg |
| Lactose monohydrate | 10 Kg |
| Colloidal silicon dioxide | 0.1 Kg |
| Corn starch | 1 Kg |
| Magnesium stearate | 0.2 Kg |

Procedure

The above ingredients were sieved through a 60 mesh sieve, and were loaded into a suitable mixer and filled into 50,000 gelatine capsules.

Composition Example 2

50,000 tablets each containing 50 mg of 4-(2,4-Difluorophenyl)-8-(2,6-difluorophenyl)-1,7-naphthyridin-2-amine 7-oxide (active ingredient) were prepared from the following formulation:

| | |
|---|---|
| Active ingredient | 2.5 Kg |
| Microcrystalline cellulose | 1.95 Kg |
| Spray dried lactose | 9.95 Kg |
| Carboxymethyl starch | 0.4 Kg |
| Sodium stearyl fumarate | 0.1 Kg |
| Colloidal silicon dioxide | 0.1 Kg |

Procedure

All the powders were passed through a screen with an aperture of 0.6 mm, then mixed in a suitable mixer for 20 minutes and compressed into 300 mg tablets using 9 mm disc and flat bevelled punches. The disintegration time of the tablets was about 3 minutes.

The invention claimed is:

1. A compound of formula (I)

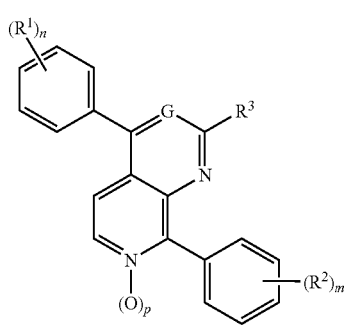

(I)

wherein:

G is chosen from nitrogen and =CH—;
R$^1$ is chosen from halogen atoms, C$_{1-4}$ alkyl optionally substituted with one, two or three halogen atoms, and C$_{1-4}$ alkoxy;
R$^2$ is chosen from halogen atoms, hydroxy, C$_{1-4}$ alkyl, C$_{1-4}$ alkoxy, C$_{1-4}$ alkylthio, C$_{1-4}$ alkoxy-C$_{1-4}$ alkoxy, morpholin-C$_{1-4}$ alkoxy, C$_{1-4}$ alkanesulfonamide, and (C$_{1-4}$ alkoxy-C$_{1-4}$ alkyl)carbamoyl;
R$^3$ is chosen from hydrogen, hydroxy, —NR$^4$R$^5$, —NH—(CH$_2$)$_q$—NR$^4$R$^5$, —S—(CH$_2$)$_q$—NR$^4$R$^5$—O—(CH$_2$)$_q$—NR$^4$R$^5$, —NHS(O)$_2$R$^4$, —NHCOR$^4$, —NHC(O)OR$^4$, COOR$^4$, and CONHR$^4$;
R$^4$ and R$^5$ are independently chosen from hydrogen and C$_{1-4}$ alkyl;
n is an integer from 0 to 4;
m is an integer from 0 to 4;
p is 0 or 1; and
q is an integer from 1 to 4,
or a pharmaceutically acceptable salt thereof,
with the proviso that when G is =CH—, R$^3$ is not hydrogen.

2. A compound according to claim 1, wherein p is 1.

3. A compound according to claim 1, wherein n is an integer from 1 to 2 and each R$^1$ is independently chosen from halogen atoms and C1-4 alkyl.

4. A compound according to claim 3, wherein at least one group R$^1$ is at an ortho position with respect to the carbon atom through which the phenyl group is attached to the naphtyridine or pyrido[3,4-d]pyrimidine core.

5. A compound according to claim 4, wherein R$^1$ is chosen from halogen atoms.

6. A compound according to claim 5, wherein R$^1$ is chosen from chlorine and fluorine.

7. A compound according to claim 1, wherein m is an integer from 1 to 2 and each R$^2$ is independently chosen from halogen atoms and C$_{1-4}$ alkyl.

8. A compound according to claim 7, wherein at least one group R$^2$ is at an ortho position with respect to the carbon atom through which the phenyl group is attached to the naphtyridine or pyrido[3,4-d]pyrimidine core.

9. A compound according to claim 8, wherein m is 2 and both R$^2$ groups are at an ortho position with respect to the carbon atom through which the phenyl group is attached to the naphtyridine or pyrido[3,4-d]pyrimidine core.

10. A compound according to claim 9, wherein both R$^2$ groups are chosen from halogen atoms.

11. A compound according to claim 10, wherein both R$^2$ groups are identical and are chosen from chlorine and fluorine.

12. A compound according to claim 1, wherein R$^3$ is chosen from hydrogen, hydroxy, —NR$^4$R$^5$, —NH—(CH$_2$)$_q$—NR$^4$R$^5$, and NHS(O)$_2$R$^4$, wherein R$^4$ and R$^5$ are independently chosen from hydrogen and methyl, and q is an integer from 2 to 4.

13. A compound according to claim 12, wherein R$^3$ is chosen from —NR$^4$R$^5$, —NH—(CH$_2$)$_q$—NR$^4$R$^5$ wherein R$^4$ and R$^5$ are independently chosen from hydrogen and methyl, and q is 2.

14. A compound according to claim 13, wherein R$^3$ is —NH$_2$.

15. A compound according to claim 1, chosen from:
4-(2,4-Difluorophenyl)-8-(2,6-difluorophenyl)-1,7-naphthyridine-2-carboxylic acid;
4-(2,4-Difluorophenyl)-8-(2,6-difluorophenyl)-1,7-naphthyridine-2-carboxylic acid 7-oxide;
4-(2,4-Difluorophenyl)-8-(2,6-difluorophenyl)-1,7-naphthyridin-2-amine;
4-(2,4-Difluorophenyl)-8-(2,6-difluorophenyl)-1,7-naphthyridin-2-amine 7-oxide;
4-(2,4-Difluorophenyl)-8-(2-methylphenyl)-1,7-naphthyridin-2(1H)-one;

4-(2,4-Difluorophenyl)-8-(2-methylphenyl)-1,7-naphthyridin-2(1H)-one 7-oxide;
4-(2-Chloro-4-fluorophenyl)-8-(2,6-difluorophenyl)-1,7-naphthyridin-2(1H)-one;
4-(2-Chloro-4-fluorophenyl)-8-(2,6-difluorophenyl)-1,7-naphthyridin-2(1H)-one 7-oxide;
N'-[4-(2-Chloro-4-fluorophenyl)-8-(2,6-difluorophenyl)-1,7-naphthyridin-2-yl]-N,N-dimethylethane-1,2-diamine;
N'-[4-(2-Chloro-4-fluorophenyl)-8-(2,6-difluorophenyl)-7-oxido-1,7-naphthyridin-2-yl]-N,N-dimethylethane-1,2-diamine;
4-(2-Chloro-4-fluorophenyl)-8-(2,6-dichlorophenyl)-1,7-naphthyridin-2(1H)-one;
4-(2-Chloro-4-fluorophenyl)-8-(2,6-dichlorophenyl)-1,7-naphthyridin-2(1H)-one 7-oxide;
4-(2-Chloro-4-fluorophenyl)-8-(2,6-dichlorophenyl)-1,7-naphthyridin-2-amine;
4-(2-Chloro-4-fluorophenyl)-8-(2,6-dichlorophenyl)-1,7-naphthyridin-2-amine 7-oxide;
4-(2-Chlorophenyl)-8-(2,6-difluorophenyl)-1,7-naphthyridin-2(1H)-one;
4-(2-Chlorophenyl)-8-(2,6-difluorophenyl)-1,7-naphthyridin-2(1H)-one 7-oxide;
4-(2-Chlorophenyl)-8-(2,6-dichlorophenyl)-1,7-naphthyridin-2(1H)-one;
4-(2-Chlorophenyl)-8-(2,6-dichlorophenyl)-1,7-naphthyridin-2(1H)-one 7-oxide;
4-(2-Chlorophenyl)-8-(2,6-dichlorophenyl)-N-methyl-1,7-naphthyridin-2-amine 7-oxide;
4-(2-Chlorophenyl)-8-(2,6-dichlorophenyl)-N,N-dimethyl-1,7-naphthyridin-2-amine 7-oxide;
N-[4-(2-Chlorophenyl)-8-(2,6-dichlorophenyl)-7-oxido-1,7-naphthyridin-2-yl]methanesulfonamide;
4-(2-Chlorophenyl)-8-(2,6-dichlorophenyl)-1,7-naphthyridin-2-amine 7-oxide;
Methyl 4-(2-chlorophenyl)-8-(2,6-dichlorophenyl)-1,7-naphthyridine-2-carboxylate 7-oxide;
4-(2-Chlorophenyl)-8-(2,6-dichlorophenyl)-1,7-naphthyridine-2-carboxylic acid 7-oxide;
4-(2-Chloro-4-fluorophenyl)-8-(2,6-difluorophenyl)pyrido[3,4-d]pyrimidine;
4-(2-Chloro-4-fluorophenyl)-8-(2,6-difluorophenyl)pyrido[3,4-d]pyrimidine 7-oxide;
4-(2-Chloro-4-fluorophenyl)-8-(2,6-difluorophenyl)pyrido[3,4-d]pyrimidin-2-amine;
4-(2-Chloro-4-fluorophenyl)-8-(2,6-difluorophenyl)pyrido[3,4-d]pyrimidin-2-amine 7-oxide;
4-(2-Chloro-4-fluorophenyl)-8-(2,6-dichlorophenyl)pyrido[3,4-d]pyrimidine;
4-(2-Chloro-4-fluorophenyl)-8-(2,6-dichlorophenyl)pyrido[3,4-d]pyrimidine 7-oxide;
4-(2-Chloro-4-fluorophenyl)-8-(2,6-dichlorophenyl)pyrido[3,4-d]pyrimidin-2-amine;
4-(2-Chloro-4-fluorophenyl)-8-(2,6-dichlorophenyl)pyrido[3,4-d]pyrimidin-2-amine 7-oxide;
4-(2,4-Difluorophenyl)-8-(2,6-difluorophenyl)pyrido[3,4-d]pyrimidin-2-amine; and
4-(2,4-Difluorophenyl)-8-(2,6-difluorophenyl)pyrido[3,4-d]pyrimidin-2-amine 7-oxide.

16. A pharmaceutical composition comprising a compound according to claim 1 and a pharmaceutically acceptable diluent or carrier.

17. A composition comprising:
(i) a compound according to claim 1; and
(ii) another compound chosen from (1) antagonists of M3 muscarinic receptors, (2) β2-agonists, (3) PDE4 inhibitors, (4) corticosteroids, (5) leukotriene D4 antagonists, (6) inhibitors of egfr-kinase, (7) antagonists of the A2B adenosine receptor, (8) NK1 receptor agonists, (9) CRTh2 antagonists, (10) syk kinase inhibitors, (11) CCR3 antagonists, (12) VLA-4 antagonists and (13) a DMARD (disease modifying antirheumatic drug)
for simultaneous, separate or sequential use in the treatment of the human or animal body.

18. A compound according to claim 1, wherein when G is =CH—, $R^3$ is not hydroxy.

* * * * *

UNITED STATES PATENT AND TRADEMARK OFFICE
CERTIFICATE OF CORRECTION

PATENT NO. : 8,334,294 B2  Page 1 of 1
APPLICATION NO. : 12/597187
DATED : December 18, 2012
INVENTOR(S) : Wenceslao Lumeras Amador et al.

It is certified that error appears in the above-identified patent and that said Letters Patent is hereby corrected as shown below:

Title page, item (54), and Column 1, line 1, Title,

"4,8-DIPHENYL-POLYAZANAPHTHALENE DERIVATIVES" should read

"NEW 4,8-DIPHENYL-POLYAZANAPHTHALENE DERIVATIVES."

In Claim 1, col. 80, line 6,

"-S-$(CH_2)_q$-$NR^4R^5$-O-$(CH_2)_q$-$NR^4R^5$" should read

"-S-$(CH_2)_q$-$NR^4R^5$, -O-$(CH_2)_q$-$NR^4R^5$."

Signed and Sealed this
Nineteenth Day of February, 2013

Teresa Stanek Rea
*Acting Director of the United States Patent and Trademark Office*